US012077586B2

(12) United States Patent
De Weerdt et al.

(10) Patent No.: US 12,077,586 B2
(45) Date of Patent: *Sep. 3, 2024

(54) BISPECIFIC ANTIBODIES FOR USE IN THE TREATMENT OF HEMATOLOGICAL MALIGNANCIES

(71) Applicant: LAVA THERAPEUTICS N.V., Utrecht (NL)

(72) Inventors: Iris De Weerdt, Utrecht (NL); Arnon Philip Kater, Utrecht (NL); Paul Willem Henri Ida Parren, Utrecht (NL); Tanja Denise De Gruijl, Utrecht (NL); Johannes Jelle Van Der Vliet, Utrecht (NL); Roeland Lameris, Utrecht (NL)

(73) Assignee: LAVA THERAPEUTICS N.V., Utrecht (NL)

( * ) Notice: Subject to any disclaimer, the term of this patent is extended or adjusted under 35 U.S.C. 154(b) by 657 days.

This patent is subject to a terminal disclaimer.

(21) Appl. No.: 17/277,984

(22) PCT Filed: Sep. 19, 2019

(86) PCT No.: PCT/NL2019/050625
§ 371 (c)(1),
(2) Date: Mar. 19, 2021

(87) PCT Pub. No.: WO2020/060406
PCT Pub. Date: Jun. 26, 2020

(65) Prior Publication Data
US 2021/0371525 A1 Dec. 2, 2021

(30) Foreign Application Priority Data
Sep. 19, 2018 (NL) ..................................... 2021664

(51) Int. Cl.
*C07K 16/28* (2006.01)
*A61K 39/395* (2006.01)
(Continued)

(52) U.S. Cl.
CPC ...... *C07K 16/2809* (2013.01); *A61K 39/3955* (2013.01); *A61P 35/00* (2018.01);
(Continued)

(58) Field of Classification Search
None
See application file for complete search history.

(56) References Cited

U.S. PATENT DOCUMENTS 5,723,309 A 3/1998 Bonneville
6,737,398 B1 5/2004 Gelfand et al.
(Continued)

FOREIGN PATENT DOCUMENTS

CN 104144700 A 11/2014
EP 1229790 A1 8/2002
(Continued)

OTHER PUBLICATIONS

Allison et al., "Structure of a human γδ T-cell antigen receptor", Nature. Jun. 1, 20014, vol. 411, 820-824.
(Continued)

*Primary Examiner* — Daniel E Kolker
*Assistant Examiner* — Hilary Ann Petrash
(74) *Attorney, Agent, or Firm* — COOLEY LLP

(57) ABSTRACT

The present invention relates to novel methods for the treatment of hematological malignancies. In particular, the invention relates to the treatment of hematological malignancies using antibodies comprising a first binding moiety
(Continued)

that is able to bind human CD1d and a second binding moiety that is able to bind the human Vγ9Vδ2-TCR.

13 Claims, 13 Drawing Sheets

Specification includes a Sequence Listing.

(51) Int. Cl.
 *A61P 35/00* (2006.01)
 *A61P 35/02* (2006.01)
(52) U.S. Cl.
 CPC .......... *A61P 35/02* (2018.01); *C07K 2317/22* (2013.01); *C07K 2317/31* (2013.01); *C07K 2317/565* (2013.01); *C07K 2317/569* (2013.01); *C07K 2317/73* (2013.01)

(56) References Cited

U.S. PATENT DOCUMENTS

| | | |
|---|---|---|
| 7,419,958 B2 | 9/2008 | Wilson et al. |
| 7,582,300 B2 | 9/2009 | Gelfand et al. |
| 7,728,114 B2 | 6/2010 | Mach et al. |
| 8,012,484 B2 | 9/2011 | Linden et al. |
| 8,084,020 B2 | 12/2011 | Exley et al. |
| 8,153,426 B2 | 4/2012 | Moser et al. |
| 8,178,098 B2 | 5/2012 | Lahn et al. |
| 8,338,173 B2 | 12/2012 | Moser et al. |
| 10,106,623 B2 | 10/2018 | Uhlin et al. |
| 10,501,540 B2 | 12/2019 | Van Der Vliet et al. |
| 10,501,541 B2 | 12/2019 | Van Der Vliet et al. |
| 10,758,625 B2 | 9/2020 | Yu et al. |
| 11,000,603 B2 | 5/2021 | Yu et al. |
| 11,384,145 B2 | 7/2022 | Van Der Vliet et al. |
| 11,591,394 B2 | 2/2023 | Van Der Vliet et al. |
| 2018/0142020 A1 | 5/2018 | Van Der Vliet et al. |
| 2019/0263908 A1 | 8/2019 | Van Der Vliet et al. |
| 2020/0115450 A1 | 4/2020 | Van Der Vliet et al. |
| 2021/0284730 A1 | 9/2021 | Ganesan et al. |
| 2022/0098301 A1 | 3/2022 | Van Der Vliet et al. |
| 2022/0111043 A1 | 4/2022 | Van Der Vliet et al. |
| 2023/0212290 A1 | 7/2023 | Van Der Vliet et al. |
| 2024/0067726 A1 | 2/2024 | Van Der Vliet et al. |

FOREIGN PATENT DOCUMENTS

| | | |
|---|---|---|
| EP | 1778836 B1 | 8/2010 |
| EP | 1372668 B1 | 12/2011 |
| EP | 1812015 B1 | 1/2012 |
| EP | 3105252 B1 | 7/2019 |
| EP | 3144388 B1 | 7/2020 |
| EP | 4118121 A1 | 1/2023 |
| JP | 2017513521 A | 6/2017 |
| JP | 2018508229 A | 3/2018 |
| WO | WO-9500163 A1 | 1/1995 |
| WO | WO-0122816 A1 | 4/2001 |
| WO | WO-0182960 A1 | 11/2001 |
| WO | WO-0198357 A2 | 12/2001 |
| WO | WO-02076401 A2 | 10/2002 |
| WO | WO-02080967 A1 | 10/2002 |
| WO | WO-03068821 A2 | 8/2003 |
| WO | WO-03080672 A1 | 10/2003 |
| WO | WO-03092615 A2 | 11/2003 |
| WO | WO-2004062551 A2 | 7/2004 |
| WO | WO-2005046711 A2 | 5/2005 |
| WO | WO-2006017954 A1 | 2/2006 |
| WO | WO-2006060117 A2 | 6/2006 |
| WO | WO-2008006895 A2 | 1/2008 |
| WO | WO-2010130830 A2 | 11/2010 |
| WO | WO-2013053021 A1 | 4/2013 |
| WO | WO-2013110531 A1 | 8/2013 |
| WO | WO-2013147606 A1 | 10/2013 |
| WO | WO-2013174403 A1 | 11/2013 |
| WO | WO-2013174404 A1 | 11/2013 |
| WO | WO-2013174509 A1 | 11/2013 |
| WO | WO-2013174510 A1 | 11/2013 |
| WO | WO-2014127785 A1 | 8/2014 |
| WO | WO-2014127906 A1 | 8/2014 |
| WO | WO-2014210522 A1 | 12/2014 |
| WO | WO-2015121383 A1 | 8/2015 |
| WO | WO-2015156673 A1 | 10/2015 |
| WO | WO-2015174439 A1 | 11/2015 |
| WO | WO-2016001276 A1 | 1/2016 |
| WO | WO-2016081518 A2 | 5/2016 |
| WO | WO-2016122320 A1 | 8/2016 |
| WO | WO-2016165302 A1 | 10/2016 |
| WO | WO-2017086367 A1 | 5/2017 |
| WO | WO-2017185662 A1 | 11/2017 |
| WO | WO-2017197347 A1 | 11/2017 |
| WO | WO-2018023111 A1 | 2/2018 |
| WO | WO-2018140831 A2 | 8/2018 |
| WO | WO-2018229163 A1 | 12/2018 |
| WO | WO-2019001276 A1 | 1/2019 |
| WO | WO-2019070424 A1 | 4/2019 |
| WO | WO-2019195535 A1 | 10/2019 |
| WO | WO-2020010250 A2 | 1/2020 |
| WO | WO-2020060405 A1 | 3/2020 |
| WO | WO-2020060406 A1 | 3/2020 |
| WO | WO-2020172596 A1 | 8/2020 |
| WO | WO-2020227457 A1 | 11/2020 |
| WO | WO-2021032960 A1 | 2/2021 |
| WO | WO-2021032961 A1 | 2/2021 |
| WO | WO-2021032963 A1 | 2/2021 |
| WO | WO-2021173896 A1 | 9/2021 |
| WO | WO-2021183845 A1 | 9/2021 |
| WO | WO-2022093888 A1 | 5/2022 |

OTHER PUBLICATIONS

Bachy et al., "CD1d-restricted peripheral T cell lymphoma in mice and humans", J Exp Med. May 2, 2016; 213(5): 841-857. doi: 10.1084/jem.20150794.

Beckman Coulter, Inc., "TCR Vgamma 9", https://www.beckmancoulter.com/wsrportal/page/itemDetails?itemNumber=IM1463#2/10//0/25/1/0/asc/2/IM14631//0/1//0/, retrieved on Sep. 26, 2014, 1 page.

Bedouelle et al., "Diversity and junction residues as hotspots of binding energy in an antibody neutralizing the dengue virus", FEBS J. (2006); 273(1):34-46.

Bluemel et al., "Epitope distance to the target cell membrane and antigen size determine the potency of T cell-mediated lysis by BiTE antibodies specific for a large melanoma surface antigen," Cancer Immunol Immunother 59(8):1197-1209 (2010).

Brown, M. et al. "Tolerance to Single, but not Multiple, Amino Acid Replacements in Antibody VH CDR2," The Journal of Immunology, 1996, 156: 3285-3291.

Broxmeyer, et al., "CD1d expression on and regulation of murine hematopoietic stem and progenitor cells", Blood. Jun. 14, 2012; 119(24): 5731-5741. Prepublished online Apr. 25, 2012.

Canchis et al., "Tissue distribution of the non-polymorphic major histocompatibility complex class I-like molecule, CD1d", Immunology., Dec. 1993;80(4):561-5.

Colman, P. M., "Effects of amino acid sequence changes on antibody-antigen interactions", Res Immunol. Jan. 1994; 145(1): 33-6.

Communication Pursuant to Article 94(3) EPC for European Application No. 15 722 781.0, dated Feb. 7, 2018, 5 pages.

Coscia et al. "Dysfunctional Vγ9Vδ2 T cells are negative prognosticators and markers of dysregulated mevalonate pathway activity in chronic lymphocytic leukemia cells", Blood, (2012); 120(16):3271-3279.

De Bruin, et al., "A Bispecific Nanobody Approach to Leverage the Potent and Widely Applicable Tumor Cytolytic Capacity of Vγ9Vδ2-T Cells" Oncoimmunology, Sep. 11, 2017, pp. 1-38.

De Bruin et al., "Highly specific and potently activating Vγ9Vδ2-T cell specific nanobodies for diagnostic and therapeutic applications" Clinical Immunology, Aug. 2016, pp. 128-138.

De Bruin et al., "Prevention of Vγ9Vδ2 T Cell Activation by a Vγ9Vδ2 TCR Nanobody", J Immunol., Jan. 1, 2017;198(1):308-317.

(56) References Cited

OTHER PUBLICATIONS

De Weerdt et al. "Improving CLL Vγ9Vδ2-T-cell fitness for cellular therapy by ex vivo activation and ibrutinib", Blood, (2018); 132(21):2260-2272.

Dickopf, S., et al., "Format and geometries matter: Structure-based design defines the functionality of bispecific Antibodies," Computational and Structural Biotechnology Journal (2020) 18:1221-1227.

Dondelinger et al., "Understanding the Significance and Implications of Antibody Numbering and Antigen-Binding Surface/Residue Definition," Frontiers in Immunology, Oct. 2018, 9: 2278, 15 pages.

Edwards, B.M. et al., "The Remarkable Flexibility of the Human Antibody Repertoire; Isolation of Over One Thousand Different Antibodies to a Single Protein, BLyS," Journal of Molecular Biology, Nov. 14, 2003, 334(1), pp. 103-118.

Ferrini et al., "Re-targeting of human lymphocytes expressing the T-cell receptor gamma/delta to ovarian carcinoma cells by the use of bispecific monoclonal antibodies", Int. J. Cancer: 44, 245-250 (1989).

Ferrini et al., "Monoclonal antibodies which react with the T cell receptor y/o recognize different subsets of CD3+WT31-T lymphocytes", Eur. J. Immunol. 1989. 19:57-61.

Gertner-Dardenne Julie et al: "Human V[gamma]9V[delta]2 T cells specifically recognize and kill acute myeloid leukemic blasts", Journal of Immunology, (2012); 188(9):4701-4708.

Guo et al., "Innate anti-breast cancer immunity of apoptosis-resistant human gammadelta-T cells", Breast Cancer Res Treat., Sep. 2005;93(2):169-75. doi: 10.1007/s10549-005-4792-8.

Harlow et al., "Antibody Response", Chapter 4, and "Immunizations", Chapter 5, Antibodies, A Laboratory Manual, Cold Spring Harbor Laboratory, 1988, pp. 37-47, 55-59.

Hoeres et al., "Improving the Efficiency of Vγ9Vδ2 T-Cell Immunotherapy in Cancer", Front Immunol., Apr. 19, 2018;9:800. doi: 10.3389/fimmu.2018.00800. eCollection 2018.

International Search Report and Written Opinion for International Application No. PCT/NL2016/050064, mailed May 27, 2016, 14 pages.

International Search Report and Written Opinion for International Application No. PCT/NL2019/050624, mailed Jan. 31, 2020, 18 pages.

International Search Report and Written Opinion for International Application No. PCT/NL2019/050625, mailed Apr. 2, 2020, 18 pages.

International Search Report issued to International Application No. PCT/NL2015/050235, mailed Jul. 10, 2015.

Kawano et al., "CD1d-restricted and TCR-mediated activation of valpha14 NKT cells by glycosylceramides", Science., Nov. 28, 1997;278(5343): 1626-9. doi: 10.1126/science.278.5343.1626.

Lameris et al. "A single-domain bispecific antibody targeting CD1d and the Nkt T-cell receptor induces a potent antitumor response", Nature Cancer, (2020); 1(11):1054-1065.

Lameris, et al., "Exploiting the CD1d-iNKT cell axis for potentiation of DC-based cancer vaccines", Methods Mol Biol., 2014; 1139:155-65.

Lameris et al. "Generation and characterization of CD1d-specific single-domain antibodies with distinct functional features", Immunology, (2016); 149(1):111-121.

Langerak, et al., "Immunophenotypic and immunogenotypic characteristics of TCRyo+ T cell acute lymphoblastic leukemia", Leukemia (1999); 13, 206-214.

Li, X., et al., ATRA Upregulates Cell Surface CD1D on Myeloma Cells and Sensitizes Them to iNKT Cell-Mediated Lysis, Blood, 2014, vol. 124, No. 21.

Lloyd, C., et al., "Modelling the human immune response: performance of a 1011 human antibody repertoire against a broad panel of therapeutically relevant antigens", Protein Engineering, Design and Selection, Mar. 2009, 22(3), pp. 159-168.

Ma et al.,"CD1d blockade suppresses the capacity of immature dendritic cells to prime allogeneic T cell response", Journal of Surgical Research, pp. 894-899, vol. 1. 183, No. 2 (Feb. 2013).

McVay et al., "Generation of human gammadelta T-cell repertoires", Critical Reviews in Immunology, Jan. 1, 1999, 19(5-6):431-460.

Metelitsa et al., "Expression of CDId by myelomonocytic leukemia provides a target for cytotoxic NKT cells",Leukemia, (2003); 17:1068-1077.

Miossec et al., "Further analysis of the T cell receptor gamma/delta+ peripheral lymphocyte subset. The V delta 1 gene segment is expressed with either C alpha or C delta", J. Exp. Med., vol. 171, Apr. 1990, 1171-1188.

Monzon-Casanov et al., "CD1d Expression in Paneth Cells and Rat Exocrine Pancreas Revealed by Novel Monoclonal Antibodies Which Differentially Affect NKT Cell Activation", PLOS One, pp. e1308, vol. 5, No. 9, (Sep. 2010), ___15 pages.

Muyldermans, S. (2013) "Nanobodies: Natural Single-Domain Antibodies". Annu Rev Biochem, 82:775-797.

Muyldermans, S., "Single domain camel antibodies: current status," Rev. Mol. Biotechnol. 74:277-302, 2001.

Nambiar et al., "Potent neutralizing anti-CD1d antibody reduces lung cytokine release in primate asthma model", mAbs, 2015. 7(3): 638-650.

Oberg et al., "Novel Bispecific Antibodies Increase yo T-Cell Cytotoxicity against Pancreatic Cancer Cells", Cancer Res; 74(5); 1349-60, 2014.

Renukaradhya G J et al: "Type I NKT cells protect (and type II NKT cells suppress) the host's innate antitumor immune response to a B-cell lymphoma", Blood, (2008); 111(12):5637-5645.

Roda-Navarro, et al., "Understanding the Spatial Topology of Artificial Immunological Synapses Assembled in T Cell-Redirecting Strategies: A Major Issue in Cancer Immunotherapy", Front Cell Dev Biol., Jan. 10, 2020;7:370. doi: 10.3389/fcell.2019.00370. eCollection 2019.

Roovers et al., "Efficient inhibition of EGFR signaling and of tumour growth by antagonistic anti-EFGR Nanobodies," Cancer Immunol Immunother, Mar. 2007; 56(3): 303-17.

Rossjohn et al., "Recognition of CD1d-restricted antigens by natural killer T cells", Nat Rev Immunol., Dec. 2012;12(12):845-57.

Rudikoff, S., et al., "Single amino acid substitution altering antigen-binding specificity", Proceedings of the National Academy of Sciences (1982); 79(6): 1979-1983.

Saerens et al., "Identification of a Universal VHH Framework to Graft Non-canonical Antigen-binding Loops of Camel Single-domain Antibodies", J. Mol. Biol. (2005) 352, 597-607.

Siontorou et al., "Nanobodies as novel agents for disease diagnosis and therapy", International Journal of Nanomedicine, p. 4215 (Nov. 2013).

Smolarek et al., Variable fragments of heavy chain antibodies (VHHs): a new magic bullet molecule of medicine ?*, Postepy Hig Med Dosw (online), 2012; 66: 348-358.

Spanoudakis et al., "Regulation of multiple myeloma survival and progression by CD1d", Blood Mar. 12, 2009; 113(11): 2498-2507. Epub Dec. 3, 2008.

Szereday, L. et al., "γ/δ T cell subsets in patients with active *Mycobacterium tuberculosis* infection and tuberculin anergy", Clin Exp Immunol, Feb. 2003; 131(2): 287-291.

Tamura, M. et al., "Structural correlates of an anticarcinoma antibody: identification of specificity-determining residues (SDRs) and development of a minimally immunogenic antibody variant by retention of SDRs only," J. Immunol., 2000, vol. 164, No. 3, pp. 1432-1441.

Teng et al., "CD1d Activation and Blockade: A New Antitumor Strategy", J Immunol., 182(6):3366-3371 (2009).

Uldrich, et al. "CD1d-lipid antigen recognition by the γδ TCR", Nat Immunol., Nov. 2013; 14(11):1137-45. doi: 10.1038/ni.2713. Epub Sep. 29, 2013.

Vajdos et al., "Comprehensive Functional Maps of the Antigen-binding Site of an Anti-ErbB2 Antibody Obtained with Shotgun Scanning Mutagenesis," J Mol Biol, Jul. 5, 2002; 320(2): 415-28.

Vecchi et al., "Increased Jejunal Intraepithelial Lymphocytes Bearing y/o T-Cell Receptor in Dermatitis Herpetiformis", Gastroenterology, 1992; 102: 1499-1505.

(56) References Cited

OTHER PUBLICATIONS

Viale et al., "TCR gamma/delta positive lymphocytes after allogeneic bone marrow transplantation", Bone Marrow Transplantation 1992, 10:249-253.

Vincke, C. et al., "General strategy to humanize a camelid single-domain antibody and identification of a universal humanized nanobody scaffold", J Biol Chem. (2009); 284(5):3273-3284.

Vincke et al., "Introduction to Heavy Chain Antibodies and Derived Nanobodies", Methods in Molecular Biology, pp. 15-26, vol. 911 (Jul. 2012).

White et al., "Antibodies to C0D1d enhance thymic expression of invariant NKT TCR and increase the presence of NOD thymic invariant NKT cells", Developmental and Comparative Immunology, pp. 943-956, vol. 32, No. 8, (Jan. 2008).

Winkler, K., et al., "Changing the antigen binding specificity by single point mutations of an anti-p24 (HIV-1) antibody", The Journal of Immunology (Oct. 15, 2000); 165(8): 4505-4514.

Written Opinion of the International Searching Authority for International Application No. PCT/NL2015/050235, mailed Jul. 10, 2015.

Wrobel, P., et al., Lysis of a Broad Range of Epithelial Tumour Cells by Human gamma delta T Cells: Involvement of NKG2D ligands and T-cell Receptor-versus NKG2D-dependent Recognition, Scandinavian Journal of Immunology, 2007, 66, 320-328.

Yu et al., "The diverse functions of CD1d-restricted NKT cells and their potential for immunotherapy", pp. 42-55, vol. 100, No. 1 (Aug. 2005).

Yue et al., "CD1d ligation on human monocytes directly signals rapid NF-B activation and production of bioactive IL-12", Proceedings of the National Academy of Sciences, pp. 11811-11816, vol. 102, No. 1 (Aug. 2005).

Yue et al., "Direct CD1d-Mediated Stimulation of APC IL-12 Production and Protective Immune Response to Virus Infection In Vivo", J Immunol., 184(1): 268-276 (2010).

Zabetakis et al., "Contributions of the Complementarity Determining Regions to the Thermal Stability of a Single-Domain Antibody", PLOS One, Oct. 2013, vol. 8, Issue 10, e77678, 1-7.

Zhou et al., "Anti-γδ TCR antibody-expanded γδ T cells: a better choice for the adoptive immunotherapy of lymphoid malignancies", Cellular & Molecular Immunology (2012) 9, 34-44.

PE Anti-human TCR Vδ2 Antibody (BioLegend). 2012, 3 pages, URL at https://www.biolegend.com/fr-ch/products/pe-anti-human-tcr-vdelta2-antibody-4571?GroupID=BLG13659.

BISPECIFIC ANTIBODIES FOR USE IN THE TREATMENT OF HEMATOLOGICAL MALIGNANCIES

CROSS-REFERENCE TO RELATED APPLICATIONS

This application is a U.S. National Stage Application under 35 U.S.C. § 371 of International Application No. PCT/NL2019/050625, filed Sep. 19, 2019, which claims the benefit of priority to the Netherlands Patent Application No. 2021664, filed on Sep. 19, 2018, the disclosures of which are hereby incorporated by reference in their entireties for all purposes.

REFERENCE TO AN ELECTRONIC SEQUENCE LISTING

The contents of the electronic sequence listing (LVAT_004_00US_SeqList.txt; Size: 90,125 bytes; and Date of Creation: Mar. 19, 2021) are herein incorporated by reference in its entirety.

FIELD OF THE INVENTION

The present invention relates to the field of immunology, more in particular to the field of antibodies which bind to human CD1d. In particular, the invention relates to the treatment of hematological malignancies using antibodies comprising a first binding moiety that is able to bind human CD1d and a second binding moiety that is able to bind the human Vγ9Vδ2-TCR.

BACKGROUND OF THE INVENTION

In recent years, the therapeutic arsenal for chronic lymphocytic leukemia (CLL) has substantially increased with the introduction of tyrosine kinase inhibitors, Bcl-2 inhibitors and monoclonal antibodies. However, the need for long-term or continuous treatment, resistance and toxicity concerns highlight the need for novel treatment options.

The curative responses observed after allogeneic stem cell transplantation in CLL indicate the therapeutic potential of T cell-based therapies (van Gelder et al. (2017) Bone Marrow Transplant 52:372). Recent attempts to exploit T cell-based therapies in CLL have focused on the development of chimeric antigen receptor (CAR) T cells, in which a diverse, non-antigen specific pool of T cells is endowed with a CAR that recognizes a tumor-associated surface antigen. In contrast to the promising clinical responses observed with CAR T cell therapy in acute lymphoblastic leukemia and diffuse large B cell lymphomas, the response rates and durations in CLL have been disappointing Park et al. (2018) N Engl J Med. 378(5):449-459; Chow et al. (2018) Blood 132(8):777-781). Toxicity is another important concern with CAR T cell therapy, particularly in the elderly CLL population (Brudno et al. (2019) Blood Rev 34:45).

Selective activation of intrinsically tumor-responsive cytotoxic T lymphocytes represents an alternative approach that could generate a potent and focused anti-tumor response. Vγ9Vδ2-T cells form a conserved T cell subset that can induce apoptosis in a wide range of malignant cells in an HLA-independent way (Lo Presti et al. (2017) Front Immunol. 8:1401; de Weerdt et al. (2018) Blood 132(21): 2260-2272; Gertner-Dardenne et al. (2012) J Immunol. 188(9):4701-4708; Kunzmann et al. (2000) Blood 96(2): 384-392). The Vγ9Vδ2-T cell receptor (TCR) recognizes conformational changes in CD277 (BTN3A1) that occur with high levels of phosphoantigens, metabolites generated in inter alia the mevalonate pathway. Phosphoantigens are upregulated during cellular stress, such as infection or malignant transformation, or through pharmacological manipulation with aminobisphosphonates (ABP). In addition, NK receptors allow Vγ9Vδ2-T cells to recognize malignant cells via stress ligands, such as the NKG2D ligands MICA/B and ULBP4. Following activation, Vγ9Vδ2-T cell functions include cytotoxicity, secretion of pro-inflammatory cytokines and antigen presentation (Vantourout et al. (2013) Nat Rev Immunol. 13(2):88-100).

These characteristics have led to clinical trials aiming to exploit the anti-tumor potential of Vγ9Vδ2-T cells, including ABP-based approaches to induce in vivo Vγ9Vδ2-T cell proliferation (Dieli et al. (2007) Cancer Res. 67(15):7450-7457; Wilhelm et al. (2003) Blood 102(1):200-206; Kunzmann et al. (2012) J Immunother. 35(2):205-213). Alternative strategies employed adoptive transfer of ex vivo expanded Vγ9Vδ2-T cells (Abe et al (2009) Exp Hematol. 37(8):956-968; Wilhelm et al. (2014) J Transl Med. 12:45; Kobayashi et al. (2011) Cancer Immunol Immunother. 60(8):1075-1084). With both strategies, objective responses were observed in hematological malignancies, along with a limited toxicity profile, thus establishing the feasibility of Vγ9Vδ2-T cell therapy (Wilhelm et al. (2003) Blood 102 (1):200-206; Kunzmann et al. (2012) J Immunother. 35(2): 205-213; Abe et al (2009) Exp Hematol. 37(8):956-968; Wilhelm et al. (2014) J Transl Med. 12:45). However, these pilot studies demonstrated substantial variability in responses. In summary, although prior studies have demonstrated incidental clinical benefit and safety of Vγ9Vδ2-T cell-based therapy, the observed response rates and durations thereof have so far been unsatisfactory, indicating that novel strategies are needed both for the treatment of CLL as well as for the treatment of other hematological malignancies such as multiple myeloma and acute myeloid leukemia.

SUMMARY OF THE INVENTION

The inventors have now identified CD1d as a suitable target for antibody-based strategies in the majority of a large cohort of 78 CLL patients, particularly in patients with advanced disease. It has furthermore been demonstrated that a CD1d-specific Vγ9Vδ2-T cell engager (a bispecific CD1d/Vγ9Vδ2 antibody) based on single domain antibodies (VHHs) induces robust activation and degranulation of Vγ9Vδ2-T cells. This enables Vγ9Vδ2-T cells from both healthy controls and CLL patients to lyse leukemic cells at favorable effector to target ratios. Moreover, all-trans retinoic acid induces upregulation of CD1d on CLL cells and sensitizes the malignant cells to lysis induced by a bispecific CD1d/Vγ9Vδ2 antibody. Furthermore, evidence is provided that the Vγ9Vδ2-T cell receptor retains its responsiveness to phosphoantigens when the bispecific antibody is bound, and aminobisphosphonates can therefore enhance bispecific antibody mediated-tumor-specific killing. Collectively, the data demonstrate the immunotherapeutic potential of this novel CD1d-specific Vγ9Vδ2-T cell engager in CLL.

Furthermore, the inventors have shown that a bispecific CD1d/Vγ9Vδ2-TCR antibody can induce degranulation of iNKT cells and Vγ9Vδ2-T cells and control growth of other CD1d-expressing tumor cells, including multiple myeloma cells and acute myeloid leukemia cells. Furthermore, in a mouse multiple myeloma model, infusion of both iNKT cells and γδ T cells with a bispecific CD1d/Vγ9Vδ2-TCR antibody significantly prolonged survival compared to a mixture of the iNKT cells and γδ T cells alone without the antibody.

Accordingly, in a first aspect, the invention relates to an antibody comprising a first binding moiety that is able to bind human CD1d and a second binding moiety that is able to bind the human Vγ9Vδ2-TCR for use in the treatment of Chronic Lymphocytic Leukemia (CLL), Multiple Myeloma (MM) or Acute Myeloid Leukemia (AML).

In a further aspect, the invention relates to a method for the treatment of Chronic Lymphocytic Leukemia, Multiple Myeloma or Acute Myeloid Leukemia, comprising administration of an antibody comprising a first binding moiety that is able to bind human CD1d and a second binding moiety that is able to bind the human Vγ9Vδ2-TCR to a human subject in need thereof.

CD1d expression was measured on $CD5^+CD19^+$ lymphocytes from untreated CLL patients and corrected for background fluorescence using fluorescence minus one (FMO) samples. (A) Representative example histogram of CD1d expression on CLL cells. (B) CD1d expression in the total cohort; each bar represents an individual patient (n=78). The dotted lines indicate $CD1d^{neg/dim}$ (relative MFI <50), $CD1d^{low}$ (relative MFI >50 and <150) and $CD1d^{high}$ (relative MFI >150) expression. CD1d expression according to (C) Rai stage (Rai 0: n=25, Rai I-II: n=22, Rai III-IV: n=6) and (D) IgVH-status (M-CLL: n=26, U-CLL: n=21). Bars represent mean. *P<0.05. (C: one-way ANOVA followed by Holm-Sidak's post hoc test; D: unpaired t-test).

Figure 8:
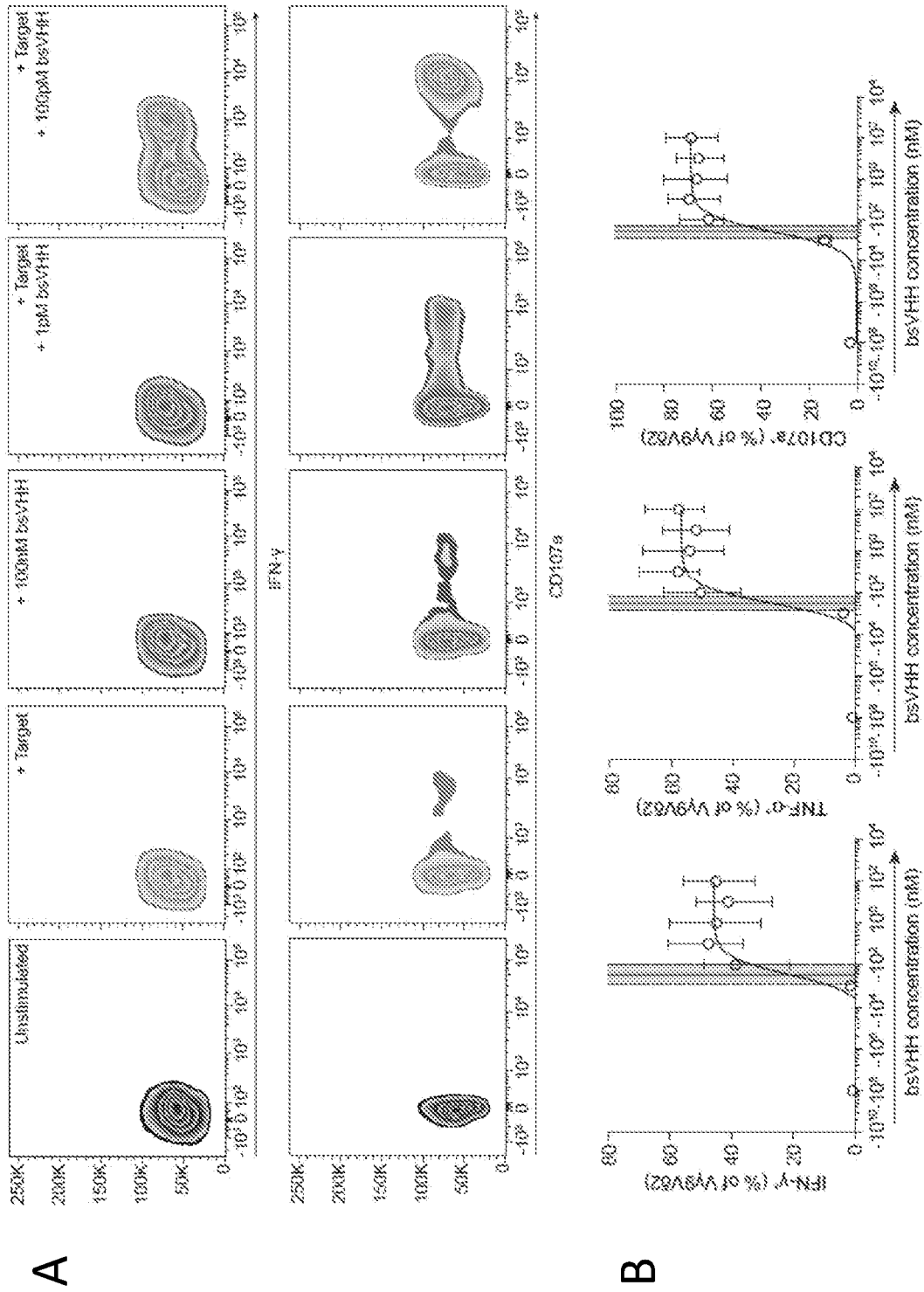

FIG. 8. The Bispecific Anti-CD1d-Vδ2 VHH Activates Vγ9Vδ2-T Cells.

(A, B) Cytokine production and degranulation of Vγ9Vδ2-T cells in the presence of the bispecific antibody 1D7-5C8, brefeldin, monensin and anti-CD107a as measured by flow cytometry. (A) Healthy donor-derived Vγ9Vδ2-T cells were cultured with medium control, Jeko-1 cells (1:1 ratio), bispecific antibody 1D7-5C8 (100 nM), Jeko-1 cells and bispecific antibody 1D7-5C8 (1:1 ratio, 10 pM), or Jeko-1 cells and bispecific antibody 1D7-5C8 (1:1 ratio, 100 pM). Representative plots for 3 experiments. (B) Healthy donor-derived Vγ9Vδ2-T cells were cultured with Jeko-1 cells (1:1 ratio) and the indicated concentrations of bispecific antibody 1D7-5C8 (n=3). (B: non-linear regression analysis). Symbols and error bars represent mean and range; vertical line and shaded area represent EC50 and 95% confidence interval.

Figure 9:
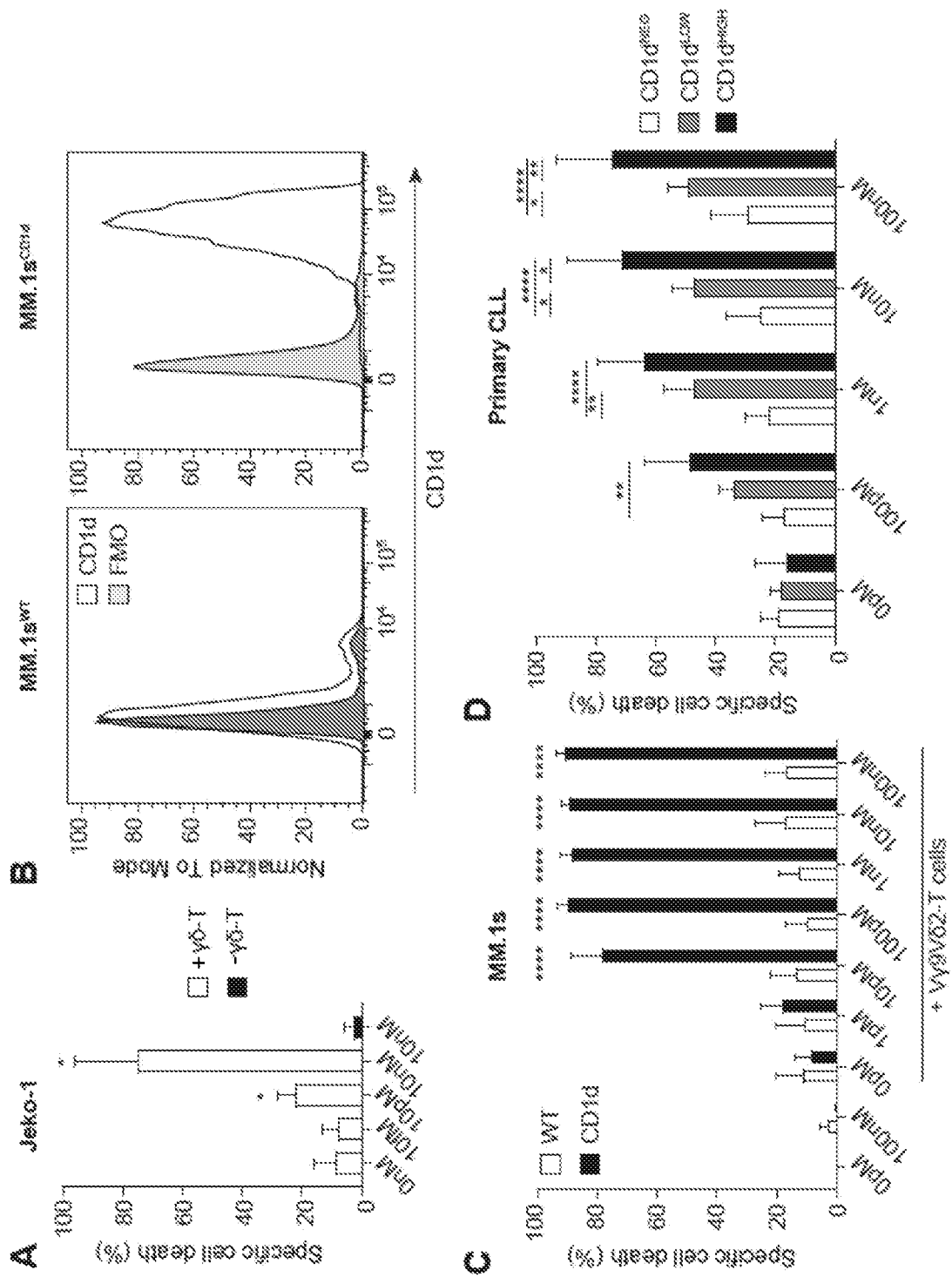

FIG. 9. The Bispecific Anti-CD1d-Vδ2 VHH Induces Lysis of Malignant B Cells.

Lysis of target cells after overnight culture with healthy donor-derived Vγ9Vδ2-T cells in a 1:1 effector to target ratio in the presence of the indicated concentrations of the bispecific antibody 1D7-5C8. (A) Specific lysis of Jeko-1 cell line (n=3). (B) CD1d expression on WT or CD1d-transfected MM.1s cell line (blank histogram: CD1d-stained, grey filled histogram: fluorescence minus one control). (C)

Specific lysis of WT or CD1d-transfected MM.1s cell line (n=4). (D) Specific lysis of primary CLL cells with negative, low or high CD1d expression (n=4 per group). Specific lysis is calculated by correcting for background cell death in condition without Vγ9Vδ2-T cells. Data represent mean and SD. *P<0.05, P<0.01, **P<0.0001. (A: one-way ANOVA followed by Dunnett's post hoc test compared to untreated condition, C: two-way ANOVA followed by Sidak's post hoc test comparing WT vs CD1d for each concentration, D: two-way ANOVA followed by Tukey's post hoc test comparing each CD1d group for each concentration).

Figure 10:
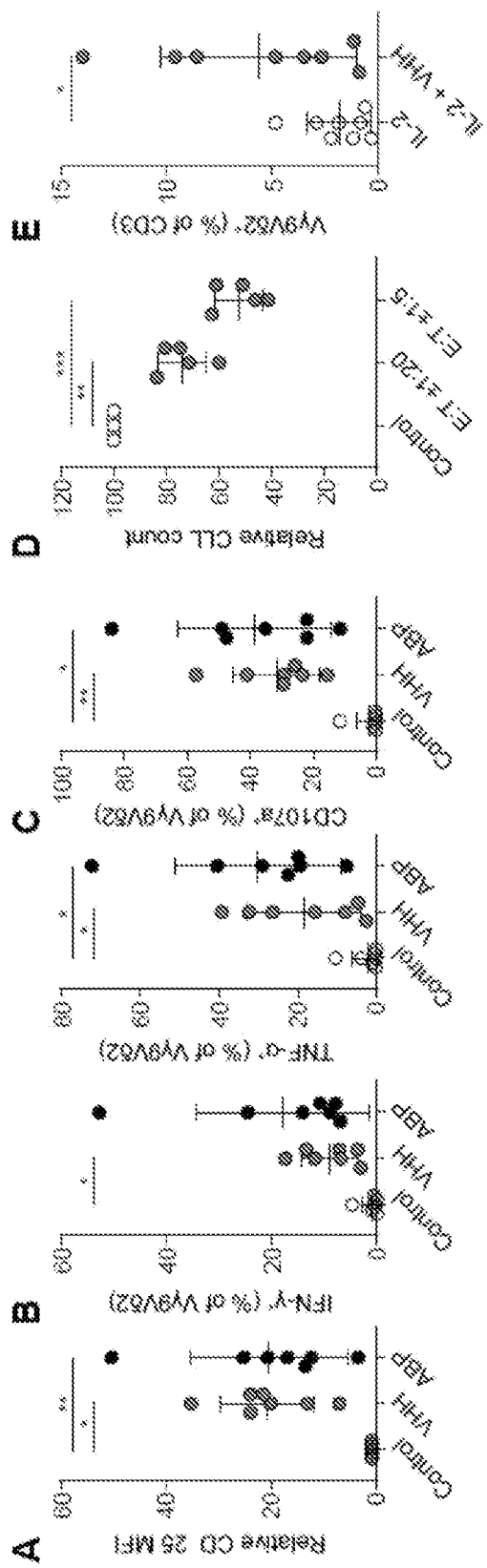

FIG. 10. The Bispecific Anti-CD1d-Vδ2 VHH Activates Vγ9Vδ2-T Cells from CLL Patients and Induces Autologous Tumor Lysis (A-C) Activation of and cytokine production and degranulation by patient-derived Vγ9Vδ2-T cells. PBMCs from CLL patients were enriched for T cells by depletion of CD19$^+$ CLL cells and then cultured overnight with CD19$^+$ CLL cells in a 1:1 ratio with bispecific antibody 1D7-5C8 (50 nM) or medium control in the presence of brefeldin, monensin and anti-CD107a to measure (A) CD25 expression, (B) cytokine production and (C) degranulation by flow cytometry (n=7). (D) Lysis of primary CLL cells by autologous Vγ9Vδ2-T cells. CD3$^+$ cells were isolated from CLL PBMCs and cultured with total CLL PBMCs in a low (5:1 CD3:PBMC, which equals ±1:5 Vδ2:CLL) or higher (20:1 CD3:PBMC, which equals ±1:20 Vδ2:CLL) ratio with bispecific antibody 1D7-5C8 (10 nM) or medium control. Live CLL cells were quantified by flow cytometry using counting beads (n=5). (E) Expansion of patient-derived Vγ9Vδ2-T cells. PBMCs from CLL patients were enriched for T cells by depletion of CD19$^+$ CLL cells and then cultured with CD19$^+$ CLL cells in a 2:1 ratio on irradiated CD40L-expressing fibroblasts with IL-2 (50 IU/mL) or IL-2 and bispecific antibody 1D7-5C8 (50 nM). Percentage Vγ9Vδ2-T cells after 1 week (n=8). Data are presented as mean and SD. *P<0.05, P<0.01, *P<0.001. (A-D: one-way ANOVA followed by Dunnett's post hoc test compared to medium control; E: paired t-test).

Figure 11:
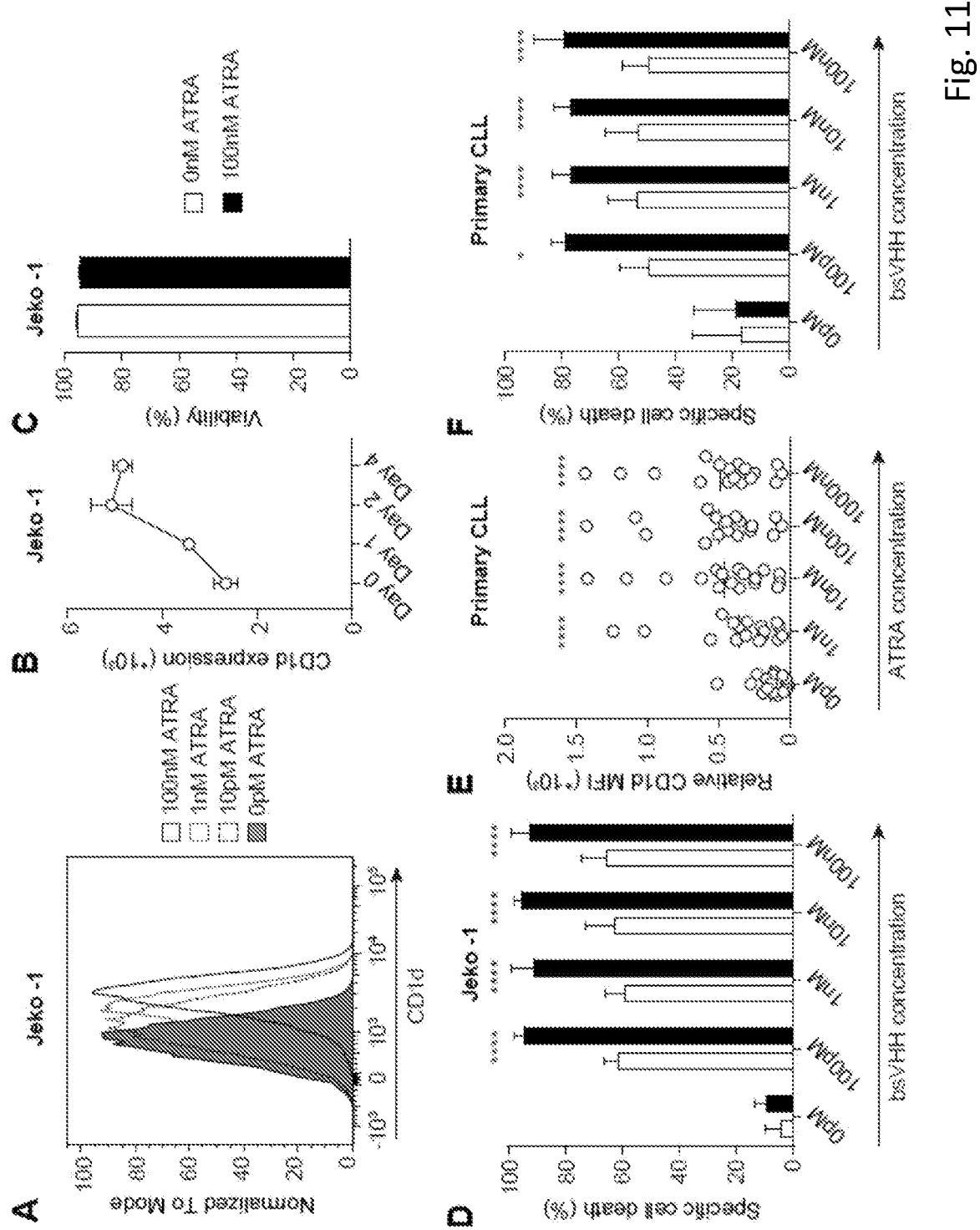

FIG. 11. ATRA Enhances Bispecific Antibody 1D7-5C8-Induced Killing by Upregulation of CD1d Expression (A) CD1d expression on Jeko-1 cells after 48 hours of ATRA treatment. (B) Time-curve of CD1d expression upon ATRA treatment (n=3). (C) Viability of Jeko-1 cells after 48 hours of treatment with 100 nM ATRA (n=4). (D) Lysis of Jeko-1 cells after pretreatment with ATRA. Jeko-1 cells were treated with 100 nM ATRA or medium control for 48 hours and cultured overnight with healthy donor-derived Vγ9Vδ2-T cells in a 1:2 effector to target ratio in the presence of the indicated concentrations of the bispecific antibody 1D7-5C8 (n=4). (E) CD1d expression on primary CLL cells after 48 hours of different concentrations of ATRA or medium control treatment (n=17). (F) Lysis of CLL cells after pretreatment with ATRA. Primary CLL cells were treated with 100 nM ATRA or medium control for 48 hours and cultured overnight with healthy donor-derived Vγ9Vδ2-T cells in a 1:1 effector to target ratio in the presence of the indicated concentrations of the bispecific antibody 1D7-5C8 (n=6). Specific lysis is calculated by correcting for background cell death in condition without Vγ9Vδ2-T cells. Data represent mean and SD. *P<0.05, *P<0.001, **P<0.0001. (C: paired t-test; D, F: two-way ANOVA followed by Sidak's post hoc test comparing control vs ATRA-treated for each concentration; E: Friedman test followed by Dunnett's post hoc test compared to medium control).

Figure 12:
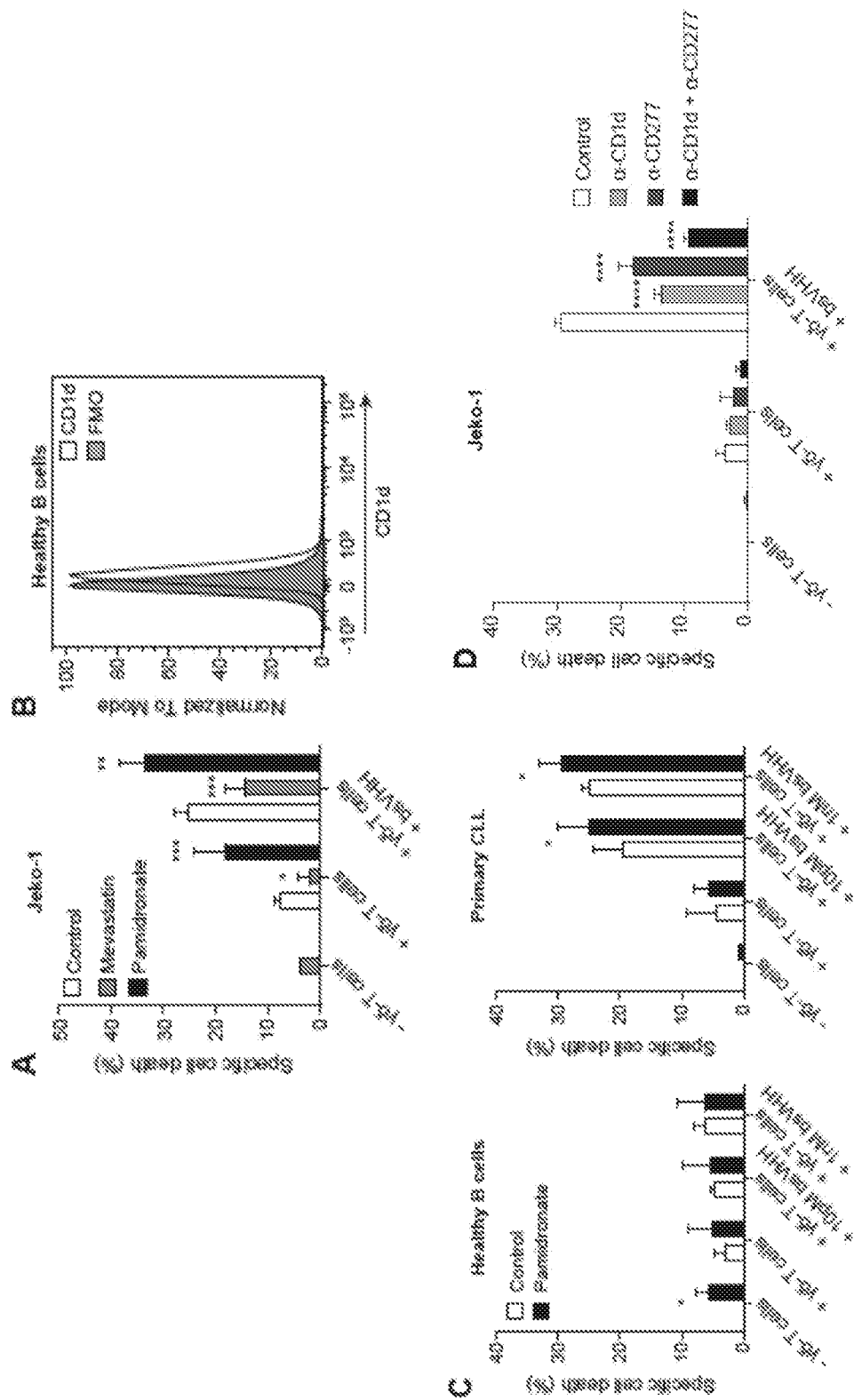

FIG. 12. Vγ9Vδ2-T Cell Activation by the Bispecific Antibody 1D7-5C8 can be Modified Through Modulation ofP-phosphoantigen Recognition (A) Specific lysis of Jeko-1 cells after pretreatment with mevastatin or pamidronate. Jeko-1 cells were treated with 25 μM mevastatin, 50 μM pamidronate or medium control for 2 hours and cultured for 6 hours with healthy donor-derived Vγ9Vδ2-T cells in a 1:2 ratio with 100 nM bispecific antibody 1D7-5C8 (n=3). (B) CD1d expression on B cells from healthy donor PBMCs. (C) Specific lysis of healthy B cells and CLL cells after pretreatment with ABP. Healthy B cells (isolated from healthy donor PBMCs, CFSE-labeled) and CLL cells (isolated from CLL PBMCs, CTV-labeled) were mixed in 1:1 ratio and pretreated with 50 μM pamidronate or medium control for 2 hours. Target cells were then cultured for 6 hours with healthy donor-derived Vγ9Vδ2-T cells in a 1:1:1 (Vγ9Vδ2-T cell: B cell: CLL cell) ratio with the indicated concentrations of bispecific antibody 1D7-5C8 (n=4). (D) Specific lysis of Jeko-1 cells after blockade of CD1d or CD277. Jeko-1 cells were incubated with an anti-CD1d antibody (5 μg/mL), anti-CD277 antibody (10 μg/mL), anti-CD1d and anti-CD277 antibodies, or medium control for 10 minutes. Target cells were then cultured overnight with healthy donor-derived Vγ9Vδ2-T cells in a 1:3 ratio with 10 pM bispecific antibody 1D7-5C8 (n=3). Specific lysis is calculated by correcting for background cell death in condition without Vγ9Vδ2-T cells. Data represent mean and SD. *P<0.05, P<0.01, *P<0.001. (A: two-way ANOVA followed by Dunnett's post hoc test comparing control vs each pretreatment; C: two-way ANOVA followed by Sidak's post hoc test comparing untreated vs ABP pre-treated D: one-way ANOVA followed by Dunnett's post hoc test compared to medium control).

DETAILED DESCRIPTION OF THE INVENTION

Definitions

The term "antibody" as used herein is intended to refer to an immunoglobulin molecule, a fragment of an immunoglobulin molecule, or a derivative of either thereof, which has the ability to specifically bind to an antigen under typical physiological conditions with a half-life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an effector activity). The binding region (or binding domain) which interacts with an antigen, comprises variable regions of both the heavy and light chains of the immunoglobulin molecule. The constant regions of the antibodies (Abs) may mediate the binding of the immunoglobulin to host tissues or factors, including various cells of the immune system (such as effector cells and T cells) and components of the complement system such as C1q, the first component in the classical pathway of complement activation. In some embodiments, however, the Fc region of the antibody has been modified to become inert, "inert" means an Fc region which is at least not able to bind any Fcγ Receptors, induce Fc-mediated cross-linking of FcRs, or induce FcR-mediated cross-linking of target antigens via two Fc regions of individual proteins, such as antibodies. In a further embodiment, the inert Fc region is in addition not able to bind C1q. In one embodiment, the antibody contains mutations at positions 234 and 235 (Canfield and Morrison (1991) J Exp Med 173:1483), e.g. a Leu to Phe mutation at position 234 and a Leu to Glu mutation at position 235. In another embodiment, the antibody contains a Leu to Ala mutation at position 234, a Leu to Ala mutation at position 236 and a Pro to Gly mutation at position 329.

As indicated above, the term antibody as used herein, unless otherwise stated or clearly contradicted by context, includes fragments of an antibody that retain the ability to specifically interact, such as bind, to the antigen. It has been shown that the antigen-binding function of an antibody may be performed by fragments of a full-length antibody. Examples of binding fragments encompassed within the term "antibody" include (i) a Fab' or Fab fragment, a monovalent fragment consisting of the VL, VH, CL and CH1 domains, or a monovalent antibody as described in WO2007059782; (ii) F(ab')2 fragments, bivalent fragments comprising two Fab fragments linked by a disulfide bridge at the hinge region; (iii) a Fd fragment consisting essentially of the VH and CH1 domains; and (iv) a Fv fragment consisting essentially of the VL and VH domains of a single arm of an antibody. Furthermore, although the two domains of the Fv fragment, VL and VH, are coded for by separate genes, they may be joined, using recombinant methods, by a synthetic linker that enables them to be made as a single protein chain in which the VL and VH regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention are discussed further herein. It also should be understood that the term antibody, unless specified otherwise, also includes polyclonal antibodies, monoclonal antibodies (mAbs), chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype.

The term "immunoglobulin heavy chain", "heavy chain of an immunoglobulin" or "heavy chain" as used herein is intended to refer to one of the chains of an immunoglobulin. A heavy chain is typically comprised of a heavy chain variable region (abbreviated herein as VH) and a heavy chain constant region (abbreviated herein as CH) which defines the isotype of the immunoglobulin. The heavy chain constant region typically is comprised of three domains, CH1, CH2, and CH3. The heavy chain constant region may further comprise a hinge region. The term "immunoglobulin" as used herein is intended to refer to a class of structurally related glycoproteins consisting of two pairs of polypeptide chains, one pair of light (L) chains and one pair of heavy (H) chains, all four potentially inter-connected by disulfide bonds. Within the structure of the immunoglobulin (e.g. IgG), the two heavy chains are inter-connected via disulfide bonds in the so-called "hinge region". Equally to the heavy chains each light chain is typically comprised of several regions; a light chain variable region (abbreviated herein as VL) and a light chain constant region (abbreviated herein as CL). The light chain constant region typically is comprised of one domain, CL. Furthermore, the VH and VL regions may be further subdivided into regions of hypervariability (or hypervariable regions which may be hypervariable in sequence and/or form structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4. CDR sequences may be determined by use of various methods, e.g. the methods provided by Choitia and Lesk (1987) J. Mol. Biol. 196:901 or Kabat et al. (1991) Sequence of protein of immunological interest, fifth edition. NIH publication. Various methods for CDR determination and amino acid numbering can be compared on www.abysis.org (UCL).

The term "isotype" as used herein, refers to the immunoglobulin (sub)class (for instance IgG1, IgG2, IgG3, IgG4, IgD, IgA, IgE, or IgM) or any allotype thereof, such as IgG1m(za) and IgG1m(f) [SEQ ID NO:407]) that is encoded by heavy chain constant region genes. Thus, in one embodiment, the antibody comprises a heavy chain of an immunoglobulin of the IgG1 class or any allotype thereof. Further, each heavy chain isotype can be combined with either a kappa (κ) or lambda (λ) light chain.

The term "chimeric antibody" as used herein, refers to an antibody wherein the variable region is derived from a non-human species (e.g. derived from rodents) and the constant region is derived from a different species, such as human. Chimeric antibodies may be generated by antibody engineering. "Antibody engineering" is a generic term used for different kinds of modifications of antibodies, and which is a well-known process for the skilled person. Thus, the chimeric antibody may be a genetically engineered recombinant antibody. Some chimeric antibodies may be both genetically or an enzymatically engineered. It is within the knowledge of the skilled person to generate a chimeric antibody, and thus, generation of a chimeric antibody may be performed by other methods than described herein. Chimeric monoclonal antibodies for therapeutic applications are developed to reduce antibody immunogenicity. They may typically contain non-human (e.g. murine) variable regions, which are specific for the antigen of interest, and human constant antibody heavy and light chain domains. The terms "variable region" or "variable domains" as used in the context of chimeric antibodies, refers to a region which comprises the CDRs and framework regions of both the heavy and light chains of the immunoglobulin.

The term "humanized antibody" as used herein, refers to a genetically engineered non-human antibody, which contains human antibody constant domains and non-human variable domains modified to contain a high level of sequence homology to human variable domains. This can be achieved by grafting of the six non-human antibody complementarity-determining regions (CDRs), which together form the antigen binding site, onto a homologous human acceptor framework region (FR). In order to fully reconstitute the binding affinity and specificity of the parental antibody, the substitution of framework residues from the parental antibody (i.e. the non-human antibody) into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. Optionally, additional amino acid modifications, which are not necessarily back-mutations, may be applied to obtain a humanized antibody with preferred characteristics, such as affinity and biochemical properties. The amino acid sequence of an antibody of non-human origin is distinct from antibodies of human origin, and therefore a non-human antibody is potentially immunogenic when administered to human patients. However, despite the non-human origin of the antibody, its CDR segments are responsible for the ability of the antibody to bind to its target antigen and humanization aims to maintain the specificity and binding affinity of the antibody. Thus, humanization of non-human therapeutic antibodies is performed to minimize its immunogenicity in man while such humanized antibodies at the same time maintain the specificity and binding affinity of the antibody of non-human origin.

The term "multispecific antibody" refers to an antibody having specificities for at least two different, such as at least three, typically non-overlapping, epitopes. Such epitopes may be on the same or different targets. If the epitopes are on different targets, such targets may be on the same cell or different cells or cell types.

The term "bispecific antibody" refers to an antibody having specificities for at least two different, typically non-overlapping, epitopes. Such epitopes may be on the same or different targets. If the epitopes are on different targets, such targets may be on the same cell or different cells or cell types. In one embodiment, the bispecific antibody comprises a first and a second heavy chain.

Examples of bispecific antibody molecules which may be used in the present invention comprise (i) a single antibody that has two arms comprising different antigen-binding regions, (ii) a single chain antibody that has specificity to two different epitopes, e.g., via two scFvs linked in tandem by an extra peptide linker; (iii) a dual-variable-domain antibody (DVD-Ig™), where each light chain and heavy chain contains two variable domains in tandem through a short peptide linkage; (iv) a chemically-linked bispecific (Fab')2 fragment; (v) a TandAb®, which is a fusion of two single chain diabodies resulting in a tetravalent bispecific antibody that has two binding sites for each of the target antigens; (vi) a flexibody, which is a combination of scFvs with a diabody resulting in a multivalent molecule; (vii) a so called "dock and lock" molecule (Dock-and-Lock®), based on the "dimerization and docking domain" in Protein Kinase A, which, when applied to Fabs, can yield a trivalent bispecific binding protein consisting of two identical Fab fragments linked to a different Fab fragment; (viii) a so-called Scorpion molecule, comprising, e.g., two scFvs fused to both termini of a human Fab-arm; and (ix) a diabody.

Examples of different classes of bispecific antibodies include but are not limited to (i) IgG-like molecules with complementary CH3 domains to force heterodimerization; (ii) recombinant IgG-like dual targeting molecules, wherein the two sides of the molecule each contain the Fab fragment or part of the Fab fragment of at least two different antibodies; (iii) IgG fusion molecules, wherein full length IgG antibodies are fused to extra Fab fragment or parts of Fab fragment; (iv) Fc fusion molecules, wherein single chain Fv molecules or stabilized diabodies are fused to heavy-chain constant-domains, Fc-regions or parts thereof; (v) Fab fusion molecules, wherein different Fab-fragments are fused together, fused to heavy-chain constant-domains, Fc-regions or parts thereof; and (vi) ScFv, diabody-based and heavy chain antibodies (e.g., domain antibodies, Nanobodies®) wherein different single chain Fv molecules or different diabodies or different heavy-chain antibodies (e.g. domain antibodies, Nanobodies®) are fused to each other or to another protein or carrier molecule fused to heavy-chain constant-domains, Fc-regions or parts thereof.

Examples of IgG-like molecules with complementary CH3 domain molecules include but are not limited to the Triomab® (Trion Pharma/Fresenius Biotech), the Knobs-into-Holes (Genentech), CrossMAbs (Roche) and the electrostatically-matched (Amgen, Chugai, Oncomed), the LUZ-Y (Genentech, Wranik et al. J. Biol. Chem. 2012, 287(52): 43331-9, doi: 10.1074/jbc.M112.397869. Epub 2012 Nov. 1), DIG-body and PIG-body (Pharmabcine, WO2010134666, WO2014081202), the Strand Exchange Engineered Domain body (SEEDbody) (EMD Serono), the Biclonics (Merus, WO2013157953), FcΔdp (Regeneron), bispecific IgG1 and IgG2 (Pfizer/Rinat), Azymetric scaffold (Zymeworks/Merck), mAb-Fv (Xencor), bivalent bispecific antibodies (Roche, WO2009080254) and DuoBody molecules (Genmab).

Examples of recombinant IgG-like dual targeting molecules include but are not limited to Dual Targeting (DT)-Ig (GSK/Domantis, WO2009058383), Two-in-one Antibody (Genentech, Bostrom, et al 2009. Science 323, 1610-1614), Cross-linked Mabs (Karmanos Cancer Center), mAb2 (F-Star), Zybodies™ (Zyngenia, LaFleur et al. MAbs. 2013 March-April; 5(2):208-18), approaches with common light chain, κλBodies (NovImmune, WO2012023053) and CovX-body® (CovX/Pfizer, Doppalapudi, V. R., et al 2007. Bioorg. Med. Chem. Lett. 17,501-506).

Examples of IgG fusion molecules include but are not limited to Dual Variable Domain (DVD)-IgTM (Abbott), Dual domain double head antibodies (Unilever; Sanofi Aventis), IgG-like Bispecific (ImClone/Eli Lilly, Lewis et al. Nat Biotechnol. 2014 February; 32(2):191-8), Ts2Ab (MedImmune/AZ, Dimasi et al. J Mol Biol. 2009 Oct. 30; 393(3):672-92) and BsAb (Zymogenetics, WO2010111625), HERCULES (Biogen Idec), scFv fusion (Novartis), scFv fusion (Changzhou Adam Biotech Inc) and TvAb (Roche).

Examples of Fc fusion molecules include but are not limited to ScFv/Fc Fusions (Academic Institution, Pearce et al Biochem Mol Biol Int. 1997 September; 42(6):1179), SCORPION (Emergent BioSolutions/Trubion, Blankenship J W, et al. AACR 100th Annual meeting 2009 (Abstract #5465); Zymogenetics/BMS, WO2010111625), Dual Affinity Retargeting Technology (Fc-DARTTM) (MacroGenics) and Dual(ScFv)2-Fab (National Research Center for Antibody Medicine—China).

Examples of Fab fusion bispecific antibodies include but are not limited to F(ab)2 (Medarex/AMGEN), Dual-Action or Bis-Fab (Genentech), Dock-and-Lock® (DNL) (ImmunoMedics), Bivalent Bispecific (Biotecnol) and Fab-Fv (UCB-Celltech).

Examples of ScFv-, diabody-based and domain antibodies include but are not limited to Bispecific T Cell Engager (BiTE®) (Micromet, Tandem Diabody (Tandab) (Affimed), Dual Affinity Retargeting Technology (DARTTM) (MacroGenics), Single-chain Diabody (Academic, Lawrence FEBS Lett. 1998 Apr. 3; 425(3):479-84), TCR-like Antibodies (AIT, ReceptorLogics), Human Serum Albumin ScFv Fusion (Merrimack, WO2010059315) and COMBODY molecules (Epigen Biotech, Zhu et al. Immunol Cell Biol. 2010 August; 88(6):667-75), dual targeting nanobodies®

(Ablynx, Hmila et al., FASEB J. 2010), dual targeting heavy chain only domain antibodies.

A "binding moiety" in the context of the present invention is an antibody moiety, that is capable of specifically binding to a target. A binding moiety may, e.g., comprise: an intact immunoglobulin molecule such as a monoclonal antibody. Alternatively, the binding moiety can comprise an antigen-binding functional fragment, including, but not limited to, Fab, F(ab'), F(ab')2, Fv, dAb, Fd, a complementarity determining region (CDR) fragment, a single chain antibody (scFv), a divalent single chain antibody, a single chain phage antibody, a bispecific double chain antibody, a triabody, a tetrabody, a single domain antibody (nanobody®), a (poly) peptide containing at least an amino acid sequence that is sufficient to specifically bind to its target, and artificial immunoglobulin fragments, such as plastic antibodies (Hoshino et al (2008) J Am Chem Soc 130(46):15242). In a preferred embodiment, a binding moiety is a single domain antibody. Preferably, a binding moiety of the present invention comprises three heavy chain CDRs.

The term "specifically binds" as used herein, refers to the binding of a binding moiety or antibody to a predetermined antigen or target (e.g. human CD1d) to which binding typically is with an affinity corresponding to a $K_D$ of about $10^{-6}$ M or less, e.g. $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using the antigen as the ligand and the binding moiety or antibody as the analyte, and binds to the predetermined antigen with an affinity corresponding to a $K_D$ that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The degree with which the affinity is lower is dependent on the $K_D$ of the binding moiety or antibody, so that when the $K_D$ of the binding moiety or antibody is very low (that is, the binding moiety or antibody is highly specific), then the degree with which the affinity for the antigen is lower than the affinity for a non-specific antigen may be at least 10,000 fold. The term "$K_D$" (M), as used herein, refers to the dissociation equilibrium constant of a particular interaction between the antigen and the binding moiety or antibody.

In the context of the present invention, "competition" or "able to compete" or "compete" refers to any detectably significant reduction in the propensity for a particular antibody (e.g. a CD1d antibody) to bind a particular binding partner (e.g. CD1d) in the presence of another molecule (e.g. a different CD1d antibody) that binds the binding partner. Typically, competition means an at least about 25 percent reduction, such as an at least about 50 percent, e.g. an at least about 75 percent, such as an at least 90 percent reduction in binding between a CD1d antibody or moiety, caused by the presence of another CD1d antibody or moiety as determined by, e.g., ELISA analysis or flow cytometry using sufficient amounts of the two or more competing antibodies or moieties. Additional methods for determining binding specificity by competitive inhibition may be found in for instance Harlow et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley InterScience N.Y., (1992, 1993), and Muller, Meth. Enzymol. 92, 589-601 (1983)).

As described above, in a main aspect, the invention provides an antibody comprising a first binding moiety that is able to bind human CD1d and a second binding moiety that is able to bind the human Vγ9Vδ2-TCR for use in the treatment of Chronic Lymphocytic Leukemia, Multiple Myeloma or Acute Myeloid Leukemia. The term "binds to a Vγ9Vδ2-TCR" means that the antibody binds Vγ9Vδ2-TCR, but does not exclude that the antibody binds to one of the separate subunits in the absence of the other subunit, i.e. to the Vγ9 chain alone or to the Vδ2 chain alone. For example, as can be seen in Table 2 herein, antibody 5C8 is an antibody that binds the Vγ9Vδ2-TCR, but also binds the Vδ2 chain when the Vδ2 chain is expressed alone.

The term "first" and "second" binding moiety does not refer to their orientation/position in the antibody, i.e. it has no meaning with regard to the N- or C-terminus. The term "first" and "second" only serves to correctly and consistently refer to the two different binding moieties in the claims and the description. In one preferred embodiment, the first binding moiety and the second binding moiety are coupled to each other through one or more amide bond(s), preferably through a linker, more preferably comprising the amino acids GGGGS (SEQ ID NO: 159). Two, non-limiting, examples of antibodies comprising a first and a second binding moiety linked through a peptide linker (GGGGS), are depicted in Table 1 (SEQ ID NO: 160 and SEQ ID NO: 164). In another preferred embodiment, the antibody is a bispecific antibody, such as a full-length bispecific antibody. The term "full-length antibody" when used herein, refers to an antibody which contains all heavy and light chain constant and variable domains corresponding to those that are normally found in a wild-type antibody of that isotype.

With "able to activate Vγ9Vδ2 T cells" in the context of the present invention is meant that Vγ9Vδ2 T cells are activated in the presence of the antibody according to the invention, in particular in the presence of a target cell expressing CD1d. Preferably the activation of the Vγ9Vδ2 T cells is measurable through gene-expression and/or (surface) marker expression (e.g., activation markers, such as CD25, CD69, or CD107a) and/or secretory protein (e.g., cytokines or chemokines) profiles. In a preferred embodiment, the antibody is able to induce activation (e.g. upregulation of CD69 and/or CD25 expression) resulting in degranulation (marked by an increase in CD107a expression; Example 3) and cytokine production (e.g. TNFα, IFNγ) by Vγ9Vδ2 T cells. Preferably activation of Vγ9Vδ2 T cells takes place in vivo, particularly in a human body that has been administered an antibody according to the invention and which human body comprises Vγ9Vδ2 T cells and preferably CD1d+ target cells. Preferably, an antibody of the present invention is able to increase CD107a expression on Vγ9Vδ2 T cells to at least 10%, more preferably at least 20%, more preferably at least 40%, most preferably at least 90%, when used in an assay as described in Example 3, wherein e.g. 10% means that 10% of the total number of cells is positive for CD107a. In another embodiment, the number of cells positive for CD107a is increased 1.5-fold, such as 2-fold, e.g. 5-fold, in the presence of an antibody used in the method of the invention.

Similarly, for iNKT cells, "able to activate" in the context of the present invention means that iNKT cells behave differently in the presence of an antibody for use according to the invention, in particular in the presence of a CD1d molecule, preferably in the presence of a CD1d molecule on a cell surface. Markers, such as CD25 (Example 1), CD69, CD107a (Example 3), or cytokines/chemokines, such as IFNγ (Example 1), TNFα, IL-2, are used to determine whether iNKT cells are activated. Preferably the activation of iNKT cells takes place in vivo, particularly in a human body that has been administered an antibody according to the invention and which human body comprises iNKT cells and preferably CD1d+ target cells. With CD1d+ target cells are meant CD1d+ cells that contribute to disease pathogenicity and not normal CD1d-expressing cells. Preferably an antibody of the present invention is able to increase CD107a expression on iNKT cells to at least 20%, more preferably to at least 30%, most preferably to at least 40%, when used in an assay as described in Example 3, wherein e.g. 10% means that 10% of the total number of cells is positive for CD107a. In another embodiment, the number of cells positive for CD107a is increased 1.5-fold, such as 2-fold, e.g. 5-fold, in the presence of an antibody used in the method of the invention. Furthermore, preferably an antibody used in the present invention is able to increase CD25 expression on iNKT cells to at least 10 fold, more preferably to at least 20 fold, most preferably to at least 30 fold compared to a "vehicle" control, as measured mean fluorescence intensity by flow cytometry, using allophycocyanin (APC)-conjugated CD25 in a FACS, when used in an assay as described in Example 1. Preferably, an antibody of the present invention is able to increase IFNγ expression by iNKT cells at least 1.5-fold, such as at least 2-fold or at least 3-fold, when used in an assay as described in Example 1.

Further Aspects and Embodiments of the Invention

As described above, in a first main aspect, the invention provides an antibody comprising a first binding moiety that is able to bind human CD1d and a second binding moiety that is able to bind the human Vγ9Vδ2-TCR for use in the treatment of Chronic Lymphocytic Leukemia, Multiple Myeloma or Acute Myeloid Leukemia.

The antibody used in the invention is thus a multispecific antibody. The antibody may be bispecific or comprise even further binding moieties capable of binding an antigen. Several antibodies that are able to bind human CD1d have been described in WO2016122320. These antibodies are, non-limiting, examples of the sequences that may be used in as first binding moiety in the antibody used in the invention. These antibodies, VHH 1-VHH 21, are depicted in Table 1.

The second binding moiety is able to bind to a Vγ9Vδ2-TCR, preferably to the Vδ2 chain. Several such antibodies, which bind to the Vδ2 chain or the Vγ9 chain of the TCR have been described in WO2015156673 and are depicted in Table 1 and Table 2.

TABLE 1

Designation of VHH (CDR), TCR chains, and sequences of the various VHHs comprised within an antibody used in the invention.

| SEQ ID. | code | Description | Sequence |
|---|---|---|---|
| 1 | VHH 1 | CDR1 | SYTMG |
| 2 | VHH 1 | CDR2 | AIRWSGESPYYADSVKG |
| 3 | VHH 1 | CDR3 | RLVPPGIPIERSLENMNY |
| 4 | VHH 2 | CDR1 | SYTMG |
| 5 | VHH 2 | CDR2 | VIRWSGESPYYADSVKG |
| 6 | VHH 2 | CDR3 | RLVPPGIPIERTLESMNY |
| 7 | VHH 3 | CDR1 | SYTMG |
| 8 | VHH 3 | CDR2 | AIRWSGESPIYADSVKG |
| 9 | VHH 3 | CDR3 | RLVPPGIPIERTLESMRY |
| 10 | VHH 4 | CDR1 | SYTMG |
| 11 | VHH 4 | CDR2 | AIRWSGESPYYADSVKG |
| 12 | VHH 4 | CDR3 | RLVPPGIPIERTLESMKD |
| 13 | VHH 5 | CDR1 | SYTMG |
| 14 | VHH 5 | CDR2 | GIRWSDESPIYADSVKG |
| 15 | VHH 5 | CDR3 | RLVPPGIPIPRTSESMRY |
| 16 | VHH 6 | CDR1 | SYTMA |
| 17 | VHH 6 | CDR2 | AIRWSGESPIYADSVKG |
| 18 | VHH 6 | CDR3 | RLVPPGIPIERTLESMRY |
| 19 | VHH 7 (1D7) | CDR1 | SYTMG |
| 20 | VHH 7 (1D7) | CDR2 | GIRWDDENPYYADSVKG |

TABLE 1-continued

Designation of VHH (CDR), TCR chains, and sequences of the various VHHs comprised within an antibody used in the invention.

| SEQ ID. | code | Description | Sequence |
|---|---|---|---|
| 21 | VHH 7 (1D7) | CDR3 | RLVPPGIPFERTLENMRY |
| 22 | VHH 8 | CDR1 | SYTMG |
| 23 | VHH 8 | CDR2 | AIRWDGESPIYAESVKG |
| 24 | VHH 8 | CDR3 | RLVPPGIPIERTLESMRY |
| 25 | VHH 9 | CDR1 | SYTMG |
| 26 | VHH 9 | CDR2 | VIRWSGESPYYADSVKG |
| 27 | VHH 9 | CDR3 | RLVPPGIPIERTLESMNY |
| 28 | VHH 10 | CDR1 | SYTMG |
| 29 | VHH 10 | CDR2 | AIRWSDESPIYAGSVKG |
| 30 | VHH 10 | CDR3 | RLVPPGIPIERTLESMRY |
| 31 | VHH 11 | CDR1 | SYTMG |
| 32 | VHH 11 | CDR2 | AIRWSDESPYYSDSVKG |
| 33 | VHH 11 | CDR3 | RLVPPGIPIERTLENMRYS |
| 34 | VHH 12 (1D12) | CDR1 | DNVMG |
| 35 | VHH 12 (1D12) | CDR2 | TIRTGGSTNYADSVKG |
| 36 | VHH 12 (1D12) | CDR3 | TIPVPSTPYDY |
| 37 | VHH 13 | CDR1 | SYTMG |
| 38 | VHH 13 | CDR2 | AIRWSGESPYYADSVKG |
| 39 | VHH 13 | CDR3 | RLVPPGIPIERTLENMNY |
| 40 | VHH 14 | CDR1 | SYTMG |
| 41 | VHH 14 | CDR2 | AIRWSGESPYYADSVKG |
| 42 | VHH 14 | CDR3 | RLVPPGIPIERTLESMNY |
| 43 | VHH 15 | CDR1 | SYTMG |
| 44 | VHH 15 | CDR2 | AIRWSGESPIYADSVKG |
| 45 | VHH 15 | CDR3 | RLVPPGIPIERTLESMKD |
| 46 | VHH 16 | CDR1 | SYTMT |
| 47 | VHH 16 | CDR2 | GIRWSGESPYYADSVKG |
| 48 | VHH 16 | CDR3 | RLVPPGIPIERTLESMRY |
| 49 | VHH 17 | CDR1 | SYTMG |
| 50 | VHH 17 | CDR2 | AIRWSGESPYYGDSVKG |
| 51 | VHH 17 | CDR3 | RLVPPGIPIGRTLESMNN |
| 52 | VHH 18 | CDR1 | SYTMG |
| 53 | VHH 18 | CDR2 | AIRWSGESPYYADSVKG |
| 54 | VHH 18 | CDR3 | RLVPPGIPIERALENMNY |
| 55 | VHH 19 | CDR1 | SYTMG |

TABLE 1-continued

Designation of VHH (CDR), TCR chains, and sequences of the
various VHHs comprised within an antibody used in the invention.

| SEQ ID. | code | Description | Sequence |
|---|---|---|---|
| 56 | VHH 19 | CDR2 | AIRWSDESPIYADSVKG |
| 57 | VHH 19 | CDR3 | RLVPPGIPIERTLESMRY |
| 58 | VHH 20 | CDR1 | SYTMG |
| 59 | VHH 20 | CDR2 | AIRWSGESPYYADSVKG |
| 60 | VHH 20 | CDR3 | RLVPPGIPIERSLENMNY |
| 61 | VHH 21 (1D22) | CDR1 | NAMG |
| 62 | VHH 21 (1D22) | CDR2 | VISSSGSTNYADSVKG |
| 63 | VHH 21 (1D22) | CDR3 | HVAGFDEYNY |
| 64 | VHH 1 | VHH | VQLVESGGGLVQAGGSLRLSCAASGSSFSSYTMGWFRQAPGKEREIVAAIRWSGESPYYADSVKGRFTISRDNAKNTLYLQMNSLKPEDTAVYFCAARLVPPGIPIERSLENMNYWKGTLVTVSS |
| 65 | VHH 2 | VHH | VQLVESGGGSVQAGGSLRLSCAASGRSFSSYTMGWCRQAPGKERECVAVIRWSGESPYYADSVKGRFTISRDNAKNTVYLQMNSLKPEDTAVYYCAARLVPPGIPIERTLESMNYWGKGTLVTVSS |
| 66 | VHH 3 | VHH | QVQLVESGGGLVQAGGSLRLSCAASGSSFSSYTMGWFRQAPGKEREIVAAIRWSGESPIYADSVKGRFTISRDNAKNTLYLQMNSLKPEDTAVYYCAARLVPPGIPIERTLESMRYWGKGTLVTVSS |
| 67 | VHH 4 | VHH | EVQLVESGGGLVQAGGSLGLSCAASGRSFSSYTMGVIRWSGESPYYADSVKGAIRWSGESPYYADSVKGRFTISRDNAKNTLYLQMNNLKPEDTAVYYCAARLVPPGIPIERTLESMKDWGKGTLVTVSS |
| 68 | VHH 5 | VHH | VQLVESGGGLVQAGGSLRLSCAASGSSFSSYTMGAIRWSDESPIYAGSVKGGIRWSDESPIYADSVKGRFTISRDNAKNTLYLQMNSLKPEDTAVYYCAARLVPPGIPIPRTSESMRYWGKGTLVTVSS |
| 69 | VHH 6 | VHH | QVQLVESGGGLVQAGDSLRLSCAASGSSFSSYTMAAIRWSDESPYYSDSVKGAIRWSGESPIYADSVKGRFTISRDNAKNTLYLQMNSLKPEDTAVYNCAARLVPPGIPIERTLESMRYWGKGTLVTVSS |
| 70 | VHH 7 (1D7) | VHH | EVQLVESGGGLVQAGGSLRLSCAASVSSFSSYTMGTIRTGGSTNYADSVKGGIRWDDENPYYADSVKGRFTISRDNAKNTLYLQMNSLKPEDTANYYCAARLVPPGIPFERTLENMRYWGKGTLVTVSS |
| 71 | VHH 8 | VHH | EVQLVESGGGLVQAGGSLRLSCAASGSSFSSYTMGAIRWSGESPYYADSVKGAIRWDGESPIYAESVKGRFTISRDNAKNTLYLQMNSLKPEDTAVYYCAARLVPPGIPIERTLESMRYWGKGTLVTVSS |
| 72 | VHH 9 | VHH | EVQLVESGGGSVQAGGSLRLSCAASGRSFSSYTMGAIRWSGESPYYADSVKGVIRWSGESPYYADSVKGRFTISRDNAKNTVYLQMASLKPDDTAVYYCAARLVPPGIPIERTLESMNYWGKGTLVTVSS |
| 73 | VHH 10 | VHH | QVQLVESGGGLVQAGGSLRLSCAASGSSFSSYTMGAIRWSGESPYYADSVKGAIRWSDESPIYAGSVKGRFTISRDNAKNTLYLQMNSLKPEDTAVYYCAARLVPPGIPIERTLESMRYWGKGTLVTVSS |
| 74 | VHH 11 | VHH | EVQLVESGGGLVQAGGSLRLSCAASGSSFSSYTMGSINNGGSTKYADSVKGAIRWSDESPYYSDSVKGRFTISRDNAKNTLYLQMNSLKPEDTAVYYCSARLVPPGIPIERTLENMRYSGKGTLVTVSS |

TABLE 1-continued

Designation of VHH (CDR), TCR chains, and sequences of the
various VHHs comprised within an antibody used in the invention.

| SEQ ID. | code | Description | Sequence |
|---|---|---|---|
| 75 | VHH 12 (1D12) | VHH | QVQLVESGGGLVQAGGSLRLSCAASGSMFSDNVMGAI RWSGESPYYVDSVKGTIRTGGSTNYADSVKGRFTISRDN AKNTVYLQMNSLKPEDTAVYYCRHTIPVPSTPYDYWGQ GTQVTVSS |
| 76 | VHH 13 | VHH | QVQLVESGGGLVQAGGSLGLSCAASGRSFSSYTMGAIR WSGESPIYADSVKGAIRWSGESPYYADSVKGRFTISRDN AKNTLYLQMNSLKPEDTAVYYCAARLVPPGIPIERTLENM NYWGKGTLVTVSS |
| 77 | VHH 14 | VHH | VQLVESGGGLVQAGGSLRLSCAASGSSFSSYTMGGIRW SGESPYYADSVKGAIRWSGESPYYADSVKGRFTISRDNAK NTLYLQMNSLKPEDTAVYYCAARLVPPGIPIERTLESMNY WGKGTLVTVSS |
| 78 | VHH 15 | VHH | QVQLVESGGGLVQAGGSLRLSCAASGSSFSSYTMGAIR WSGESPYYADSVKGAIRWSGESPIYADSVKGRFTISRDN AKNTLYLQMNSLKPEDTAVYYCAARLVPPGIPIERTLESM KDWGKGTLVTVSS |
| 79 | VHH 16 | VHH | QVQLVESGGGLVQAGGSLRLSCAASGSSFSSYTMTVISSS GSTNYADSVKGGIRWSGESPYYADSVKGRFTISRDNAKN TLYLQMNSLKPEDTAVYYCAARLVPPGIPIERTLESMRYW GKGTLVTVSS |
| 80 | VHH 17 | VHH | VQLVESGGGLVQAGGSLRLSCAASGSSFSSYTMGVIRWS GESPYYADSVKGAIRWSGESPYYGDSVKGRFTISRDNAK NTLYLQMNSLKPEDTAVYYCAARLVPPGIPIGRTLESMN NWGKGTLVTVSS |
| 81 | VHH 18 | VHH | QVQLVESGGGLVQAGGSLRLSCAASGSSFSSYTMGAIR WSDESPIYAGSVKGAIRWSGESPYYADSVKGRFTISRDN AKNTLYLQMHSLKPEDTAVYYCAARLVPPGIPIERALENM NYWGKGTLVTVSS |
| 82 | VHH 19 | VHH | EVQLVESGGGLVQAGGSLRLSCAASGSSFSSYTMGAIRW SDESPYYSDSVKGAIRWSDESPIYADSVKGRFTISRDNAK NTLYLQMHSLKPEDTAFYYCAARLVPPGIPIERTLESMRY WGKGTLVTVSS |
| 83 | VHH 20 | VHH | EVQLVESGGGLVQAGGSLRLSCAASGRSFSSYTMGTIRT GGSTNYADSVKGAIRWSGESPYYADSVKGRFTISRDNAK NTNYLQMNSLKPELTAVYYCAARLVPPGIPIERSLENMNY WGKGTLVTVSS |
| 84 | VHH 21 (1D22) | VHH | QVQLVESGGGLVQAGGSLRLSCAASGSIFSINAMGAIR WSGESPYYADSVKGVISSSGSTNYADSVKGRFTISRDNAK NTAYLQMNSLKVEDTAVYYCAAHVAGFDEYNYWGQGT QVTVSS |
| 85 | 5E3 | CDR1 | SYAMG |
| 86 | 5E3 | CDR2 | AISWSGGTTYYADSVKG |
| 87 | 5E3 | CDR3 | SLDCSGPGCHTAEYDY |
| 88 | 6H1 | CDR1 | EYAMG |
| 89 | 6H1 | CDR2 | AISWTGSKTYYADSVKG |
| 90 | 6H1 | CDR3 | SSDCSGPGCHTEEYDY |
| 91 | 5G3 | CDR1 | SYAMG |
| 92 | 5G3 | CDR2 | AVSWGGSTYYADSVKG |
| 93 | 5G3 | CDR3 | SQDCSGPGCYTNEYDS |
| 94 | 5C1 | CDR1 | NYAMA |
| 95 | 5C1 | CDR2 | AVSWSGGRTYYADSVKG |
| 96 | 5C1 | CDR3 | SLSCSGPGCSLEEYDY |

TABLE 1-continued

Designation of VHH (CDR), TCR chains, and sequences of the various VHHs comprised within an antibody used in the invention.

| SEQ ID. | code | Description | Sequence |
|---|---|---|---|
| 97 | 5D3 | CDR1 | NYAMG |
| 98 | 5D3 | CDR2 | VISWSGGSTYYADSVKG |
| 99 | 5D3 | CDR3 | QFSGASTVVAGTALDYDY |
| 100 | 6E3 | CDR1 | NYGMG |
| 101 | 6E3 | CDR2 | GISWSGGSTDYADSVKG |
| 102 | 6E3 | CDR3 | VFSGAETAYYPSDDYDY |
| 103 | 6H4 | CDR1 | NYGMG |
| 104 | 6H4 | CDR2 | GISWSGGSTDYADSVKG |
| 105 | 6H4 | CDR3 | VFSGAETAYYPSDDYDY |
| 106 | 6C1 | CDR1 | NYGMG |
| 107 | 6C1 | CDR2 | GISWSGGSTDYADSVKG |
| 108 | 6C1 | CDR3 | VFSGAETAYYPSDDYDY |
| 109 | 6H3 | CDR1 | NYGMG |
| 110 | 6H3 | CDR2 | GITWSGGSTHYADLVKG |
| 111 | 6H3 | CDR3 | VFSGAETAYYPSTEYDY |
| 112 | 6G3 | CDR1 | NYGMG |
| 113 | 6G3 | CDR2 | GISWSGGSTYYADSVKG |
| 114 | 6G3 | CDR3 | VFSGAETAQYPSYDYDY |
| 115 | 5C8 | CDR1 | NYAMG |
| 116 | 5C8 | CDR2 | AISWSGGSTSYADSVKG |
| 117 | 5C8 | CDR3 | QFSGADYGFGRLGIRGYEYDY |
| 118 | 5F5 | CDR1 | NYAMG |
| 119 | 5F5 | CDR2 | AISWSGGSTYYADSVKG |
| 120 | 5F5 | CDR3 | MFSGSESQLVVVITNLYEYDY |
| 121 | 6A1 | CDR1 | NYAMG |
| 122 | 6A1 | CDR2 | TISWSGGSTYYADSVKG |
| 123 | 6A1 | CDR3 | AFSGSDYANTKKEVEYDY |
| 124 | 6E4 | CDR1 | DYCIA |
| 125 | 6E4 | CDR2 | CITTSDGSTYYADSVKG |
| 126 | 6E4 | CDR3 | YFGYGCYGGAQDYRAMDY |
| 127 | 5C7 | CDR1 | RYTMG |
| 128 | 5C7 | CDR2 | AISWSGGRTNFAGSVKG |
| 129 | 5C7 | CDR3 | DWLPVPGRESYDY |
| 130 | 5D7 | CDR1 | NYAMG |
| 131 | 5D7 | CDR2 | AISWSGGMTDHADSVKG |
| 132 | 5D7 | CDR3 | AFAGDIPYGSSWYGDPTTYDY |
| 133 | 5B11 | CDR1 | TFSMA |

TABLE 1-continued

Designation of VHH (CDR), TCR chains, and sequences of the various VHHs comprised within an antibody used in the invention.

| SEQ ID. | code | Description | Sequence |
|---|---|---|---|
| 134 | 5B11 | CDR2 | AINWSGGSTRYADSVSD |
| 135 | 5B11 | CDR3 | RRGGIYYSTQNDYDY |
| 136 | 6C4 | CDR1 | DYRMG |
| 137 | 6C4 | CDR2 | TISWSGGLTYYADSVKG |
| 138 | 6C4 | CDR3 | GGGYAGGTYYHPEE |
| 139 | 5E3 | VHH | EVQLVESGGGLVQAGGSLRLSCTASGRTFSSYAMGWFRQAPGKEREFVAAISWSGGTTYYADSVKGRFTISRDNAKNTVSLQMNSLKPEDTAVYFCAASLDCSGPGCHTAEYDYWGQGTQVTVSS |
| 140 | 6H1 | VHH | EVQLVESGGGLVQAGGSLRLSCAATGRTFSEYAMGWFRQAPGKEREFAAAISWTGSKTYYADSVKGRFTISRDNAKNTVYLQMNSLKPEDTAVYYCAASSDCSGPGCHTEEYDYWGQGTQVTVSS |
| 141 | 5G3 | VHH | EVQLVESGGGLVQAGGSLRLSCAASGRTFSSYAMGWFRQAPGKEREFVAAVSWSGGSTYYADSVKGRFTISRDNARNTVYLQMNSLNPEDTAVYYCAASQDCSGPGCYTNEYDSWGQGTQVTVSS |
| 142 | 5C1 | VHH | EVQLVESGGGLVQPGGSLRLSCAASGSIFSNYAMAWFRQAPEKERDFLAAVSWSGGRTYYADSVKGRFTISRDNAKNTVNLQMNSLKPEDTAVYYCAASLSCSGPGCSLEEYDYWGQGTQVTVSS |
| 143 | 5D3 | VHH | EVQLVESGGGLVQAGGSLRLSCAASGRPFSNYAMGWFRQAPGKEREFVTVISWSGGSTYYADSVKGRFTISRDNAKNTVYLQMNSLKPEDTAVYYCAAQFSGASTVVAGTALDYDYWGQGTRVTVSS |
| 144 | 6E3 | VHH | EVQLVESGGGLVQAGGSLRLSCAASGRPFSNYGMGWFRQAPGKKREFVAGISWSGGSTDYADSVKGRLTISRDNAKNTVYLQMNSLKPEDTAVYYCAAVFSGAETAYYPSDDYDYWGQGTQVTVSS |
| 145 | 6H4 | VHH | EVQLVESGGGLVQAGGSLRLSCAASGRPFSNYGMGWFRQAPGKKREFVAGISWSGGSTDYADSVKGRFTISRDNAKNTVYLQMNSLKPEDTAVYYCAAVFSGAETAYYPSDDYDYWGQGTQVIVSS |
| 146 | 6C1 | VHH | EVQLVESGGGLVQAGGSLRLSCAASGRPFSNYGMGWFRQAPGKKRESVAGISWSGGSTDYADSVKGRFTISRDNAKNTVYLQMNSLKPEDTAVYYCAAVFSGAETAYYPSDDYDYWGQGTQVIVSS |
| 147 | 6H3 | VHH | EVQLVESGGGLVQAGGSLRLSCAVSGRPFSNYGMGWFRQAPGKEREFVAGITWSGGSTHYADLVKGRFTISRDNAKNTVHLQMNSLKPEDTAVYYCAAVFSGAETAYYPSTEYDYWGQGTQVIVSS |
| 148 | 6G3 | VHH | EVQLVESGGGLVQAGGSLRLSCAASGRPFNNYGMGWFRQAPGKEREFVAGISWSGGSTYYADSVKGRFTISRDNAKNTVYLQMNSLKPEDTAVYYCAAVFSGAETAQYPSYDYDYWGQGTQVTVSS |
| 149 | 5C8 | VHH | EVQLVESGGGLVQAGGSLRLSCAASGRPFSNYAMGWFRQAPGKEREFVAAISWSGGSTSYADSVKGRFTISRDNAKNTVYLQMNSPKPEDTAIYYCAAQFSGADYGFGRLGIRGYEYDYWGQGTQVTVSS |
| 150 | 5F5 | VHH | EVQLVESGGGLVQAGGSLRLSCAASGRTFSNYAMGWFRQAPGKEREFVAAISWSGGSTYYADSVKGRFTISRDNAKNTVYLQMNSLKPEDTAVYYCAAMFSGSESQLVVVITNLYEYDYWGQGTQVTVSS |

TABLE 1-continued

Designation of VHH (CDR), TCR chains, and sequences of the various VHHs comprised within an antibody used in the invention.

| SEQ ID. | code | Description | Sequence |
|---|---|---|---|
| 151 | 6A1 | VHH | EVQLVESGGGLVQAGGSLRLSCAASGRIFSNYAMGWF RQAPGKEREFVATISWSGGSTYYADSVKGRFTISRDNAK NTVYLQMNSLKPEDTAVYYCAAAFSGSDYANTKKEVEY DYWGQGTQVTVSS |
| 152 | 6E4 | VHH | EVQLVESGGGLVQAGGSLRLSCAASGFTFDDYCIAWFR QAPGKEREPVSCITTSDGSTYYADSVKGRFTISSDNAKNT VYLQMNRLKPEDTAVYYCAAYFGYGCYGGAQDYRAM DYWGKGTLVTVSS |
| 153 | 5C7 | VHH | EVQLVESGGGLVQAGDSLRLSCAASGRTFSRYTMGWFR QAPGKEREFVAAISWSGGRTNFAGSVKGRFTISRDNAK NTVYLQMNSLKPEDTAVYYCAADWLPVPGRESYDYWG QGTQVTVSS |
| 154 | 5D7 | VHH | EVQLVESGGGLVQAGGSLRLSCIASGRTFSNYAMGWFR QAPGKEREFVAAISWSGGMTDHADSVKGRFTISRDNAK NTVYLQMNSLKPEDTAVYYCAAAFAGDIPYGSSWYGDP TTYDYWGQGTQVTVSS |
| 155 | 5B11 | VHH | EVQLVESGGGLVQAGGSLRLSCAASGRTSSTFSMAWFR QAPRKEREFVAAINWSGGSTRYADSVSDRFAISRDNAKN TVYLQMNNLKPEDTAVYYCAARRGGIYYSTQNDYDYWG QGTQVTVSS |
| 156 | 6C4 | VHH | EVQLVESGGGLVQAGGSLRLSCAVSVRTFSDYRMGWFR QAPGKEREFVSTISWSGGLTYYADSVKGRFTISRDNSKNT LYLQMNSLKPEDTAVYYCAAGGGYAGGTYYHPEEWGQ GTQVTVSS |
| 157 | Human Vγ9 chain | TCR | MLSLLHASTLAVLGALCVYGAGHLEQPQISSTKTLSKTAR LECVVSGITISATSVYWYRERPGEVIQFLVSISYDGTVRKE SGIPSGKFEVDRIPETSTSTLTIHNVEKQDIATYYCALWEA QQELGKKIKVFGPGTKLIITDKQLDADVSPKPTIFLPSIAET KLQKAGTYLCLLEKFFPDVIKIHWEEKKSNTILGSQEGNT MKTNDTYMKFSWLTVPEKSLDKEHRCIVRHENNKNGV DQEIIFPPIKTDVITMDPKDNCSKDANDTLLLQLTNTSAY YMYLLLLLKSVVYFAIITCCLLRRTAFCCNGEKS |
| 158 | Human Vδ2 chain | TCR | MQRISSLIHLSLFWAGVMSAIELVPEHQTVPVSIGVPATL RCSMKGEAIGNYYINWYRKTQGNTMTFIYREKDIYGPG FKDNFQGDIDIAKNLAVLKILAPSERDEGSYYCACDTLG MGGEYTDKLIFGKGTRVTVEPRSQPHTKPSVFVMKNGT NVACLVKEFYPKDIRINLVSSKKITEFDPAIVISPSGKYNAV KLGKYEDSNSVTCSVQHDNKTVHSTDFEVKTDSTDHVK PKETENTKQPSKSCHKPKAIVHTEKVNMMSLTVLGLRM LFAKTVAVNFLLTAKLFFL |
| 159 | GS-linker | Linker | GGGGS |
| 160 | 1D12-5C8 | Bispecific antibody | QVQLVESGGGLVQAGGSLRLSCAASGSMFSDNVMGW YRQAPGKQRELVATIRTGGSTNYADSVKGRFTISRDNAK NTVYLQMNSLKPEDTAVYYCRHTIPVPSTPYDYWGQGT QVTVSSGGGGSEVQLVESGGGLVQAGGSLRLSCAASGR PFSNYAMGWFRQAPGKEREFVAAISWSGGSTSYADSV KGRFTISRDNAKNTVYLQMNSPKPEDTAIYYCAAQFSGA DYGFGRLGIRGYEYDYWGQGTQVTVSS |
| 161 | 1D12 var | VHH | EVQLVESGGGLVQAGGSLRLSCAASGSMFSDNVMGW YRQAPGKQRELVATIRTGGSTNYADSVKGRFTISRDNAK NTVYLQMNSLKPEDTAVYYCRHTIPVPSTPYDYWGQGT QVTVSS |
| 162 | 5C8 var 1 | VHH | EVQLLESGGGSVQPGGSLRLSCAASGRPFSNYAMSWFR QAPGKEREFVSAISWSGGSTSYADSVKGRFTISRDNSKN TLYLQMNSLRAEDTAVYYCAAQFSGADYGFGRLGIRGY EYDYWGQGTQVIVSS |
| 163 | 5C8 var 2 | VHH | EVQLLESGGGLVQPGGSLRLSCAASGRPFSNYAMSWFR QAPGKEREFVSAISWSGGSTSYADSVKGRFTISRDNSKN TLYLQMNSLRAEDTAVYYCAAQFSGADYGFGRLGIRGY EYDYWGQGTLVTVSS |

TABLE 1-continued

Designation of VHH (CDR), TCR chains, and sequences of the
various VHHs comprised within an antibody used in the invention.

| SEQ ID. | code | Description | Sequence |
|---|---|---|---|
| 164 | 1D12-5C8 var | Bispecific antibody | EVQLVESGGGLVQAGGSLRLSCAASGSMFSDNVMGW YRQAPGKQRELVATIRTGGSTNYADSVKGRFTISRDNAK NTVYLQMNSLKPEDTAVYYCRHTIPVPSTPYDYWGQGT QVIVSSGGGGSEVOLLESGGGSVQPGGSLRLSCAASGR PFSNYAMSWFRQAPGKEREFVSAISWSGGSTSYADSVK GRFTISRDNSKNTLYLQMNSLRAEDTAVYYCAAQFSGA DYGFGRLGIRGYEYDYWGQGTQVTVSS |
| 165 | 1D7-5C8 | Bispecific antibody | EVQLVESGGGLVQAGGSLRLSCAASVSSFSSYTMGTIRT GGSTNYADSVKGGIRWDDENPYYADSVKGRFTISRDNA KNTLYLQMNSLKPEDTANYYCAARLVPPGIPFERTLENM RYWGKGTLVTVSSGGGGSEVQLVESGGGLVQAGGSLRL SCAASGRPFSNYAMGWFRQAPGKEREFVAAISWSGGS TSYADSVKGRFTISRDNAKNTVYLQMNSPKPEDTAIYYC AAQFSGADYGFGRLGIRGYEYDYWGQGTQVTVSS |

TABLE 2

From WO2015156673: Binding of VHHs to γδ T-cells expressing a Vγ9 or Vδ2 chain (paired with a non Vδ2 or Vγ9 chain respectively), expressing the complete Vγ9Vδ2 TCR, or not expressing any of the Vγ9Vδ2 TCR chains.

| SEQ ID | Ref | Vδ2+ | Vγ9+ | Vγ9Vδ2+ | Vγ9Vδ2− |
|---|---|---|---|---|---|
| 139 | 5E3 | − | ++ | ++ | − |
| 140 | 6H1 | − | ++ | ++ | − |
| 141 | 5G3 | − | ++ | ++ | − |
| 142 | 5C1 | +/− | ++ | ++ | − |
| 143 | 5D3 | ++ | − | ++ | − |
| 144 | 6E3 | ++ | − | ++ | − |
| 145 | 6H4 | ++ | − | ++ | − |
| 146 | 6C1 | ++ | − | ++ | − |
| 147 | 6H3 | ++ | +/− | ++ | − |
| 148 | 6G3 | ++ | − | ++ | − |
| 149 | 5C8 | ++ | − | ++ | − |
| 150 | 5F5 | ++ | − | ++ | − |
| 151 | 6A1 | ++ | − | ++ | − |
| 152 | 6E4 | ++ | − | ++ | − |
| 153 | 5C7 | +/− | − | +/− | − |
| 154 | 5D7 | ++ | − | ++ | − |
| 155 | 5B11 | − | − | + | − |
| 156 | 6C4 | +/− | ++ | ++ | − |

"−" indicates a Mean Fluorescence Index (MFI) below 1.5, "+/−" indicates an MFI of between 1.5 and 4.5, "+" indicates an MFI of between 4.6 and 20 and "++" indicates an MFI above 20.

In one embodiment of the invention, the antibody is for use in combination with a further agent, e.g. a further therapeutic agent. In one embodiment, the antibody is for use in combination with a compound capable of upregulating CD1d expression, such as all-trans retinoic acid (ATRA). The ability of a compound to upregulate CD1d expression may, e.g. be evaluated using the methods described in Li et al. (2014) Blood 124:2201.

In a further embodiment, the antibody is for use in combination with a compound capable of upregulating CD1d expression, such as all-trans retinoic acid, and an EZH2 inhibitor, e.g. tazemetostat. In another embodiment, the antibody is for use in combination with an aminobisphosphonate.

In another embodiment of the invention, the antibody is for use in an elderly patient, such as a patient of above 65 years of age, such as above 70 years of age.

In a further embodiment, the invention relates to a method for the treatment of Chronic Lymphocytic Leukemia (CCL), comprising the steps of:

i) selecting a CD1d+ CLL patient, and
ii) administration of an antibody comprising a first binding moiety that is able to bind human CD1d and a second binding moiety that is able to bind to the human Vγ9Vδ2-TCR to said patient. Selection of a CD1d+ CLL patient may be performed by characterizing CLL cells from said patients using the assay described in the Examples herein.

The antibody may have any antibody format suitable for the indicated uses. However, in a preferred embodiment, the first and/or second binding moiety of the antibody is a single domain antibody. Single domain antibodies (sdAb, also called Nanobody®, or VHH) are well known to the skilled person. Single domain antibodies comprise a single CDR1, a single CDR2 and a single CDR3. Examples of single domain antibodies are variable fragments of heavy chain only antibodies, antibodies that naturally do not comprise light chains, single domain antibodies derived from conventional antibodies, and engineered antibodies. Single domain antibodies may be derived from any species including mouse, human, camel, llama, shark, goat, rabbit, and cow. For example, naturally occurring VHH molecules can be derived from antibodies raised in Camelidae species, for example in camel, dromedary, alpaca and guanaco.

Uke a whole antibody, a single domain antibody is able to bind selectively to a specific antigen. Single domain antibodies may contain only the variable domain of an immunoglobulin chain, i.e. CDR1, CDR2 and CDR3 and framework regions. With a molecular weight of only about 12-15 kDa, single domain antibodies are much smaller than common antibodies (150-160 kDa) which are composed of two heavy chains and two light chains or even Fab fragments (53 kDa), composed of one light chain and part of a heavy chain. The format of a single domain antibody has the advantage of less steric hindering when bound to its target.

In one embodiment, the antibody used in the invention is able to compete with a single domain antibody having a sequence according to any one of SEQ ID NOs: 64-84 in binding to human CD1d, preferably wherein the antibody binds to the same epitope on human CD1d as a single domain antibody having a sequence according to any one of SEQ ID NOs: 64-84. Methods for determining the epitope of an antibody are known in the art.

In another embodiment, the antibody is able to activate iNKT cells. The inventors have shown that antibody 1D12 (VHH 12) is able to activate iNKT cells, irrespective of the presence of an exogenous ligand for iNKT cells, such as α-galactosylceramide. The present invention further provides the insight that CD1d recognition by Vδ1+ T cells can be blocked by such antibodies and that the presence of a second binding moiety in an antibody according to the invention enables the activation of Vδ2+ T cells. Such triple acting antibody, i.e. capable of reducing activation of CD1d-restricted Vδ1+ T cells and activating iNKT cells, and at the same time allowing activation of Vδ2+ T cells, create a micro-environment that is skewed towards a Th1-type anti-tumor response. The reduced activation of Vδ1+ T cells, the activation of iNKT cells, and the activation of Vδ2+ T cells synergize towards a tumor-aggressive micro-environment promoting effective tumor-cell killing.

In another embodiment, the antibody used in the invention is able to reduce Vδ1 T cell activation. Reducing Vδ1 T cell activation in this context means that a Vδ1 T cell is no longer able to recognize its ligand on a CD1d molecule that is bound to an antibody as defined in the invention. Such reduced Vδ1 T cell activation can, e.g., be determined by measuring the expression of activation marker CD69 on Vδ1+ T cells. Lower CD69 expression levels are observed in less activated Vδ1+ T cells, e.g., Jurkat cells as used in Example 2. In particular when used in the context of Vδ1+ tumor cells, blocking means that the presence of the antibody according to the invention has a negative impact on tumor cell growth and/or viability. Preferably, CD69 expression on Jurkat cells is increased less than 5-fold, such as less than 2-fold by an antibody according to the invention, as compared to "vehicle" control when tested in an assay as described in Example 2.

In a further embodiment, the first binding moiety of the antibody comprises:
i) CDR1, CDR2 and CDR3 sequences according to SEQ ID NO: 1, 2 and 3, respectively,
ii) CDR1, CDR2 and CDR3 sequences according to SEQ ID NO: 4, 5 and 6, respectively,
iii) CDR1, CDR2 and CDR3 sequences according to SEQ ID NO: 7, 8 and 9, respectively,
iv) CDR1, CDR2 and CDR3 sequences according to SEQ ID NO: 10, 11 and 12, respectively,
v) CDR1, CDR2 and CDR3 sequences according to SEQ ID NO: 13, 14 and 15, respectively,
vi) CDR1, CDR2 and CDR3 sequences according to SEQ ID NO: 16, 17 and 18, respectively,
vii) CDR1, CDR2 and CDR3 sequences according to SEQ ID NO: 19, 20 and 21, respectively,
viii) CDR1, CDR2 and CDR3 sequences according to SEQ ID NO: 22, 23 and 24, respectively,
ix) CDR1, CDR2 and CDR3 sequences according to SEQ ID NO: 25, 26 and 27, respectively,
x) CDR1, CDR2 and CDR3 sequences according to SEQ ID NO: 28, 29 and 30, respectively,
xi) CDR1, CDR2 and CDR3 sequences according to SEQ ID NO: 31, 32 and 33, respectively,
xii) CDR1, CDR2 and CDR3 sequences according to SEQ ID NO: 34, 35 and 36, respectively,
xiii) CDR1, CDR2 and CDR3 sequences according to SEQ ID NO: 37, 38 and 39, respectively,
xiv) CDR1, CDR2 and CDR3 sequences according to SEQ ID NO: 40, 41 and 42, respectively,
xv) CDR1, CDR2 and CDR3 sequences according to SEQ ID NO: 43, 44 and 45, respectively,
xvi) CDR1, CDR2 and CDR3 sequences according to SEQ ID NO: 46, 47 and 48, respectively,
xvii) CDR1, CDR2 and CDR3 sequences according to SEQ ID NO: 49, 50 and 51, respectively,
xviii) CDR1, CDR2 and CDR3 sequences according to SEQ ID NO: 52, 53 and 54, respectively,
xix) CDR1, CDR2 and CDR3 sequences according to SEQ ID NO: 55, 56 and 57, respectively,
xx) CDR1, CDR2 and CDR3 sequences according to SEQ ID NO: 58, 59 and 60, respectively, or
xxi) CDR1, CDR2 and CDR3 sequences according to SEQ ID NO: 61, 62 and 63, respectively.

CDR1, CDR2 and CDR3 sequences or framework regions may be exchanged between species. For example, from a llama immunoglobulin molecule, CDR sequences may be selected and exchanged with CDR sequences in a human immunoglobulin molecule, to obtain a human immunoglobulin molecule having the specificity that is derived from the llama CDR sequences. This may be advantageous as a human sequence may be less immunogenic to humans as compared to an antibody containing the original llama framework sequence. Such an exchange of sequences is known as humanization. Hence, the immunoglobulin molecules as provided by the invention may have human derived immunoglobulin sequences or immunoglobulin sequences derived from other animals, such as but not limited to: camelid, llama, shark, and have the CDR1, CDR2 and CDR3 sequences replaced with the CDR sequences according to the invention in order to provide for human CD1d binding. In other words, the antibody according to the invention may comprise a humanized single-domain antibody with CDRs as disclosed herein. For example, a single domain antibody may have human framework sequences and CDR regions as disclosed herein.

In a further embodiment, first binding moiety of the antibody comprises any one of the sequences set forth in SEQ ID NOs: 64-84 or 161.

As described, the antibody used in the invention is able to bind the human Vγ9Vδ2-TCR.

In one embodiment, the antibody is able to bind Vγ9, while in another embodiment, the antibody is able to bind Vδ2.

In one embodiment, the antibody is able to compete with a single domain antibody having a sequence according to any one of SEQ ID NOs: 139-156 in binding to the human Vγ9Vδ2-TCR, preferably wherein the antibody binds to the same epitope on the human Vγ9Vδ2-TCR as a single domain antibody having a sequence according to any one of SEQ ID NOs: 139-156.

Thus, further provided is an antibody for use according to the invention, wherein the second binding moiety is able to compete with binding to a Vγ9Vδ2-TCR with single domain antibody 5E3 (SEQ ID NO: 139), 6H1 (SEQ ID NO: 140), 5G3 (SEQ ID NO: 141), 5C1 (SEQ ID NO: 142), 5D3 (SEQ ID NO: 143), 6E3 (SEQ ID NO: 144), 6H4 (SEQ ID NO: 145), 6C1 (SEQ ID NO: 146), 6H3 (SEQ ID NO: 147), 6G3 (SEQ ID NO: 148), 5C8 (SEQ ID NO: 149), 5F5 (SEQ ID NO: 150), 6A1 (SEQ ID NO: 151), 6E4 (SEQ ID NO: 152), 5C7 (SEQ ID NO: 153), 5D7 (SEQ ID NO: 154), 5B11 (SEQ ID NO: 155), or 6C4 (SEQ ID NO: 156). Preferably, the second binding moiety binds to the same epitope sequence as recognized by binding moiety 5E3, 6H1, 5G3, 5C1, 5D3, 6E3, 6H4, 6C1, 6H3, 6G3, 5C8, 5F5, 6A1, 6E4, 5C7, 5D7, 5B11 or 6C4.

In a further embodiment, the second binding moiety comprises:
i) CDR1, CDR2 and CDR3 sequences according to SEQ ID NO: 85, 86 and 87, respectively,
ii) CDR1, CDR2 and CDR3 sequences according to SEQ ID NO: 88, 89 and 90, respectively, iii) CDR1, CDR2 and CDR3 sequences according to SEQ ID NO:91, 92 and 93, respectively,
iv) CDR1, CDR2 and CDR3 sequences according to SEQ ID NO: 94, 95 and 96, respectively,
v) CDR1, CDR2 and CDR3 sequences according to SEQ ID NO: 97, 98 and 99, respectively,
vi) CDR1, CDR2 and CDR3 sequences according to SEQ ID NO:100, 101 and 102, respectively,
vii) CDR1, CDR2 and CDR3 sequences according to SEQ ID NO:103, 104 and 105, respectively,
viii) CDR1, CDR2 and CDR3 sequences according to SEQ ID NO:106, 107 and 108, respectively,
ix) CDR1, CDR2 and CDR3 sequences according to SEQ ID NO:109, 110 and 111, respectively,
x) CDR1, CDR2 and CDR3 sequences according to SEQ ID NO:112, 113 and 114, respectively,
xi) CDR1, CDR2 and CDR3 sequences according to SEQ ID NO:115, 116 and 117, respectively,
xii) CDR1, CDR2 and CDR3 sequences according to SEQ ID NO:118, 119 and 120, respectively,
xiii) CDR1, CDR2 and CDR3 sequences according to SEQ ID NO:121, 122 and 123, respectively,
xiv) CDR1, CDR2 and CDR3 sequences according to SEQ ID NO:124, 125 and 126, respectively,
xv) CDR1, CDR2 and CDR3 sequences according to SEQ ID NO:127, 128 and 129, respectively,
xvi) CDR1, CDR2 and CDR3 sequences according to SEQ ID NO:130, 131 and 132, respectively,
xvii) CDR1, CDR2 and CDR3 sequences according to SEQ ID NO:133, 134 and 135, respectively, or
xviii) CDR1, CDR2 and CDR3 sequences according to SEQ ID NO:136, 137 and 138, respectively.

In a further embodiment, second binding moiety of the antibody comprises any one of the sequences set forth in SEQ ID NOs: 139-156 or 162 or 163. In a further embodiment, the antibody comprises the sequence set forth in SEQ ID NO: 164.

In a further embodiment, the antibody comprises a further tumor targeting moiety. A tumor-targeting moiety comprises a binding moiety that is able to specifically bind to a tumor antigen. Tumor antigens are proteins that are produced by tumor cells that elicit an immune response, particularly T-cell mediated immune responses. The selection of the antigen binding moiety will depend on the particular type of cancer to be treated. Tumor antigens are well known in the art and include, for example a glioma-associated antigen, carcinoembryonic antigen (CEA), EGFRvIII, Interleukin-11 receptor alpha (IL-I IRα), Interleukin-13 receptor subunit alpha-2 (IL-13Ra or CD213A2), epidermal growth factor receptor (EGFR), B7H3 (CD276), Kit (CD117), carbonic anhydrase (CA-IX), CS-1 (also referred to as CD2 subset 1), Mucin 1, cell surface associated (MUC1), BCMA, oncogene fusion protein consisting of breakpoint cluster region (BCR) and Abelson murine leukemia viral oncogene homolog 1 (Abl) bcr-abl, Receptor tyro sine-protein kinase ERBB2 (HER2/neu), β-human chorionic gonadotropin, alphafetoprotein (AFP), anaplastic lymphoma kinase (ALK), CD19, CD123, cyclin BI, lectin-reactive AFP, Fos-related antigen 1, adrenoceptor beta 3 (ADRB3), thyroglobulin, tyrosinase; ephrin type-A receptor 2 (EphA2), Receptor for Advanced Glycation End products (RAGE-1), renal ubiquitous 1 (RU1), renal ubiquitous 2 (RU2), synovial sarcoma, X breakpoint 2 (SSX2), A kinase anchor protein 4 (AKAP-4), lymphocyte-specific protein tyrosine kinase (LCK), proacrosin binding protein sp32 (OY-TES1), Paired box protein Pax-5 (PAX5), Squamous Cell Carcinoma Antigen Recognized By T Cells 3 (SART3), C-type lectin-like molecule-1 (CLL-1 or CLECL1), fucosyl GM1, hexasaccharide portion of globoH glycoceramide (GloboH), MN-CA IX, Epithelial cell adhesion molecule (EPCAM), EVT6-AML, transglutaminase 5 (TGS5), human telomerase reverse transcriptase (hTERT), polysialic acid, placenta-specific 1 (PLAC1), intestinal carboxyl esterase, LewisY antigen, sialyl Lewis adhesion molecule (sLe), lymphocyte antigen 6 complex, locus K 9 (LY6K), heat shock protein 70-2 mutated (mut hsp70-2), M-CSF, v-myc avian, myelocytomatosis viral oncogene neuroblastoma derived homolog (MYCN), Ras Homolog Family Member C (RhoC), Tyrosinase-related protein 2 (TRP-2), Cytochrome P450 1B1 (CYP1B1), CCCTC-Binding Factor (Zinc Finger Protein)-Like (BORIS or Brother of the Regulator of Imprinted Sites), prostase, prostate-specific antigen (PSA), paired box protein Pax-3 (PAX3), prostatic acid phosphatase (PAP), Cancer/testis antigen 1 (NY-ESO-1), Cancer/testis antigen 2 (LAGE-Ia), LMP2, neural cell adhesion molecule (NCAM), tumor protein p53 (p53), p53 mutant, Rat sarcoma (Ras) mutant, glycoprotein 100 (gp100), prostein, OR51E2, pannexin 3 (PANX3), prostate stem cell antigen (PSCA),high molecular weight-melanoma-associated antigen (HMWMAA), Hepatitis A virus cellular receptor 1 (HAVCRI), vascular endothelial growth factor receptor 2 (VEGFR2), Platelet-derived growth factor receptor beta (PDGFR-beta), legumain, human papilloma virus E6 (HPV E6), human papilloma virus E7 (HPV E7), survivin, telomerase, sperm protein 17 (SPA17), Stage-specific embryonic antigen-4 (SSEA-4), tyrosinase, TCR Gamma Alternate Reading Frame Protein (TARP), Wilms tumor protein (WT1), prostate-carcinoma tumor antigen-1 (PCTA-1), melanoma inhibitor of apoptosis (ML-IAP), MAGE, Melanoma-associated antigen 1 (MAGE-AI), melanoma cancer testis antigen-1 (MAD-CT-1), melanoma cancer testis antigen-2 (MAD-CT-2), melanoma antigen recognized by T cells 1 (MelanA/MARTI), X Antigen Family, Member 1A (XAGE1), elongation factor 2 mutated (ELF2M), ERG (TMPRSS2 ETS fusion gene), N-Acetyl glucosaminyl-transferase V (NA17), neutrophil elastase, sarcoma translocation breakpoints, mammary gland differentiation antigen (NY-BR-1), ephrinB2, CD20, CD22, CD24, CD30, CD33, CD38, CD44v6, CD97, CD171, CD179a, androgen receptor, insulin growth factor (IGF)-I, IGF-II, IGF-I receptor, ganglioside GD2 (GD2), o-acetyl-GD2 ganglioside (OAcGD2), ganglioside GD3 (aNeu5Ac(2-8)aNeuSAc(2-3)bDGalp(I-4)bDGlcp(I-I)Cer), ganglioside GM3 (aNeu5Ac(2-3)bDGa3p(I-4)bDGlcp(I-I) Cer), G protein-coupled receptor class C group 5, member D (GPRC5D), G protein-coupled receptor 20 (GPR20), chromosome X open reading frame 61 (CXORF61), folate receptor (FRα), folate receptor beta, Receptor tyrosine kinase-like orphan receptor 1 (ROR1), Fms-Like Tyrosine Kinase 3 (Flt3), Tumor-associated glycoprotein 72 (TAG72), Tn antigen (TN Ag or (GalNAca-Ser/Thr)), angiopoietin-binding cell surface receptor 2 (Tie 2), tumor endothelial marker 1 (TEM1 or CD248), tumor endothelial marker 7-related (TEM7R), claudin 6 (CLDN6), thyroid stimulating hormone receptor (TSHR), uroplakin 2 (UPK2), mesothelin, Protease Serine 21 (Testisin or PRSS21), epidermal growth factor receptor (EGFR), fibroblast activation protein alpha (FAP), Olfactory receptor 51E2 (OR51E2), ETS translocation-variant gene 6, located on chromosome 12p (ETV6-AML), CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); immunoglobulin lambda-like polypeptide 1 (IGLL1); folate receptor (FRα); mesothelin; EGFR variant III (EGFRvIII); B-cell maturation antigen (BCMA); GD2; CLL-1; CA-IX; MUC1; HER2; and any combination thereof. In one preferred embodiment, the tumor antigen is selected from the group consisting of folate receptor (FRα), mesothelin, EGFRvIII, IL-13Ra, CD123, CD19, CD33, BCMA, GD2, CLL-1, CA-IX, MUC1, HER2, and any combination thereof. In one embodiment, the tumor targeting moiety is an immunoglobulin that specifically binds to PD-L1, EGFR, CD40, Her2, MUC-1, CEA, c-met, CD19, CD20, BCMA, Her3, AFP, CAIX, or CD38.

Pharmaceutical Compositions, Dosages, Modes of Administration and Methods of Treatment Polypeptides, such as antibodies may be formulated with pharmaceutically acceptable carriers or diluents as well as any other known adjuvants and excipients in accordance with conventional techniques such as those disclosed in (Rowe et al., Handbook of Pharmaceutical Excipients, 2012 June, ISBN 9780857110275). The pharmaceutically acceptable carriers or diluents as well as any other known adjuvants and excipients should be suitable for the polypeptides or antibodies and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.) upon antigen binding). A pharmaceutical composition may also include diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition. Further pharmaceutically acceptable excipients and carriers include any and all suitable solvents, dispersion media, coatings, antibacterial and antifungal agents, isotonicity agents, antioxidants and absorption-delaying agents, and the like that are physiologically compatible with an antibody of the present invention.

The invention provides methods of treating a disease or disorder comprising administering antibodies as defined herein to a subject in need thereof. In one embodiment, the subject is human. The method of the invention involves administering an effective amount of the antibodies. "Treatment" or "treating" refers to the administration of an effective amount of a therapeutically active polypeptide according to the present invention with the purpose of easing, ameliorating, arresting or eradicating (curing) symptoms or disease states. An "effective amount" or "therapeutically effective amount" refers to an amount effective, at dosages and for periods of time necessary, to achieve a desired therapeutic result. A therapeutically effective amount of a polypeptide, such as an antibody, may vary according to factors such as the disease stage, age, sex, and weight of the individual, and the ability of the antibody to elicit a desired response in the individual. A therapeutically effective amount is also one in which any toxic or detrimental effects of the antibody or antibody portion are outweighed by the therapeutically beneficial effects.

Administration may be carried out by any suitable route, but will typically be parenteral, such as intravenous, intramuscular or subcutaneous. Effective dosages and the dosage regimens for the antibody, depend on the disease or condition to be treated and may be determined by the persons skilled in the art.

Antibodies used in the present invention may also be administered in combination therapy, i.e., combined with other therapeutic agents relevant for the disease or condition to be treated. Accordingly, in one embodiment, the antibody-containing medicament is for combination with one or more further therapeutic agents, such as cytotoxic, chemotherapeutic or anti-angiogenic agents. Such combined administration may be simultaneous, separate or sequential. Thus, in a further embodiment, the present invention provides a method for treating or preventing disease, such as cancer, which method comprises administration to a subject in need thereof of a therapeutically effective amount of an antibody or a pharmaceutical composition of the present invention, in combination with radiotherapy and/or surgery.

Further Aspects and Embodiments of the Invention

In a further aspect, the invention relates to a method for the treatment of Chronic Lymphocytic Leukemia, Multiple Myeloma or Acute Myeloid Leukemia, comprising administration of an antibody comprising a first binding moiety that is able to bind human CD1d and a second binding moiety that is able to bind the human Vγ9Vδ2-TCR to a human subject in need thereof. In one embodiment, said method has any one of the further features of the antibody or use described herein.

Methods of Preparing Antibodies of the Invention

Antibodies used in the invention, such as polypeptides, in particular antibodies, are typically produced recombinantly, i.e. by expression of nucleic acid constructs encoding the polypeptides in suitable host cells, followed by purification of the produced recombinant polypeptide from the cell culture. Nucleic acid constructs can be produced by standard molecular biological techniques well-known in the art. The constructs are typically introduced into the host cell using a vector. Suitable nucleic acid constructs, vectors are known in the art. Host cells suitable for the recombinant expression of polypeptides, such as antibodies are well-known in the art, and include CHO, HEK-293, Expi293F, PER-C6, NS/0 and Sp2/0 cells. Alternatively, expression may be performed in yeast such as *Pichia pastoris, Hansenula polymorpha* or *Saccharomyces cerevisiae* or bacteria.

EXAMPLES

Materials
Cell Lines
The human Epstein-Barr virus-transformed B-lymphoblast cell line C1R, stably transduced with CD1d, and the human cell line JY were grown in Iscove's modified Dulbecco's medium (catalogue no. 12-722F; Lonza, Basel, Switzerland) supplemented with 10% (v/v) fetal calf serum (catalogue no. SV30160.03; HyClone GE Healthcare, Chalfont, St Giles, UK), 0.05 mm β-mercaptoethanol, 100 IU/ml sodium penicillin, 100 µg/ml streptomycin sulphate and 2.0 mm l-glutamine (catalogue no. 10378-016; Life Technologies, Carlsbad, CA). The human cervical adenocarcinoma cell line HeLa, stably transduced with CD1d, was cultured in Dulbecco's modified Eagle's medium (catalogue no.

BE12-709F; Lonza) supplemented with 10% (v/v) fetal calf serum, 0.05 mm β-mercaptoethanol, 100 IU/ml sodium penicillin, 100 μg/ml streptomycin sulphate and 2.0 mm I-glutamine. The human myeloma cell line MM.1s with or without mcherry/luc and, stably transduced with CD1d, the human acute T-lymphoblastic leukemia cell line CCRF-CEM, the human acute T cell leukemia cell line Jurkat transduced with a Vδ1 sulfatide-CD1d restricted TCR, and the human acute myeloid leukemia cell lines MOLM-13 and NOMO-1 were cultured in RPMI-1640 (catalogue no. BE12-115F; Lonza) medium supplemented with 10% (v/v) fetal calf serum, 0.05 mm β-mercaptoethanol, 100 IU/ml sodium penicillin, 100 μg/ml streptomycin sulphate and 2.0 mm I-glutamine. CCRF-CEM and MM.1s genetic characteristics were determined by PCR-single-locus-technology and found identical to the published DNA-profiles. Cells were tested mycoplasma-negative and frequently tested for purity (transfectants) by flow cytometry.

Flow Cytometry and Monoclonal Antibodies

The following antibodies were used in this study: fluorescein isothiocyanate (FITC) conjugated Vδ2, FITC CD69, phycoerythrin (PE) and allophycocyanin (APC)-conjugated CD25 (catalogue nos 555432 and #340907), and APC CD3 were purchased from BD Biosciences (Franklin Lakes, NJ). Phycoerythrin-Cyanine 7-conjugated Vα24 (catalogue no. PN A66907) and Vβ11 PE (catalogue no. IM2290) were purchased from Beckman Coulter (Brea, CA). 7-aminoactinomycin D (7-AAD) was purchased from Sigma (St Louis, MO), PE Vγ9 from Biolegend (San Diego, USA), PE CD107a from Miltenyi (Miltenyi Biotec, Bergisch Gladbach, Germany) and FITC annexin V from VPS Diagnostics (Hoever, the Netherlands) (catalogue no. A700). Tetramers were made in house. Flow cytometry staining was performed in FACS buffer (PBS supplemented with 0.1% BSA and 0.02% sodium azide) for 30 min at 4°, unless otherwise specified. Samples were analyzed on FACS Fortessa (BD Biosciences).

Generation of DC, iNKT and Vγ9Vδ2-T Cell Lines moDC and primary human iNKT and γδ T cells were generated as described previously (De Bruin et al (2016) Clin Immunol 169:128). Briefly, monocytes were isolated from peripheral blood mononuclear cells with the use of CD14 MicroBeads (Miltenyi Biotec, Bergisch Gladbach, Germany) and cultured in complete RPMI-1640 medium in the presence of 1000 U/ml granulocyte-macrophage colony-stimulating factor (Sanofi Leukine, Bridgewater, NJ) and 20 ng/ml IL-4 (catalogue no. 204-IL/CF; R&D Systems, Minneapolis, MN) for 5-7 days and subsequently matured with 100 ng/ml lipopolysaccharide (LPS) (catalogue no. L6529; Sigma) in the presence or absence of 100 ng/ml α-GalCer (catalogue no. KRN7000; Funakoshi, Tokyo, Japan) for 48-72 hr. iNKT cells were purified from peripheral blood mononuclear cells of healthy volunteers using magnetic bead sorting, and stimulated weekly with mature α-GalCer-loaded moDC in Yssel's medium supplemented with 1% human AB serum, 10 U/ml IL-7 (catalogue no. 207-II/CF; R&D Systems) and 10 ng/ml IL-15 (catalogue no. 34-8159; eBioscience). γδ T cells were purified from peripheral blood mononuclear cells of healthy volunteers using magnetic bead sorting, and stimulated weekly with pamidronate (10 μM) (PCH, Pharmachemie BV, Haarlem, The Netherlands) loaded moDC in Yssel's medium supplemented with 1% human AB serum, 100 U/ml IL-2 (BioVision, Mountain View, California, USA) 10 U/ml IL-7 and 10 ng/ml IL-15. Alternatively, γδ T cells were weekly stimulated with irradiated feeders cells (1×10$^6$ mixed PBMC's of two donors and 0.1×10$^6$ JY cells), 10 IU/mL rhIL-7, 10 μg/mL rhIL-15 and 50 ng/mL PHA in in RPMI-1640 medium supplemented as described above. Depending on culture density, cultured cells were split and fresh culture medium was added. Pure (>95% Vα24+Vβ11+ or Vγ9+Vδ2+) iNKT and γδ T cells were used for experiments.

Generation of Anti-CD1d and Anti-γδTCR Specific VHH

The anti-CD1d and anti-γδTCR specific VHHs were identified and generated as described previously (Lameris R et al (2016) Immunology 149(1):111; De Bruin et al (2016) Clin Immunol 169:128). Tag-less 1D12 (SEQ ID NO:75), 1D22 (SEQ ID NO-84) and 1D12-5C8 (SEQ ID NO:160) were produced by UPE (Utrecht, the Netherlands).

In Vivo Xenograft Mouse Multiple Myeloma (MM) Model

A disseminated MM model was established by intravenous transfer of CD1d$^+$ MM cells into NOD scid gamma (NSG) mice. Female 18-26-week-old NSG mice (Charles River) were irradiated with 2 Gy 24 hr prior to intravenous (i.v.) injection of 2.5×10$^6$ MM.1s.mcherry/luc.CD1d cells via the tail vain (day 0). On day 7, 14 and 21, 1×10$^7$ human iNKT cells, human γδ T cells or a mixture thereof (1:1 ratio) were i.v. injected. Mice were bi-weekly intraperitoneally (i.p.) injected with PBS or bispecific antibody 1D12-5C8 (100 μg/mouse). Mice were euthanized when pre-set human end-points were reached. Animal experiments were approved by the Dutch Central Authority for Scientific Procedures on Animals (CCD).

Example 1

Modulation of iNKT Cell Activation

Figure 1:
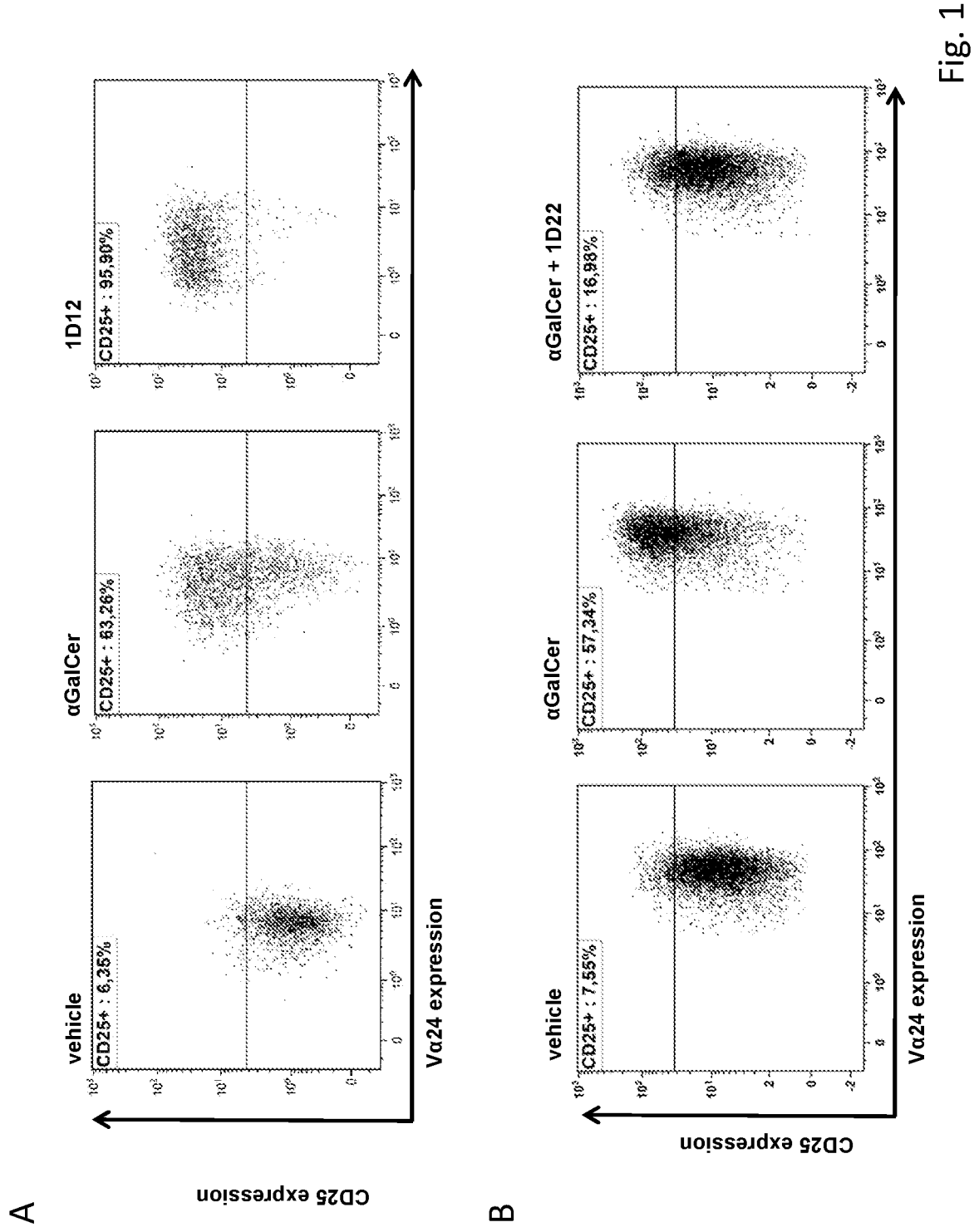
FIG. 1. Anti-CD1d VHH mediated activation and inhibition of invariant natural killer T (iNKT) cells. iNKT CD25 expression and interferon-γ (IFN-γ) production were determined after a 24-hr co-culture of iNKT cells with CD1d-transfected HeLa cells pulsed with vehicle control (vehicle) or αGalCer whether or not in combination with anti-CD1d VHH 1D12 (100 nM) or 1D22 (1000 nM). Representative dot-plots illustrating marked activation by 1D12 (A) or inhibition by 1D22 (B) of iNKT cells as depicted by CD25 expression, in addition to a marked increase (by 1D12) or decrease (by 1D22) in iNKT cell IFN-γ production (C and D). Data represent mean+SD of 3-4 individual experiments with iNKT obtained from different donors, P<0.01, *P<0.001, calculated with a one-way analysis of variance with Turkey's post hoc test.
Figure 1:
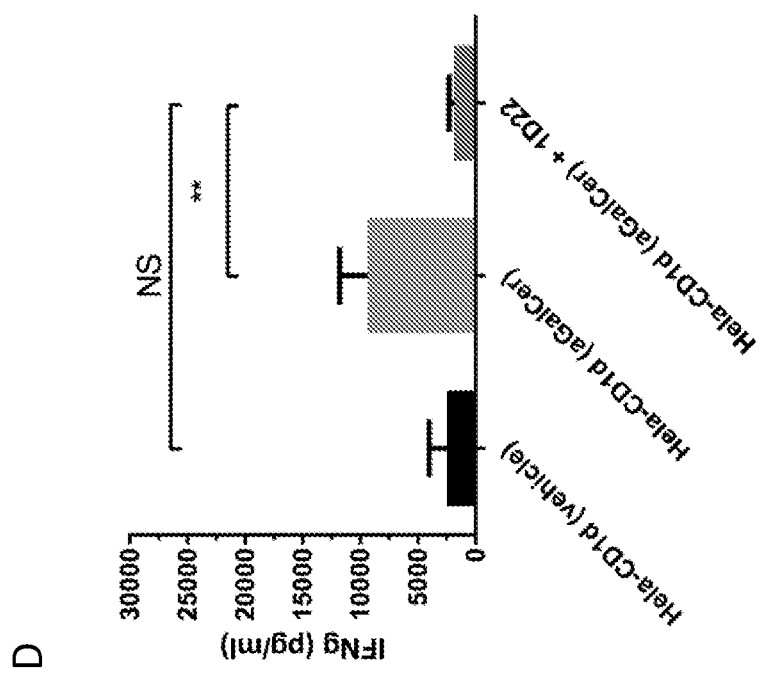
Figure 1:
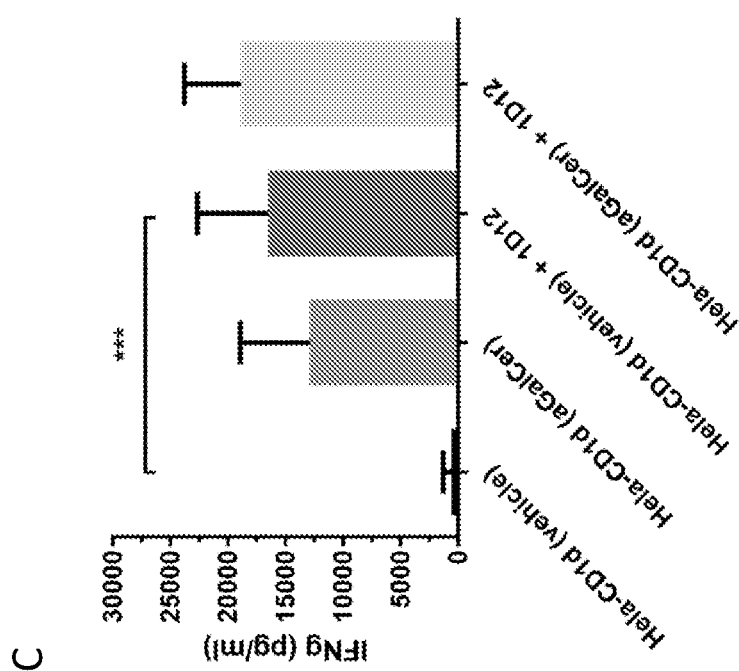

To evaluate the capacity of 1D12 and 1D22 to stimulate or inhibit iNKT cell activation, 5×10$^4$ Hela-CD1d cells were seeded per well in a 96-well tissue culture plate and pulsed overnight with vehicle control (DMSO 0.01%) or 100 ng/ml α-GalCer. Cells were then washed with PBS and incubated with medium, or the anti-CD1d specific VHH for 1 hr at the indicated concentrations. Subsequently, 5×10$^4$ pure and resting iNKT were added to each well. After 24 hr, culture supernatants were analyzed for (induction or inhibition of) cytokine production by CBA (BD Biosciences) whereas iNKT cells were harvested and analyzed for CD25 expression by flow cytometry. As can be seen in FIG. 1, we identified an anti-CD1d VHH (clone 1D22) that completely blocked iNKT cell activation and cytokine production ($P<0.0001$) and thus recognition of the CD1d-α-GalCer complex. In sharp contrast anti-CD1d VHH clone 1D12 was found to potentiate CD1d-restricted iNKT cell activation even in the absence of exogenously added glycolipid Ag (FIGS. 1a and c) ($P<0.0001$).

Example 2

Figure 2:
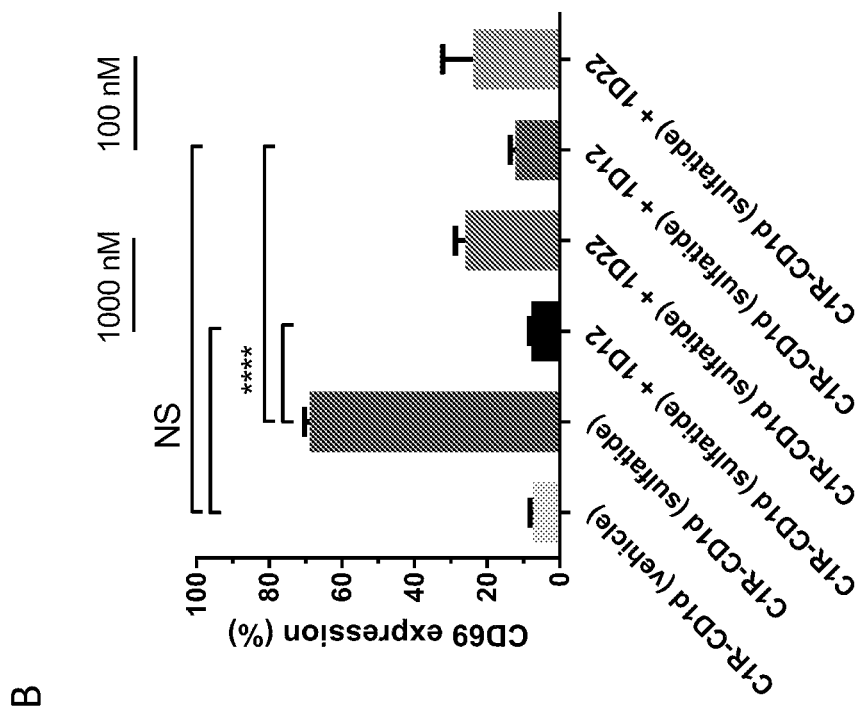
FIG. 2. Vδ1-sulf-CD1d interaction is prevented by anti-CD1d VHH 1D12 and reduced by 1D22. Endogenous or sulfatide loaded CD1d-PE tetramers were incubated with either PBS (control), 1D12 or 1D22 (4:1VHH:CD1d ratio) after which tetramers were used to stain Jurkat-Vδ1 cells (final concentration tetramer 2 μg/ml) in combination with CD3-APC. Tetramer binding is prevented by 1D12 and reduced by 1D22 (A). C1R-CD1d cells were incubated with DMSO controls or sulfatide (25 μg/ml) after which medium or anti-CD1d VHH were added at 1000 or 100 nM and incubated for 30 min. Next Jurkat-Vδ1 cells were added and the co-culture was incubated for an additional 24 h after which CD69 expression was determined by flow cytometry (B). N=3.
Figure 2:
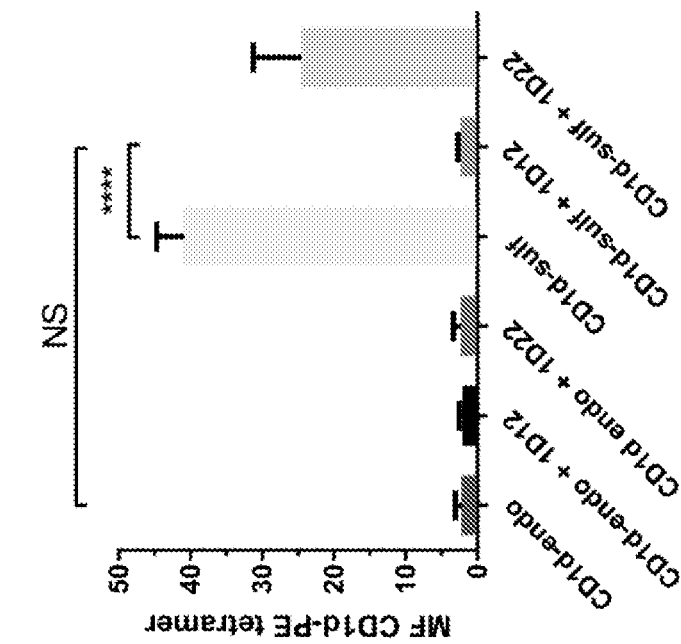

Modulation of Jurkat-Vδ1 Cell Activation iNKT cells are known to dock over the extreme F' pocket of CD1d which contrasts with sulfatide-CD1d restricted Vδ1-T cells that dock more towards the A' pocket. We therefore evaluated the effect of 1D12 and 1D22 on sulfatide-CD1d restricted Vδ1-T cells. To evaluate the effect of 1D12 and 1D22 on Jurkat-Vδ1 cell activation, 1×10$^5$ C1R-CD1d cells were seeded per well in a 96-well tissue culture plate and pulsed for 2 hr with vehicle control (DMSO 0.05%) or 25 μg/ml sulfatide. Cells were then incubated with medium, or the anti-CD1d specific VHH for 1 hr at 100 nM (not depicted) or 1000 nM. Subsequently, 5×10$^4$ Jurkat-Vδ1 were added to each well. After 24 hr Jurkat-Vδ1 cells were harvested and analysed for CD69 expression by flow cytometry. As can be seen in FIG. 2B, addition of 1D12 during the co-culture completely abrogated activation of Vδ1-Jurkat, whereas 1D22 had only a limited impact on expression of the activation marker CD69. Incubation with 100 nM or 1000 nM yielded similar results (data not shown).

To evaluate the effect of 1D12 and 1D22 on CD1d-tetramer binding on Jurkat-Vδ1 cells, endogenous or sulfatide-loaded CD1d-PE tetramers were incubated with either PBS (control), 1D12 or 1D22 (ratio VHH:CD1d of ~4:1) for 30 min at room temperature after which tetramers were added to Jurkat-Vδ1 cells (final concentration tetramer 2 µg/ml) in combination with CD3-APC and incubated for 45 min at 4 degrees Celsius. Data was analyzed by flow cytometry. Incubation of sulfatide-loaded CD1d tetramers with 1D12 prevented binding to Jurkat-Vδ1 cells completely, while 1D22 had only a limited impact (FIG. 2A). These data support the ability of the anti-CD1d VHH to modulate reactivity of specific CD1d restricted T-cells, which contrast sharply with known mAb, such as 51.1 mAb, that block CD1d-TCR interaction of a broad range of CD1d-restricted T-cells (Nambiar et al. (2015) MAbs 7:638; Migalovich Sheikhet et al. (2018) Front Immunol 9:753).

Example 3

Dual Activation of iNKT and Vγ9Vδ2-T Cells by a Bispecific Anti-CD1d-Anti-Vγ9Vδ2 TCR VHH Previously, well characterized anti-Vγ9Vδ2-TCR VHH have been fused to VHHs specific for tumor-associated antigens for anti-tumor therapeutic purposes. CD1d is expressed on various (hematological) malignancies and on tumor associated macrophages and myeloid-derived suppressor cells and could therefore be used as an anti-cancer therapeutic target. To evaluate the ability of 1D12-5C8 to induce dual activation of iNKT and Vγ9Vδ2-T-cells resulting in tumor target lysis, $1\times10^5$ CCRF-CEM cells were incubated with either $5\times10^4$ iNKT cells, $5\times10^4$ Vγ9Vδ2-T cells or $5\times10^4$ mixed iNKT/Vγ9Vδ2-T (1:1 ratio) in the presence of medium alone, monovalent 1D12 or bispecific 1D12-5C8. After 4 hr degranulation of effector cells was measured by CD107a expression and analyzed by flow cytometry. To asses cytotoxicity towards target cells, living CCRF-CEM cells (Annexin V and 7-AAD negative) were quantified after 16 h co-culture using flow cytometry cell counting beads.

To determine the capacity of 1D12-5C8 to support iNKT and Vγ9Vδ2-T expansion and control tumor growth, freshly isolated iNKT and Vγ9Vδ2-T from the same donor were expanded for 1 week. $5\times10^4$ MM.1s-CD1d cells were subsequently incubated with medium or 1D12-5C8 (50 nM) for 30 min after which iNKT, Vγ9Vδ2-T cells or a mixture thereof (2:3 ratio) was added in a 10:1 target:effector ratio. Living MM.1s-CD1d (or MOLM-13 or NOMO-1), iNKT and Vγ9Vδ2-T cells (7-AAD negative) were quantified after 7 days using flow cytometry cell counting beads.

Figure 3:
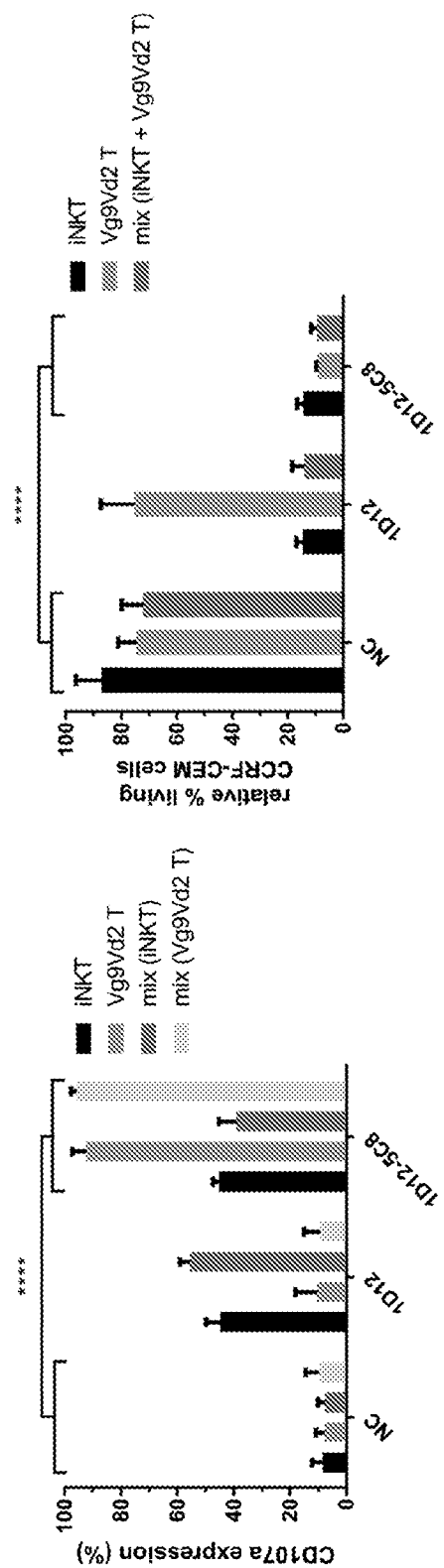
FIG. 3. Dual activation of iNKT cells and Vγ9Vδ2-T cells by a bispecific CD1d and Vγ9Vδ2-TCR targeting VHH resulting in effector cell degranulation and rapid tumor cell lysis. CD1d-expressing CCRF-CEM cells were incubated with either iNKT cells or Vγ9Vδ2-T cells or both at an effector to target ratio of 1:2 in the presence of medium only, monovalent 1D12 or bispecific 1D12-5C8. Robust degranulation (as depicted by CD107a expression) of iNKT cells in the presence of 1D12 was observed, but only simultaneous degranulation of iNKT cells and Vγ9Vδ2-T cells was seen in the presence of the bispecific VHH (A). In accordance, a striking reduction in living CCRF-CEM cells (B) was observed. Data represent mean+SD of 3 individual experiments with iNKT/Vγ9Vδ2-T obtained from different donors.

As can be seen in FIG. 3a, robust simultaneous degranulation of iNKT and Vγ9Vδ2-T cells was only observed in the presence of the bispecific construct. Moreover, effector cell activation resulted in a striking reduction in living tumor cells (FIG. 3b).

Figure 4:
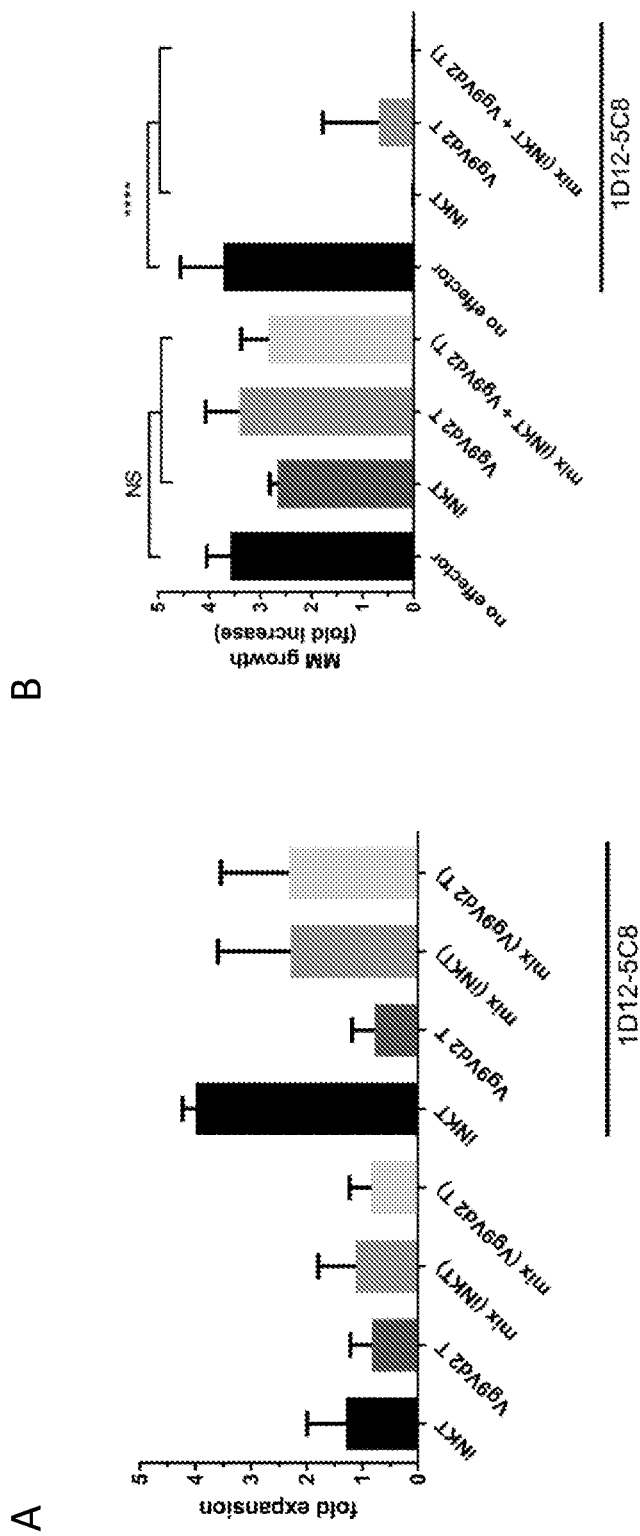
FIG. 4. Bispecific 1D12-5C8 supports iNKT and Vγ9Vδ2-T cell expansion and induces tumor growth control. iNKT, Vγ9Vδ2-T or a mixture (2:3 ratio) were incubated with MM.1s-CD1d cells at an effector to target ratio of 1:10 in the presence of medium only or bispecific 1D12-5C8. Clear induction of iNKT cell expansion was observed, however Vγ9Vδ2-T expansion was only observed in the presence of 1D12-5C8 and iNKT cells (A). Noteworthy, tumor growth was contained in the presence of 1D12-5C8 (B). Data represent mean+SD of 3 individual experiments with paired iNKT/Vγ9Vδ2-T obtained from different donors.

The unfavourable effector to target ratio in vivo, usually requires expansion of tumor targeting effector cells to control tumor growth. To investigate whether the bispecific 1D12-5C8 VHH could induce both effector cell expansion and tumor control in such a setting, MM.1s-CD1d cells were incubated with 1D12-5C8, after which iNKT, Vγ9Vδ2-T cells or a mixture thereof were added at an effector to target ratio of 1:10. The ability of 1D12-5C8 to induce expansion and control tumor growth was evaluated after a 7 day co-culture by flow cytometric quantification of these cells. As can be seen in FIG. 4a expansion of iNKT was observed in the presence of the bispecific construct. However, Vγ9Vδ2-T cells only showed expansion in the presence of both iNKT cells and the bispecific construct. Moreover, robust tumor growth control was induced by the bispecific construct in combination with effector cells (FIG. 4b). Similar, tumor growth control and effector cell expansion were observed with the acute myeloid leukemia tumor cell lines MOLM-13 and NOMO-1 (not shown), underscoring the powerful anti-tumor efficacy and broad applicability of this bispecific anti-CD1d-anti-Vγ9Vδ2-TCR VHH.

Example 4

Binding Competition of 1D12 and 1D12-5C8

To evaluate whether 1D12 binding would interfere with 1D12-5C8 binding, $1\times10^5$ MM1s-CD1d cells were incubated with either PBS (negative control, NC), 1D12 (1000 nM), 1D22 (1000 nM) or anti-CD1d mAb 51.1 (100 nM) for 45 min after which PBS (NC) or NHS-biotin (ThermoFischer Scientific Inc., Waltham, MA) linked 1D12-5C8 (100 nM) was added for an additional 30 min at 4 degrees Celsius. After extensive washing samples were stained with streptavidin-APC (eBioscience, San Diego, CA) and analyzed by flow cytometry.

Figure 5:
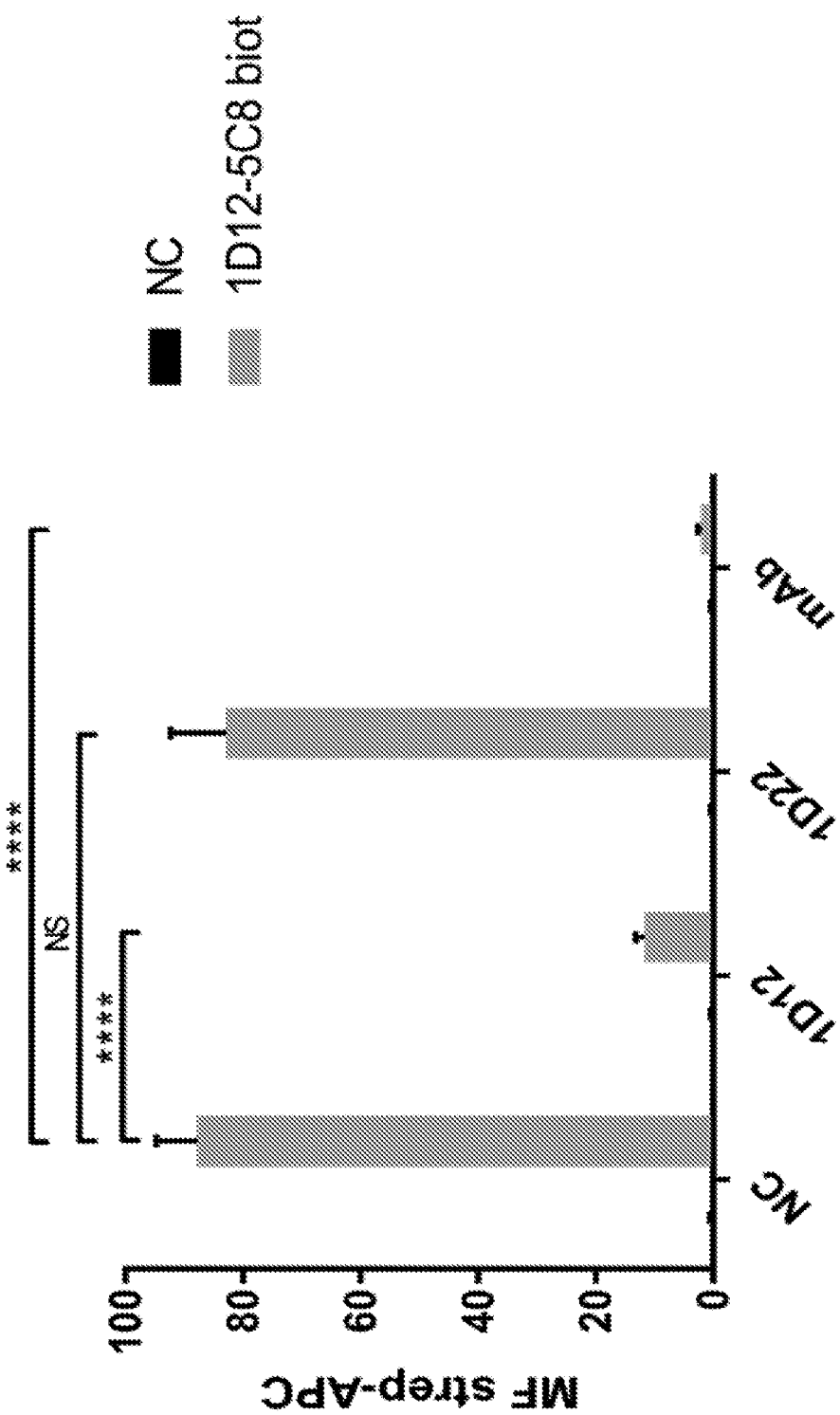
FIG. 5. Anti-CD1d VHH 1D12 and anti-CD1d 51.1 mAb, but not anti-CD1d VHH 1D22, interfere with binding of 1D12-5C8 bispecific VHH. CD1d transfected multiple myeloma cells (MM.1s) were incubated with for 45 min with PBS (negative control, NC), anti-CD1d VHH (1000 nM) or anti-CD1d mAb (100 nM) after which PBS (NC) or biotinylated 1D12-5C8 bispecific VHH (100 nM) was added and incubated for an additional 30 min. After extensive washing samples were stained with streptavidin-APC and analyzed by flow cytometry. Data represent mean+SD of 3 individual experiments, ****P<0.0001, calculated with a two-way analysis of variance with Turkeys's post hoc test.
Figure 6:
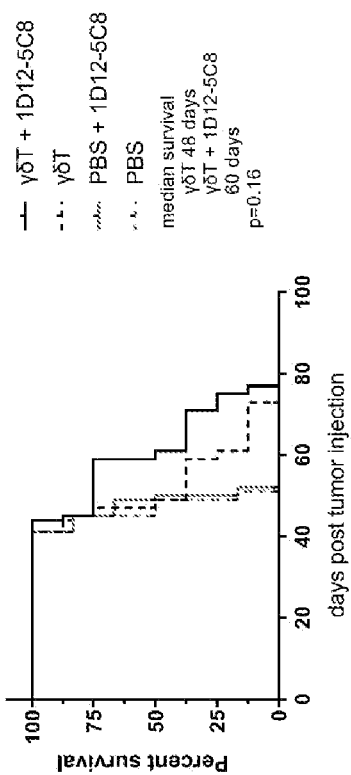
FIG. 6. Bispecific antibody 1D12-5C8 promotes survival in a mouse multiple myeloma model in the presence of iNKT and/or Vγ9Vδ2-T cells. Panel A shows the effects of administration of antibody 1D12-5C8 and/or iNKT cells on survival. Panel B shows the effects of administration of antibody 1D12-5C8 and/or Vγ9Vδ2-T cells. Panel C shows the effects of administration of antibody 1D12-5C8 and/or a mixture ("mix") of iNKT and Vγ9Vδ2-T cells.
Figure 6:
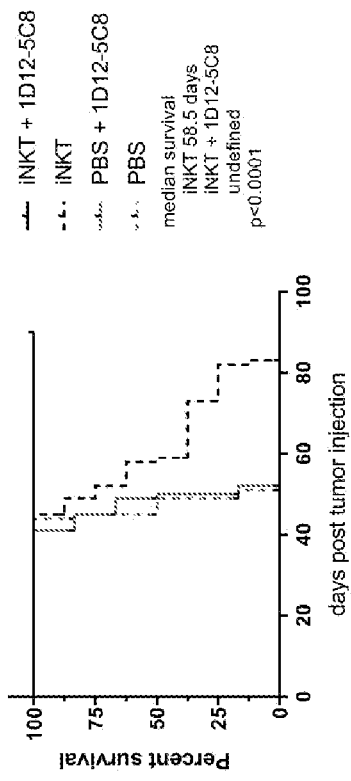
Figure 6:
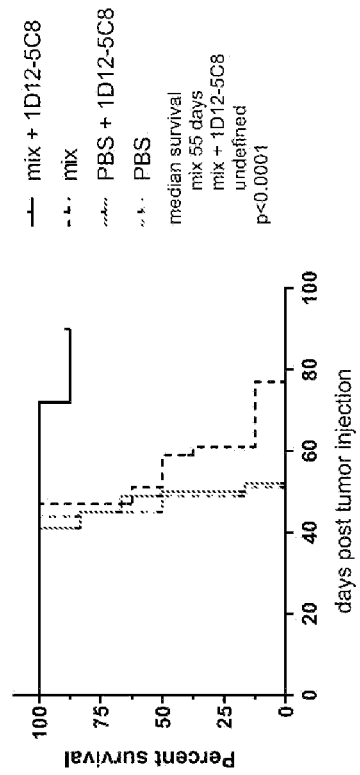

To evaluate competition between 1D12 and 1D12-5C8, CD1d expressing MM cells were sequentially incubated with either PBS, 1D12, 1D22 (which should not interfere with 1D12-5C8 binding) or anti-CD1d mAb 51.1) followed by biotinylated 1D12-5C8. The ability of 1D12-5C8 to complex with CD1d was then determined by analysing binding of streptavidin-APC by flow cytometry. As can be seen in FIG. 5, pre-incubation of 1D12 or anti-CD1d mAb 51.1, but not 1D22, greatly reduced 1D12-5C8 binding.

Example 5

In Vivo Xenograft Mouse Multiple Myeloma (MM) Model

The anti-tumour efficacy of bispecific CD1d/Vδ2 binding antibody 1D12-5C8 was studied in an in vivo model where mice were i.v. inoculated with MM.1s.mCherry/luc.CD1d cells to establish a disseminated MM model followed by three i.v. infusions of human iNKT cells, human γδ T cells or a mixture thereof starting 7 days post tumour inoculation whether or not in combination with 1D12-5C8. Whereas biweekly i.p. dosing of 1D12-5C8 alone had no effect (median survival 47 days versus 49.5 days, P>0.05), combination treatment of 1D12-5C8 and type I NKT cells significantly (p<0.0001) prolonged survival compared to iNKT alone (median survival 58.5 days) with all mice being alive at termination of the study (day 90). Compared to treatment with human γδ T cells only, treatment of human γδ T cells and 1D12-5C8 showed a trend towards increased median survival from 48 days to 60 days (p=0.16). Infusion of both type I NKT cells and γδ T cells with biweekly i.p. dosing 1D12-5C8 significantly prolonged survival with 7/8 mice being alive at study termination (day 90) (p>0.0001) compared to the mixture of the cells alone without antibody (median survival 55 days).

Example 6 Use of Bispecific CD1d/Vγ9Vδ2 Antibodies for the Treatment of Hematological Malignancies 6.1 Materials and Methods
Patient and Healthy Donor Material Peripheral blood mononuclear cells (PBMCs) were isolated from peripheral blood (PB) samples from untreated CLL patients or age-matched healthy control (HC) buffy coats from Sanquin Blood Supply (Amsterdam, the Netherlands) and cryopreserved. The presence of monoclonal B-cell lymphocytosis was excluded in HCs by CD5, CD19, κ and λ immunophenotyping. Healthy B cells were obtained from HC PBMCs by CD19 selection (130-050-301, magnetic microbeads, Miltenyi Biotec, Bergisch Gladbach, Germany). The study was approved by the medical ethics committee at the Amsterdam UMC. Written informed consent from all subjects was obtained in accordance with the Declaration of Helsinki.

Cell Lines

Culture medium was supplemented with 10% fetal calf serum (F7524), 0.05 mM β-mercapto-ethanol (M6250, both Merck, Kenilworth, NJ, USA), 200 mM L-glutamine (25030-123), and 10,000U/mL penicillin/streptomycin (15140-122, both Thermo Fisher Scientific, Waltham, MA, USA). The multiple myeloma cell line MM.1s, either wild-type (WT) or stably transduced with CD1d (kind gift from Dr. W. Song, Dana Farber Cancer Center, Boston, MA, USA) and mantle cell lymphoma cell line Jeko-1 were cultured in Roswell Park Memorial Institute 1640 medium (52400-025, Thermo Fisher Scientific). NIH-3T3 fibroblasts transfected with CD40L were cultured in supplemented Iscove's Modified Dulbecco's Medium (12440-053, Thermo Fisher Scientific).

Vγ9Vδ2-T cell lines were generated as described previously (de Bruin et al. (2017) Oncoimmunology 7(1): e1375641.). In short, Vδ2$^+$-T cells were isolated from HC PBMCs using FITC-conjugated anti-Vδ2 TCR (Table 4) in combination with anti-mouse IgG microbeads (130-048-401, Miltenyi Biotec) and cultured weekly with irradiated feeder mix consisting of PBMCs from 2 HCs, JY cells, IL-7 (10 U/mL, 207-IL-025), IL-15 (10 ng/mL, 247-ILB-25, R&D Systems, Minneapolis, MN, USA) and PHA (50 ng/mL, R30852801, Thermo Fisher Scientific). Purity of Vγ9Vδ2-T cell lines was maintained at >90%.

Flow Cytometry

Cells were stained with antibodies and viability dyes (Table 4) and measured on an LSR Fortessa or FACS Canto cytometer (BD Biosciences, Franklin Lakes, NJ, USA). Samples were analyzed with Flowjo MacV10. Cytofix/Cytoperm reagent was used for detection of intracellular cytokines (BD Biosciences). Relative CD1d expression is defined as geometric MFI (CD1d stained)—geometric MFI (fluorescence minus one).

Generation, Production and Purification of Bispecific Antibody 1D7-5C8

The CD1d-specific VHH 1D7 (SEQ ID NO:70) (WO2016122320) and the Vγ9Vδ2-specific VHH 5C8 (SEQ ID NO:149) (WO2015156673), binding to the Vδ2 chain of the TCR, were previously generated. In short, VHHs were generated by llama immunization and identified by subsequent phage display and screening. To create the CD1d-Vδ2 bispecific VHH, VHH 5C8 (C-terminal) was joined to VHH 1D7 (N-terminal) with a Gly$_4$Ser-linker. Bispecific antibody 1D7-5C8 (SEQ ID NO:165) protein from this gene sequence was produced in mammalian HEK293E-253 cells by UPE (Utrecht, the Netherlands) and purified from the supernatant by sequential protein A-based selection and size exclusion using fast protein liquid chromatography (ÄKTAexplorer, GE Healthcare, Chicago, IL, USA).

VHH Binding

To assess binding, CD1d-transfected MM.1s or Vγ9Vδ2-T cell lines were incubated with bispecific antibody 1D7-5C8 for 30 minutes at 37° C. Bound bispecific antibody 1D7-5C8 was detected by sequential incubation with rabbit-anti-llama and PE-conjugated goat-anti-rabbit antibodies for 20 minutes at 4° C. (Table 4).

Cytokine and Degranulation Assays

Vγ9Vδ2-T cell lines were incubated with bispecific antibody 1D7-5C8 or medium control for 30 minutes at 37° C. Subsequently, Vγ9Vδ2-T cells were cocultured with Jeko-1 cells for 4 hours in a 1:1 ratio in the presence of Brefeldin A (10 μg/mL; B7651, Sigma-Aldrich, St. Louis, MO, USA), GolgiStop (554724, BD Biosciences) and anti-CD107a (Table 4).

In the assays with autologous Vγ9Vδ2-T cells, CLL PBMCs were partially depleted of CD19$^+$ cells using magnetic beads (Miltenyi Biotec; after depletion ±50% of cells were CD19$^+$) and then cultured overnight with bispecific antibody 1D7-5C8 or medium control in the presence of Brefeldin A, GolgiStop and anti-CD107a.

Cytotoxicity Assays

For cytotoxicity assays, target cells were labeled with carboxyfluorescein succinimidyl ester (CFSE; C1157, Thermo Fisher Scientific) or Cell Trace Violet (CTV; C34557, Thermo Fisher Scientific) and incubated with bispecific antibody 1D7-5C8 or medium control for 30 minutes at 37° C. Target cells were then cocultured overnight with Vγ9Vδ2-T cell lines in a 1:1 ratio unless otherwise indicated. Viability was measured using Mitotracker Orange (25-minute incubation at 37° C., M7510) and To-pro-3 (10-minute incubation at room temperature; T3605, both Thermo Fisher Scientific).

If indicated, target cells were pretreated with 25 μM mevastatin (M2537, Sigma-Aldrich), 50 μM aminobisphosphonates (pamidronate, #12J08RD, TEVA Pharmachemie, Haarlem, the Netherlands) or medium control for 2 hours.

If indicated, cells were cultured with the indicated concentrations of all-trans retinoic acid (ATRA; R2625, Sigma-Aldrich) for 48 hours unless otherwise indicated. ATRA was washed away prior to cytotoxicity assays.

If indicated, target cells were pre-incubated with 5 μg/mL anti-CD1d mAb (clone 51.1, 350304, Biolegend, San Diego, CA, USA) and/or 10 μg/mL anti-CD277 mAb (clone 103.2, Creative Biolabs, Shirley, NY, USA) for 10 minutes.

For cytotoxicity assays performed with patient-derived Vγ9Vδ2-T cells, CD3$^+$ cells were enriched from patient PBMC by magnetic bead selection (130-050-101, Miltenyi Biotec; ≥90% purity). Pure PBMCs were pre-incubated with bispecific antibody 1D7-5C8 or medium control for 30 minutes at 37° C. and cultured overnight with purified CD3$^+$ cells from the same patient in a 5:1 or 20:1 (CD3$^+$:PBMC) ratio. Viable cells were then quantified by fluorescence-labeled antibodies and viability dyes in combination with counting beads (01-1234-42, Thermo Fisher Scientific).

Proliferation Assays

For proliferation assays, PBMCs from CL patients were enriched for T cells by depletion of CD19$^+$ CLL cells. After attachment of irradiated (30Gy) CD401L-expressing fibroblasts to culture plates, T cell enriched PBMC (≤10% CD19$^+$) and purified CD19$^+$ (≥90% CD19$^+$) PBMC fractions were added in a 2:1 (CD19:CD19$^+$) ratio. Cells were cultured in the presence of 50 IU/mL IL-2 (200-02, Peprotech, Rocky Hill, NJ, USA) or 50 IU/mL IL-2 and 50 nM bispecific antibody 1D7-5C8 for 1 week.

TABLE 4

| Reactivity | Antibody | Format | Clone | Catalogue number | Company | Host |
|---|---|---|---|---|---|---|
| Human | CD1d | APC | 51.1 | 350307 | Biolegend | Mouse |
| Human | CD3 | V500 | UCHT1 | 561416 | BD | Mouse |
| Human | CD3 | AF700 | UCHT1 | 56-0038-82 | Thermo Fisher | Mouse |
| Human | CD3 | PerCP-eF710 | SK7 | 46-0036-42 | Thermo Fisher | Mouse |
| Human | CD5 | PE | UCHT2 | 12-0059-42 | Thermo Fisher | Mouse |
| Human | CD19 | AF700 | HIB19 | 557921 | BD | Mouse |
| Human | CD19 | PerCP-Cy5.5 | SJ25C1 | 332780 | BD | Mouse |
| Human | CD25 | BV786 | M-A251 | 563701 | BD | Mouse |
| Human | CD69 | APC Fire750 | FN50 | 310946 | Biolegend | Mouse |
| Human | CD107a | PECy7 | H4A3 | 561348 | BD | Mouse |
| Human | Vα24 | FITC | C15 | IM1589 | Beckman Coulter | Mouse |
| Human | Vβ11 | PE | C21 | IM2290 | Beckman Coulter | Mouse |
| Human | Vγ9-TCR | PE | B3 | 2256535 | Sony | Mouse |
| Human | Vδ2-TCR | FITC | B6 | 2257030 | Sony | Mouse |
| Human | IFN-γ | BUV395 | B27 | 563563 | BD | Mouse |
| Human | IFN-γ | BV421 | B27 | 562988 | BD | Mouse |
| Human | TNF-α | BV650 | MAB11 | 563418 | BD | Mouse |
| LLama | Sera | Unconjugated | | K976 | QVQ | Rabbit |
| Rabbit | IgG/IgM | PE | Polyclonal | 4010-09S | Southern Biotech | Goat |
| Rabbit | Ig | FITC | Polyclonal | F0054 | Dako | Swine |
| Fixable Viability Dye | | eFluor 506 | | 65-0866-14 | Thermo Fisher | |
| Fixable Viability Dye | | eFluor 780 | | 65-0866-14 | Thermo Fisher | |
| Live/Dead fixable staining | | Red | | L34972 | Thermo Fisher | |

6.2 The Majority of CLL Patients Express CD1d on the Cell Surface

Figure 7:
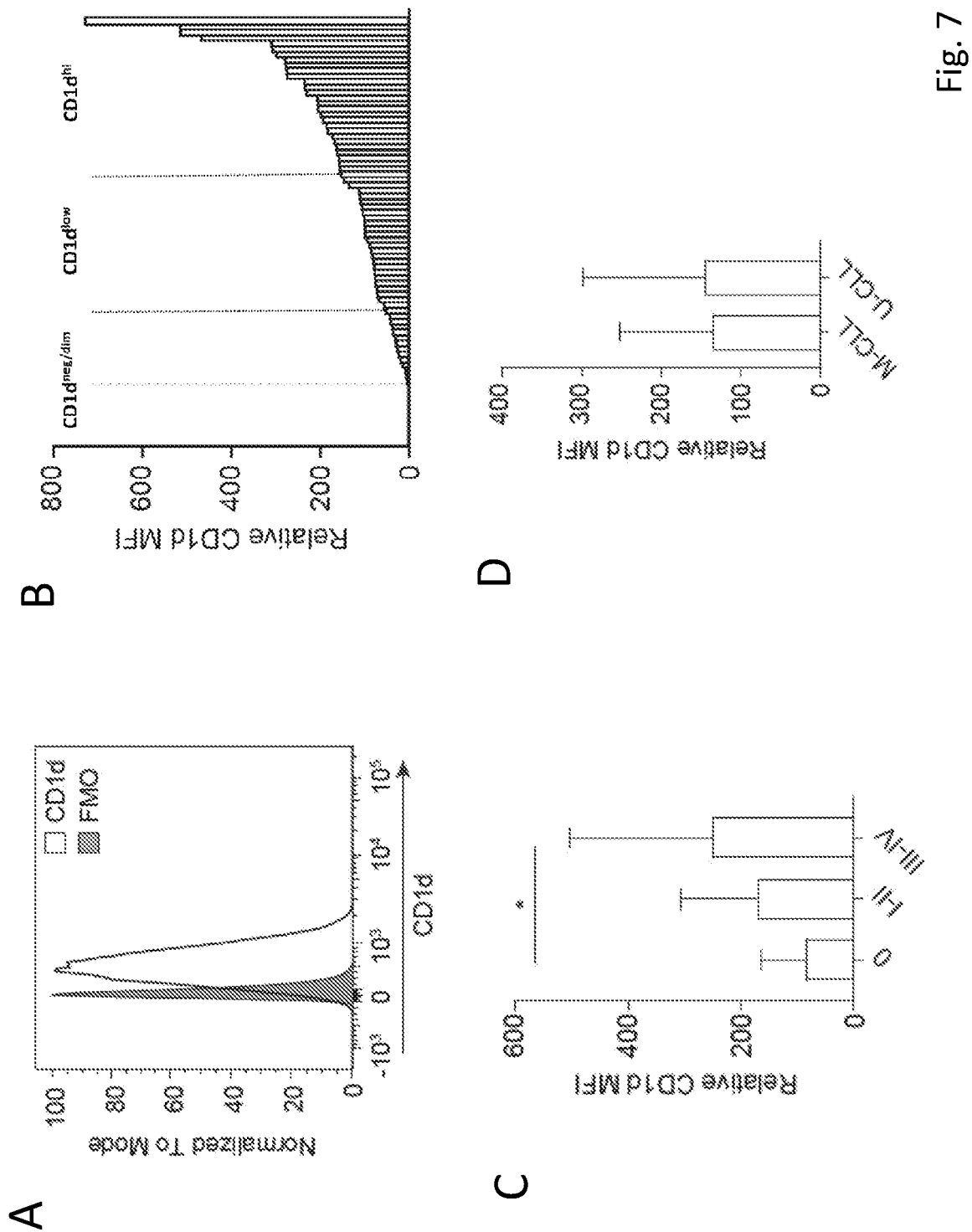
FIG. 7. CD1d Expression on CLL Cells.

In order to assess the suitability of CD1d as a target for antibody-based treatment in CLL, we analyzed CD1d surface expression on CLL cells in a cohort of 78 untreated patients. Within each patient sample, CD1d was expressed homogenously (FIG. 7A). However, the expression of CD1d was highly variable across the cohort (median relative MFI 131.2±135.1; FIG. 7B). We categorized the cohort into three groups, that each contained approximately one-third of the cohort, based on negative or very low (neg/dim) (relative MFI <50), low (relative MFI >50 and <150) or high (relative MFI >150) CD1d levels.

CD1d expression was higher on CLL cells from patients with advanced stage disease according to Rai classification (FIG. 7C). There was no difference in CD1d levels between patients with mutated (M-CLL) or unmutated (U-CLL) immunoglobulin heavy chain (IgVH) genes (FIG. 7D).

In summary, CD1d is expressed on the surface of leukemic cells from approximately two-thirds of CLL patients, particularly in patients with advanced disease.

6.3 Bispecific Anti-CD1d-Vδ2 VHH Induces Effector Responses of Vγ9Vδ2-T Cells

Next, we constructed a bispecific anti-CD1d Vγ9Vδ2-T cell engager by joining the previously generated CD1d-specific VHH 1D7 and the Vδ2-specific VHH 5C8 with a Gly$_4$-Ser linker. The previously characterized CD1d-specific VHH has a high affinity for CD1d, without affecting DC maturation or recognition of glycolipid-loaded CD1d by iNKT cells (Lameris et al. (2016) Immunology 149(1):111). Prior characterization of the Vγ9Vδ2-T cell-specific VHH demonstrated that it binds to the Vδ2 chain of the TCR and can conditionally activate Vγ9Vδ2-T cells (de Bruin et al. (2016) Clin Immunol 169:128).

We first confirmed that binding to CD1d and Vγ9Vδ2-T cells is retained in the bispecific format. The bispecific antibody 1D7-5C8 bound with high affinity to cultured Vγ9Vδ2-T cells (apparent Kd 0.36 nM and to CD1d-transfected MM.1s cells (apparent Kd 0.40 nM), similar to data obtained with our monovalent VHHs (Lameris et al. (2016) Immunology 149(1):111; de Bruin et al. (2016) Clin Immunol 169:128).

Subsequently, we tested whether the bispecific antibody could induce Vγ9Vδ2-T cell activation. For this purpose, Vγ9Vδ2-T cells were cultured together with Jeko-1 cells, a malignant B cell line that naturally expresses CD1d at moderate levels (Li et al. (2014) Med Sci (Basel) 2(2):82). Vγ9Vδ2-T cells did not produce IFN-γ and hardly degranulated in response to exposure to target cells alone or to the bispecific antibody 1D7-5C8 alone, but this was dose dependently enhanced in cultures containing both Jeko-1 cells and the bispecific antibody 1D7-5C8 (FIG. 8A). The half-maximum activating effect on Vγ9Vδ2-T cells was reached around 3 pM (EC50 IFN-γ: 2.6 pM, TNF-α: 3.5 pM, CD107a: 3.1 pM; FIG. 8B).

In conclusion, we generated a bispecific anti-CD1d-Vδ2 VHH that elicits target cell-dependent Vγ9Vδ2-T cell activation at low picomolar concentrations.

6.4 The Bispecific Antibody 1D7-5C8 Promotes CD1d-Dependent Cytotoxicity

We then evaluated whether the activation of Vγ9Vδ2-T cells also led to lysis of CD1d$^+$ tumor cells. Less than ten percent of Jeko-1 cells were lysed during overnight coculture with Vγ9Vδ2-T cells alone. The bispecific antibody 1D7-5C8 enhanced target lysis in a dose-dependent manner, lysing 75.2%±21.0 of the Jeko-1 cells in the presence of 10 nM bispecific antibody 1D7-5C8 (FIG. 9A). The bispecific antibody 1D7-5C8 did not induce target cell lysis in the absence of Vγ9Vδ2-T cells.

Next, we analyzed the specificity of bispecific antibody 1D7-5C8-induced cytotoxicity using CD1d-transfected and wildtype CD1d-negative MM.1s cells (FIG. 9B). When the MM.1s cells were exposed to Vγ9Vδ2-T cells alone, less than 20% lysis of both the wildtype and CD1d$^+$ cells was observed during overnight coculture (FIG. 9C). The bispecific antibody 1D7-5C8 clearly increased lysis of the CD1d$^+$ cells, but had no effect on lysis of the wildtype cells, demonstrating that the Vγ9Vδ2-T cell-mediated cytotoxicity triggered by the bispecific antibody 1D7-5C8 is CD1d-specific.

We then tested the efficacy of the bispecific antibody 1D7-5C8 against primary CLL cells in samples with variable CD1d expression levels. Again, a minority of CLL target cells was killed when exposed to Vγ9Vδ2-T cells alone after overnight coculture (FIG. 9D). The bispecific antibody 1D7-5C8 enhanced cytotoxicity against CLL cells with low or high CD1d expression, but not with negative CD1d expression. Furthermore, CD1d$^{high}$ CLL cells were more susceptible to bispecific antibody 1D7-5C8-induced cell death than CD1d$^{low}$ CLL cells, as 100 nM bispecific antibody 1D7-5C8 induced lysis in 49.3%±6.6 of CD1d$^{low}$ cells versus 74.5%±19.1 of CD1d$^{high}$ cells (P=0.0083).

Taken together, the bispecific anti-CD1d-Vδ2 VHH potently enhances Vγ9Vδ2-T cell mediated cytotoxicity against tumor cells in a CD1d-dependent manner.

6.5 The Bispecific Anti-CD1d-Vδ2 VHH Induces Lysis of Autologous Leukemic Cells by Vγ9Vδ2-T Cells from CLL Patients Since Vγ9Vδ2-T cells from CLL patients can be functionally suppressed (de Weerdt et al. (2018) Blood 132(21): 2260; Coscia et al. (2012) Blood 120(16):3271), we assessed whether CLL patient-derived Vγ9Vδ2-T cells could be activated by the bispecific antibody 1D7-5C8. Vγ9Vδ2-T cells present in the PBMC fraction of CLL patients upregulated the activation marker CD25 on average 20.8-fold upon overnight culture with the bispecific antibody 1D7-5C8, to a level that was comparable to and not significantly different from that observed when PBMC were cultured with ABP (20.5-fold, FIG. 10A).

The bispecific antibody 1D7-5C8 also induced production of IFN-γ and TNF-α by the patient-derived Vγ9Vδ2-T cells (FIG. 10B) and in addition triggered Vγ9Vδ2-T cell degranulation (FIG. 10C).

Next, we evaluated whether the induction of Vγ9Vδ2-T cell effector responses by the bispecific antibody 1D7-5C8 would also enable lysis of autologous leukemic cells. For this purpose, we enriched for Vγ9Vδ2-T cells by culturing magnetically isolated CD3$^+$ cells (≥90% purity) together with full PBMCs from the same donor in a CD3:PBMC ratio of 5:1 (±1:20 Vδ2:CLL) or 20:1 (±1:5 Vδ2:CLL) in the presence or absence of the bispecific antibody 1D7-5C8. Patient-derived Vγ9Vδ2-T cells were capable of inducing cell death in autologous CLL cells, with a higher Vγ9Vδ2-T cell:tumor ratio leading to more leukemic cell death (FIG. 10D).

We then determined whether the bispecific antibody 1D7-5C8 could also promote proliferation of Vγ9Vδ2-T cells when added to PBMCs from CLL patients enriched for T cells by CD19 magnetic isolation (2:1 CD19$^-$:CD19$^+$ ratio). After one week of culture in the presence of 50 IU/mL IL-2, the percentage of Vγ9Vδ2-T cells within the T cell fraction (baseline 1.2%±1.0) increased in all 8 samples tested and was 3.1-fold higher with the bispecific antibody 1D7-5C8 (5.6%±4.7) than without (1.8%±1.5, P=0.0353, FIG. 10E).

Together these data indicate that the bispecific antibody 1D7-5C8 is capable of activating CLL patient-derived Vγ9Vδ2-T cells and thereby enables autologous tumor lysis at relatively low E:T ratios and promotes Vγ9Vδ2-T cell proliferation.

6.6 ATRA Upregulates CD1d Expression and Enhances Bispecific Anti-CD1d-Vδ2 VHH-Induced Cytotoxicity ATRA can increase the expression of CD1d on B cells (Allan et al. (2011) J Immunol. 186(9):5261). Since the capacity of the bispecific antibody 1D7-5C8 to induce target lysis was dependent on CD1d expression levels, we hypothesized that ATRA-induced upregulation of CD1d could increase cytotoxicity. ATRA caused upregulation of CD1d expression on Jeko-1 cells, which was detectable with 10 pM of ATRA and further increased with higher doses (FIG. 11A). Peak CD1d expression occurred after two days of culture (FIG. 11B).

ATRA did not induce cell death directly, nor did ATRA pretreatment increase Vγ9Vδ2-T cell-mediated cytotoxicity in the absence of the bispecific antibody (FIGS. 11C and D). However, Jeko-1 cells that were pretreated with ATRA were more sensitive to bispecific antibody 1D7-5C8-induced cell death than control Jeko-1 cells (FIG. 11D).

Next, we tested whether ATRA would also increase CD1d expression on primary CLL cells. CD1d levels increased 2.6-fold with 1 nM of ATRA and the highest expression occurred with 100 nM ATRA (3.7-fold increase on average, FIG. 11E). There was considerable variation after ATRA treatment (relative MFI after 100 nM ATRA: 504.6±366.0), which could partially be explained by baseline CD1d expression ($r^2$=0.4025, p=0.0062).

As with Jeko-1 cells, ATRA pretreatment of primary CLL cells did not affect their sensitivity to Vγ9Vδ2-T cell-mediated lysis in the absence of the bispecific antibody 1D7-5C8 (FIG. 11F), but did sensitize primary CLL cells to bispecific antibody 1D7-5C8-mediated cell death.

In summary, ATRA increased the susceptibility of tumor cells towards Vγ9Vδ2-T cell-mediated lysis induced by bispecific anti-CD1d-Vδ2 VHH by upregulating CD1d expression.

6.7 Modulation of Phosphoantigen Recognition by Vγ9Vδ2-T Cells Alters Bispecific Anti-CD1d-Vδ2 VHH-Induced Target Lysis In previous work, we found that the Vδ2-specific VHH 5C8 was not effective in inhibiting phosphoantigen-CD277 mediated Vγ9Vδ2-T cell activation (de Bruin et al. (2017) J Immunol. 198(1):308). We therefore wondered whether the level of Vγ9Vδ2-T cell activation induced by the bispecific antibody 1D7-5C8 could be affected by residual recognition of the phosphoantigen-CD277 complex. Because the mevalonate pathway is often overactive in malignant cells, we hypothesized that ABP could enhance bispecific antibody 1D7-5C8-induced cytotoxicity specifically against tumor cells.

Jeko-1 cells were more sensitive to Vγ9Vδ2-T cell-mediated cytotoxicity following pretreatment with the ABP pamidronate (FIG. 12A). In contrast, pretreatment with mevastatin, which reduces intracellular phosphoantigen levels (Boutin et al. (2018) Front Immunol. 9:828), led to a reduction in lysis. A similar pattern was observed in the presence of the bispecific antibody 1D7-5C8, in which pamidronate pretreatment led to an increase in bispecific antibody 1D7-5C8-induced lysis of Jeko-1 cells, whilst mevastatin decreased bispecific antibody 1D7-5C8-induced lysis. Together, this indicates that the Vγ9Vδ2-TCR can still detect phosphoantigens through sensing changes in the conformation of BTN3A1 when the bispecific antibody 1D7-5C8 is bound to the TCR.

Healthy B cells express low levels of CD1d (FIG. 12B). To test the effects of ABP on CLL and healthy B cells we performed mixed coculture experiments, in which B cells from healthy donors and CLL cells were pretreated with pamidronate for 2 hours and subsequently cultured for six hours with Vγ9Vδ2-T cells from a third donor in a 1:1:1 ratio in the presence of the bispecific anti-CD1d-Vδ2 VHH. Lysis of healthy B cells by Vγ9Vδ2-T cells was minimal, irrespective of ABP pretreatment and the presence of bispecific antibody 1D7-5C8 (10 pM bispecific antibody 1D7-5C8; no ABP: 4.8%±0.6, with ABP: 5.4%±4.5, FIG. 12C). In contrast, while Vγ9Vδ2-T cell lysis of CLL cells was triggered by the bispecific antibody 1D7-5C8, CLL cells were more prone to Vγ9Vδ2-T cell lysis in the presence of the bispecific antibody 1D7-5C8 following pamidronate pretreatment (10 pM bispecific antibody 1D7-5C8; no ABP: 19.6%±4.8, with ABP: 25.1%±5.2).

To further confirm the ability to recognize CD277 in the presence of the bispecific antibody 1D7-5C8 and to assess the relative contribution of bispecific antibody 1D7-5C8-induced versus CD277-Vγ9Vδ2 TCR-dependent target cell recognition, we evaluated the effect of blocking CD277 and CD1d. The bispecific antibody 1D7-5C8-induced cytotoxicity of Jeko-1 cells (29.6%±0.9, lysis without bispecific antibody 1D7-5C8 3.7%±1.3) was reduced 11.4% on average by a CD277-blocking antibody (clone 103.2 (Harly et al. (2012) Blood 120(11):2269), 18.2%±2.0), confirming a remaining role for ligand recognition by the Vγ9Vδ2-TCR (FIG. 12D). Bispecific antibody 1D7-5C8-induced lysis also decreased on average 15.9% with a CD1d-blocking antibody (to 13.7%±1.0), and declined by 20.2% when CD277 was simultaneously blocked (to 9.4%±0.8).

Taken together, these data indicate that the Vγ9Vδ2-TCR of Vγ9Vδ2-T cells bound to bispecific antibody 1D7-5C8 can still recognize phosphoantigen-induced conformational changes in CD277 on target cells allowing for the potential of a further increase in bispecific antibody 1D7-5C8-induced tumor cell lysis in the presence of ABP.

The invention claimed is:

1. A method of treating Chronic Lymphocytic Leukemia (CLL), Multiple Myeloma (MM), or Acute Myeloid Leukemia (AML) in a subject in need thereof comprising administering an antibody comprising
   (a) a first binding moiety that is able to bind human CD1d and comprises a complementarity determining region (CDR)1 comprising the amino acid sequence of SEQ ID NO: 34, a CDR2 comprising the amino acid sequence of SEQ ID NO: 35, and a CDR3 sequences comprising the amino acid sequence of SEQ ID NO: 36; and
   (b) a second binding moiety that is able to bind the human Vγ9Vδ2-TCR and comprises the amino acid sequence of SEQ ID NO: 162.

2. The method of claim 1, further comprising administering a compound capable of upregulating CD1d expression.

3. The method of claim 2, further comprising administering an EZH2 inhibitor.

4. The method of claim 1, further comprising administration of an aminobisphosphonate.

5. The method of claim 1, wherein the subject is above 65 years of age.

6. The method of claim 1, wherein the first and/or second binding moiety is a single domain antibody.

7. The method of claim 1, wherein the antibody is able to activate iNKT cells.

8. The method of claim 1, wherein the antibody is able to reduce Vδ1 T cell activation.

9. The method of claim 1, wherein the first binding moiety comprises SEQ ID NO: 161.

10. The method of claim 1, wherein the antibody is able to bind Vδ2.

11. The method of claim 1, wherein the antibody comprises the sequence set forth in SEQ ID NO: 164.

12. The method of claim 1, wherein the antibody further comprises a tumor targeting moiety.

13. The method of claim 2, wherein the compound capable of upregulating CD1d expression is all-trans retinoic acid.

* * * * *

SEQUENCE LISTING

```
<160> NUMBER OF SEQ ID NOS: 165

<210> SEQ ID NO 1
<211> LENGTH: 5
<212> TYPE: PRT
<213> ORGANISM: Artificial Sequence
<220> FEATURE:
<223> OTHER INFORMATION: antibody sequence

<400> SEQUENCE: 1

Ser Tyr Thr Met Gly
1               5

<210> SEQ ID NO 2
<211> LENGTH: 17
<212> TYPE: PRT
<213> ORGANISM: Artificial Sequence
<220> FEATURE:
<223> OTHER INFORMATION: antibody sequence

<400> SEQUENCE: 2

Ala Ile Arg Trp Ser Gly Glu Ser Pro Tyr Tyr Ala Asp Ser Val Lys
1               5                   10                  15

Gly

<210> SEQ ID NO 3
<211> LENGTH: 18
<212> TYPE: PRT
<213> ORGANISM: Artificial Sequence
<220> FEATURE:
<223> OTHER INFORMATION: antibody sequence

<400> SEQUENCE: 3

Arg Leu Val Pro Pro Gly Ile Pro Ile Glu Arg Ser Leu Glu Asn Met
1               5                   10                  15

Asn Tyr

<210> SEQ ID NO 4
<211> LENGTH: 5
<212> TYPE: PRT
<213> ORGANISM: Artificial Sequence
<220> FEATURE:
<223> OTHER INFORMATION: antibody sequence

<400> SEQUENCE: 4

Ser Tyr Thr Met Gly
1               5

<210> SEQ ID NO 5
<211> LENGTH: 17
<212> TYPE: PRT
<213> ORGANISM: Artificial Sequence
```

```
<220> FEATURE:
<223> OTHER INFORMATION: antibody sequence

<400> SEQUENCE: 5

Val Ile Arg Trp Ser Gly Glu Ser Pro Tyr Tyr Ala Asp Ser Val Lys
1               5                   10                  15

Gly

<210> SEQ ID NO 6
<211> LENGTH: 18
<212> TYPE: PRT
<213> ORGANISM: Artificial Sequence
<220> FEATURE:
<223> OTHER INFORMATION: antibody sequence

<400> SEQUENCE: 6

Arg Leu Val Pro Pro Gly Ile Pro Ile Glu Arg Thr Leu Glu Ser Met
1               5                   10                  15

Asn Tyr

<210> SEQ ID NO 7
<211> LENGTH: 5
<212> TYPE: PRT
<213> ORGANISM: Artificial Sequence
<220> FEATURE:
<223> OTHER INFORMATION: antibody sequence

<400> SEQUENCE: 7

Ser Tyr Thr Met Gly
1               5

<210> SEQ ID NO 8
<211> LENGTH: 17
<212> TYPE: PRT
<213> ORGANISM: Artificial Sequence
<220> FEATURE:
<223> OTHER INFORMATION: antibody sequence

<400> SEQUENCE: 8

Ala Ile Arg Trp Ser Gly Glu Ser Pro Ile Tyr Ala Asp Ser Val Lys
1               5                   10                  15

Gly

<210> SEQ ID NO 9
<211> LENGTH: 18
<212> TYPE: PRT
<213> ORGANISM: Artificial Sequence
<220> FEATURE:
<223> OTHER INFORMATION: antibody sequence

<400> SEQUENCE: 9

Arg Leu Val Pro Pro Gly Ile Pro Ile Glu Arg Thr Leu Glu Ser Met
1               5                   10                  15

Arg Tyr

<210> SEQ ID NO 10
<211> LENGTH: 5
<212> TYPE: PRT
<213> ORGANISM: Artificial Sequence
<220> FEATURE:
<223> OTHER INFORMATION: antibody sequence

<400> SEQUENCE: 10

Ser Tyr Thr Met Gly
```

-continued

<210> SEQ ID NO 11
<211> LENGTH: 17
<212> TYPE: PRT
<213> ORGANISM: Artificial Sequence
<220> FEATURE:
<223> OTHER INFORMATION: antibody sequence

<400> SEQUENCE: 11

Ala Ile Arg Trp Ser Gly Glu Ser Pro Tyr Tyr Ala Asp Ser Val Lys
1               5                   10                  15
Gly

<210> SEQ ID NO 12
<211> LENGTH: 18
<212> TYPE: PRT
<213> ORGANISM: Artificial Sequence
<220> FEATURE:
<223> OTHER INFORMATION: antibody sequence

<400> SEQUENCE: 12

Arg Leu Val Pro Pro Gly Ile Pro Ile Glu Arg Thr Leu Glu Ser Met
1               5                   10                  15
Lys Asp

<210> SEQ ID NO 13
<211> LENGTH: 5
<212> TYPE: PRT
<213> ORGANISM: Artificial Sequence
<220> FEATURE:
<223> OTHER INFORMATION: antibody sequence

<400> SEQUENCE: 13

Ser Tyr Thr Met Gly
1               5

<210> SEQ ID NO 14
<211> LENGTH: 17
<212> TYPE: PRT
<213> ORGANISM: Artificial Sequence
<220> FEATURE:
<223> OTHER INFORMATION: antibody sequence

<400> SEQUENCE: 14

Gly Ile Arg Trp Ser Asp Glu Ser Pro Ile Tyr Ala Asp Ser Val Lys
1               5                   10                  15
Gly

<210> SEQ ID NO 15
<211> LENGTH: 18
<212> TYPE: PRT
<213> ORGANISM: Artificial Sequence
<220> FEATURE:
<223> OTHER INFORMATION: antibody sequence

<400> SEQUENCE: 15

Arg Leu Val Pro Pro Gly Ile Pro Ile Pro Arg Thr Ser Glu Ser Met
1               5                   10                  15
Arg Tyr

<210> SEQ ID NO 16
<211> LENGTH: 5
<212> TYPE: PRT

```
<213> ORGANISM: Artificial Sequence
<220> FEATURE:
<223> OTHER INFORMATION: antibody sequence

<400> SEQUENCE: 16

Ser Tyr Thr Met Ala
1               5

<210> SEQ ID NO 17
<211> LENGTH: 17
<212> TYPE: PRT
<213> ORGANISM: Artificial Sequence
<220> FEATURE:
<223> OTHER INFORMATION: antibody sequence

<400> SEQUENCE: 17

Ala Ile Arg Trp Ser Gly Glu Ser Pro Ile Tyr Ala Asp Ser Val Lys
1               5                   10                  15

Gly

<210> SEQ ID NO 18
<211> LENGTH: 18
<212> TYPE: PRT
<213> ORGANISM: Artificial Sequence
<220> FEATURE:
<223> OTHER INFORMATION: antibody sequence

<400> SEQUENCE: 18

Arg Leu Val Pro Pro Gly Ile Pro Ile Glu Arg Thr Leu Glu Ser Met
1               5                   10                  15

Arg Tyr

<210> SEQ ID NO 19
<211> LENGTH: 5
<212> TYPE: PRT
<213> ORGANISM: Artificial Sequence
<220> FEATURE:
<223> OTHER INFORMATION: antibody sequence

<400> SEQUENCE: 19

Ser Tyr Thr Met Gly
1               5

<210> SEQ ID NO 20
<211> LENGTH: 17
<212> TYPE: PRT
<213> ORGANISM: Artificial Sequence
<220> FEATURE:
<223> OTHER INFORMATION: antibody sequence

<400> SEQUENCE: 20

Gly Ile Arg Trp Asp Asp Glu Asn Pro Tyr Tyr Ala Asp Ser Val Lys
1               5                   10                  15

Gly

<210> SEQ ID NO 21
<211> LENGTH: 18
<212> TYPE: PRT
<213> ORGANISM: Artificial Sequence
<220> FEATURE:
<223> OTHER INFORMATION: antibody sequence

<400> SEQUENCE: 21

Arg Leu Val Pro Pro Gly Ile Pro Phe Glu Arg Thr Leu Glu Asn Met
1               5                   10                  15
```

Arg Tyr

<210> SEQ ID NO 22
<211> LENGTH: 5
<212> TYPE: PRT
<213> ORGANISM: Artificial Sequence
<220> FEATURE:
<223> OTHER INFORMATION: antibody sequence

<400> SEQUENCE: 22

Ser Tyr Thr Met Gly
1               5

<210> SEQ ID NO 23
<211> LENGTH: 17
<212> TYPE: PRT
<213> ORGANISM: Artificial Sequence
<220> FEATURE:
<223> OTHER INFORMATION: antibody sequence

<400> SEQUENCE: 23

Ala Ile Arg Trp Asp Gly Glu Ser Pro Ile Tyr Ala Glu Ser Val Lys
1               5                   10                  15

Gly

<210> SEQ ID NO 24
<211> LENGTH: 18
<212> TYPE: PRT
<213> ORGANISM: Artificial Sequence
<220> FEATURE:
<223> OTHER INFORMATION: antibody sequence

<400> SEQUENCE: 24

Arg Leu Val Pro Pro Gly Ile Pro Ile Glu Arg Thr Leu Glu Ser Met
1               5                   10                  15

Arg Tyr

<210> SEQ ID NO 25
<211> LENGTH: 5
<212> TYPE: PRT
<213> ORGANISM: Artificial Sequence
<220> FEATURE:
<223> OTHER INFORMATION: antibody sequence

<400> SEQUENCE: 25

Ser Tyr Thr Met Gly
1               5

<210> SEQ ID NO 26
<211> LENGTH: 17
<212> TYPE: PRT
<213> ORGANISM: Artificial Sequence
<220> FEATURE:
<223> OTHER INFORMATION: antibody sequence

<400> SEQUENCE: 26

Val Ile Arg Trp Ser Gly Glu Ser Pro Tyr Tyr Ala Asp Ser Val Lys
1               5                   10                  15

Gly

<210> SEQ ID NO 27
<211> LENGTH: 18
<212> TYPE: PRT
<213> ORGANISM: Artificial Sequence

```
<220> FEATURE:
<223> OTHER INFORMATION: antibody sequence

<400> SEQUENCE: 27

Arg Leu Val Pro Pro Gly Ile Pro Ile Glu Arg Thr Leu Glu Ser Met
1               5                   10                  15

Asn Tyr

<210> SEQ ID NO 28
<211> LENGTH: 5
<212> TYPE: PRT
<213> ORGANISM: Artificial Sequence
<220> FEATURE:
<223> OTHER INFORMATION: antibody sequence

<400> SEQUENCE: 28

Ser Tyr Thr Met Gly
1               5

<210> SEQ ID NO 29
<211> LENGTH: 17
<212> TYPE: PRT
<213> ORGANISM: Artificial Sequence
<220> FEATURE:
<223> OTHER INFORMATION: antibody sequence

<400> SEQUENCE: 29

Ala Ile Arg Trp Ser Asp Glu Ser Pro Ile Tyr Ala Gly Ser Val Lys
1               5                   10                  15

Gly

<210> SEQ ID NO 30
<211> LENGTH: 18
<212> TYPE: PRT
<213> ORGANISM: Artificial Sequence
<220> FEATURE:
<223> OTHER INFORMATION: antibody sequence

<400> SEQUENCE: 30

Arg Leu Val Pro Pro Gly Ile Pro Ile Glu Arg Thr Leu Glu Ser Met
1               5                   10                  15

Arg Tyr

<210> SEQ ID NO 31
<211> LENGTH: 5
<212> TYPE: PRT
<213> ORGANISM: Artificial Sequence
<220> FEATURE:
<223> OTHER INFORMATION: antibody sequence

<400> SEQUENCE: 31

Ser Tyr Thr Met Gly
1               5

<210> SEQ ID NO 32
<211> LENGTH: 17
<212> TYPE: PRT
<213> ORGANISM: Artificial Sequence
<220> FEATURE:
<223> OTHER INFORMATION: antibody sequence

<400> SEQUENCE: 32

Ala Ile Arg Trp Ser Asp Glu Ser Pro Tyr Tyr Ser Asp Ser Val Lys
1               5                   10                  15
```

Gly

<210> SEQ ID NO 33
<211> LENGTH: 19
<212> TYPE: PRT
<213> ORGANISM: Artificial Sequence
<220> FEATURE:
<223> OTHER INFORMATION: antibody sequence

<400> SEQUENCE: 33

Arg Leu Val Pro Pro Gly Ile Pro Ile Glu Arg Thr Leu Glu Asn Met
1               5                   10                  15

Arg Tyr Ser

<210> SEQ ID NO 34
<211> LENGTH: 5
<212> TYPE: PRT
<213> ORGANISM: Artificial Sequence
<220> FEATURE:
<223> OTHER INFORMATION: antibody sequence

<400> SEQUENCE: 34

Asp Asn Val Met Gly
1               5

<210> SEQ ID NO 35
<211> LENGTH: 16
<212> TYPE: PRT
<213> ORGANISM: Artificial Sequence
<220> FEATURE:
<223> OTHER INFORMATION: antibody sequence

<400> SEQUENCE: 35

Thr Ile Arg Thr Gly Gly Ser Thr Asn Tyr Ala Asp Ser Val Lys Gly
1               5                   10                  15

<210> SEQ ID NO 36
<211> LENGTH: 11
<212> TYPE: PRT
<213> ORGANISM: Artificial Sequence
<220> FEATURE:
<223> OTHER INFORMATION: antibody sequence

<400> SEQUENCE: 36

Thr Ile Pro Val Pro Ser Thr Pro Tyr Asp Tyr
1               5                   10

<210> SEQ ID NO 37
<211> LENGTH: 5
<212> TYPE: PRT
<213> ORGANISM: Artificial Sequence
<220> FEATURE:
<223> OTHER INFORMATION: antibody sequence

<400> SEQUENCE: 37

Ser Tyr Thr Met Gly
1               5

<210> SEQ ID NO 38
<211> LENGTH: 17
<212> TYPE: PRT
<213> ORGANISM: Artificial Sequence
<220> FEATURE:
<223> OTHER INFORMATION: antibody sequence

<400> SEQUENCE: 38

```
Ala Ile Arg Trp Ser Gly Glu Ser Pro Tyr Tyr Ala Asp Ser Val Lys
1               5                   10                  15

Gly

<210> SEQ ID NO 39
<211> LENGTH: 18
<212> TYPE: PRT
<213> ORGANISM: Artificial Sequence
<220> FEATURE:
<223> OTHER INFORMATION: antibody sequence

<400> SEQUENCE: 39

Arg Leu Val Pro Pro Gly Ile Pro Ile Glu Arg Thr Leu Glu Asn Met
1               5                   10                  15

Asn Tyr

<210> SEQ ID NO 40
<211> LENGTH: 5
<212> TYPE: PRT
<213> ORGANISM: Artificial Sequence
<220> FEATURE:
<223> OTHER INFORMATION: antibody sequence

<400> SEQUENCE: 40

Ser Tyr Thr Met Gly
1               5

<210> SEQ ID NO 41
<211> LENGTH: 17
<212> TYPE: PRT
<213> ORGANISM: Artificial Sequence
<220> FEATURE:
<223> OTHER INFORMATION: antibody sequence

<400> SEQUENCE: 41

Ala Ile Arg Trp Ser Gly Glu Ser Pro Tyr Tyr Ala Asp Ser Val Lys
1               5                   10                  15

Gly

<210> SEQ ID NO 42
<211> LENGTH: 18
<212> TYPE: PRT
<213> ORGANISM: Artificial Sequence
<220> FEATURE:
<223> OTHER INFORMATION: antibody sequence

<400> SEQUENCE: 42

Arg Leu Val Pro Pro Gly Ile Pro Ile Glu Arg Thr Leu Glu Ser Met
1               5                   10                  15

Asn Tyr

<210> SEQ ID NO 43
<211> LENGTH: 5
<212> TYPE: PRT
<213> ORGANISM: Artificial Sequence
<220> FEATURE:
<223> OTHER INFORMATION: antibody sequence

<400> SEQUENCE: 43

Ser Tyr Thr Met Gly
1               5

<210> SEQ ID NO 44
<211> LENGTH: 17
```

```
<212> TYPE: PRT
<213> ORGANISM: Artificial Sequence
<220> FEATURE:
<223> OTHER INFORMATION: antibody sequence

<400> SEQUENCE: 44

Ala Ile Arg Trp Ser Gly Glu Ser Pro Ile Tyr Ala Asp Ser Val Lys
1               5                   10                  15

Gly

<210> SEQ ID NO 45
<211> LENGTH: 18
<212> TYPE: PRT
<213> ORGANISM: Artificial Sequence
<220> FEATURE:
<223> OTHER INFORMATION: antibody sequence

<400> SEQUENCE: 45

Arg Leu Val Pro Pro Gly Ile Pro Ile Glu Arg Thr Leu Glu Ser Met
1               5                   10                  15

Lys Asp

<210> SEQ ID NO 46
<211> LENGTH: 5
<212> TYPE: PRT
<213> ORGANISM: Artificial Sequence
<220> FEATURE:
<223> OTHER INFORMATION: antibody sequence

<400> SEQUENCE: 46

Ser Tyr Thr Met Thr
1               5

<210> SEQ ID NO 47
<211> LENGTH: 17
<212> TYPE: PRT
<213> ORGANISM: Artificial Sequence
<220> FEATURE:
<223> OTHER INFORMATION: antibody sequence

<400> SEQUENCE: 47

Gly Ile Arg Trp Ser Gly Glu Ser Pro Tyr Tyr Ala Asp Ser Val Lys
1               5                   10                  15

Gly

<210> SEQ ID NO 48
<211> LENGTH: 18
<212> TYPE: PRT
<213> ORGANISM: Artificial Sequence
<220> FEATURE:
<223> OTHER INFORMATION: antibody sequence

<400> SEQUENCE: 48

Arg Leu Val Pro Pro Gly Ile Pro Ile Glu Arg Thr Leu Glu Ser Met
1               5                   10                  15

Arg Tyr

<210> SEQ ID NO 49
<211> LENGTH: 5
<212> TYPE: PRT
<213> ORGANISM: Artificial Sequence
<220> FEATURE:
<223> OTHER INFORMATION: antibody sequence

<400> SEQUENCE: 49
```

Ser Tyr Thr Met Gly
1               5

<210> SEQ ID NO 50
<211> LENGTH: 17
<212> TYPE: PRT
<213> ORGANISM: Artificial Sequence
<220> FEATURE:
<223> OTHER INFORMATION: antibody sequence

<400> SEQUENCE: 50

Ala Ile Arg Trp Ser Gly Glu Ser Pro Tyr Tyr Gly Asp Ser Val Lys
1               5                   10                  15

Gly

<210> SEQ ID NO 51
<211> LENGTH: 18
<212> TYPE: PRT
<213> ORGANISM: Artificial Sequence
<220> FEATURE:
<223> OTHER INFORMATION: antibody sequence

<400> SEQUENCE: 51

Arg Leu Val Pro Pro Gly Ile Pro Ile Gly Arg Thr Leu Glu Ser Met
1               5                   10                  15

Asn Asn

<210> SEQ ID NO 52
<211> LENGTH: 5
<212> TYPE: PRT
<213> ORGANISM: Artificial Sequence
<220> FEATURE:
<223> OTHER INFORMATION: antibody sequence

<400> SEQUENCE: 52

Ser Tyr Thr Met Gly
1               5

<210> SEQ ID NO 53
<211> LENGTH: 17
<212> TYPE: PRT
<213> ORGANISM: Artificial Sequence
<220> FEATURE:
<223> OTHER INFORMATION: antibody sequence

<400> SEQUENCE: 53

Ala Ile Arg Trp Ser Gly Glu Ser Pro Tyr Tyr Ala Asp Ser Val Lys
1               5                   10                  15

Gly

<210> SEQ ID NO 54
<211> LENGTH: 18
<212> TYPE: PRT
<213> ORGANISM: Artificial Sequence
<220> FEATURE:
<223> OTHER INFORMATION: antibody sequence

<400> SEQUENCE: 54

Arg Leu Val Pro Pro Gly Ile Pro Ile Glu Arg Ala Leu Glu Asn Met
1               5                   10                  15

Asn Tyr

<210> SEQ ID NO 55

```
<211> LENGTH: 5
<212> TYPE: PRT
<213> ORGANISM: Artificial Sequence
<220> FEATURE:
<223> OTHER INFORMATION: antibody sequence

<400> SEQUENCE: 55

Ser Tyr Thr Met Gly
1               5

<210> SEQ ID NO 56
<211> LENGTH: 17
<212> TYPE: PRT
<213> ORGANISM: Artificial Sequence
<220> FEATURE:
<223> OTHER INFORMATION: antibody sequence

<400> SEQUENCE: 56

Ala Ile Arg Trp Ser Asp Glu Ser Pro Ile Tyr Ala Asp Ser Val Lys
1               5                   10                  15

Gly

<210> SEQ ID NO 57
<211> LENGTH: 18
<212> TYPE: PRT
<213> ORGANISM: Artificial Sequence
<220> FEATURE:
<223> OTHER INFORMATION: antibody sequence

<400> SEQUENCE: 57

Arg Leu Val Pro Pro Gly Ile Pro Ile Glu Arg Thr Leu Glu Ser Met
1               5                   10                  15

Arg Tyr

<210> SEQ ID NO 58
<211> LENGTH: 5
<212> TYPE: PRT
<213> ORGANISM: Artificial Sequence
<220> FEATURE:
<223> OTHER INFORMATION: antibody sequence

<400> SEQUENCE: 58

Ser Tyr Thr Met Gly
1               5

<210> SEQ ID NO 59
<211> LENGTH: 17
<212> TYPE: PRT
<213> ORGANISM: Artificial Sequence
<220> FEATURE:
<223> OTHER INFORMATION: antibody sequence

<400> SEQUENCE: 59

Ala Ile Arg Trp Ser Gly Glu Ser Pro Tyr Tyr Ala Asp Ser Val Lys
1               5                   10                  15

Gly

<210> SEQ ID NO 60
<211> LENGTH: 18
<212> TYPE: PRT
<213> ORGANISM: Artificial Sequence
<220> FEATURE:
<223> OTHER INFORMATION: antibody sequence

<400> SEQUENCE: 60
```

```
Arg Leu Val Pro Pro Gly Ile Pro Ile Glu Arg Ser Leu Glu Asn Met
1               5                   10                  15

Asn Tyr
```

```
<210> SEQ ID NO 61
<211> LENGTH: 4
<212> TYPE: PRT
<213> ORGANISM: Artificial Sequence
<220> FEATURE:
<223> OTHER INFORMATION: antibody sequence

<400> SEQUENCE: 61

Asn Ala Met Gly
1
```

```
<210> SEQ ID NO 62
<211> LENGTH: 16
<212> TYPE: PRT
<213> ORGANISM: Artificial Sequence
<220> FEATURE:
<223> OTHER INFORMATION: antibody sequence

<400> SEQUENCE: 62

Val Ile Ser Ser Ser Gly Ser Thr Asn Tyr Ala Asp Ser Val Lys Gly
1               5                   10                  15
```

```
<210> SEQ ID NO 63
<211> LENGTH: 10
<212> TYPE: PRT
<213> ORGANISM: Artificial Sequence
<220> FEATURE:
<223> OTHER INFORMATION: antibody sequence

<400> SEQUENCE: 63

His Val Ala Gly Phe Asp Glu Tyr Asn Tyr
1               5                   10
```

```
<210> SEQ ID NO 64
<211> LENGTH: 126
<212> TYPE: PRT
<213> ORGANISM: Artificial Sequence
<220> FEATURE:
<223> OTHER INFORMATION: antibody sequence

<400> SEQUENCE: 64

Val Gln Leu Val Glu Ser Gly Gly Gly Leu Val Gln Ala Gly Gly Ser
1               5                   10                  15

Leu Arg Leu Ser Cys Ala Ala Ser Gly Ser Ser Phe Ser Ser Tyr Thr
                20                  25                  30

Met Gly Trp Phe Arg Gln Ala Pro Gly Lys Glu Arg Glu Ile Val Ala
            35                  40                  45

Ala Ile Arg Trp Ser Gly Glu Ser Pro Tyr Tyr Ala Asp Ser Val Lys
        50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Phe Cys Ala
                85                  90                  95

Ala Arg Leu Val Pro Pro Gly Ile Pro Ile Glu Arg Ser Leu Glu Asn
                100                 105                 110

Met Asn Tyr Trp Gly Lys Gly Thr Leu Val Thr Val Ser Ser
            115                 120                 125
```

```
<210> SEQ ID NO 65
<211> LENGTH: 126
<212> TYPE: PRT
<213> ORGANISM: Artificial Sequence
<220> FEATURE:
<223> OTHER INFORMATION: antibody sequence

<400> SEQUENCE: 65

Val Gln Leu Val Glu Ser Gly Gly Ser Val Gln Ala Gly Gly Ser
1               5                   10                  15

Leu Arg Leu Ser Cys Ala Ala Ser Gly Arg Ser Phe Ser Ser Tyr Thr
            20                  25                  30

Met Gly Trp Cys Arg Gln Ala Pro Gly Lys Glu Arg Glu Cys Val Ala
        35                  40                  45

Val Ile Arg Trp Ser Gly Glu Ser Pro Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Arg Leu Val Pro Pro Gly Ile Pro Ile Glu Arg Thr Leu Glu Ser
            100                 105                 110

Met Asn Tyr Trp Gly Lys Gly Thr Leu Val Thr Val Ser Ser
        115                 120                 125

<210> SEQ ID NO 66
<211> LENGTH: 127
<212> TYPE: PRT
<213> ORGANISM: Artificial Sequence
<220> FEATURE:
<223> OTHER INFORMATION: antibody sequence

<400> SEQUENCE: 66

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ser Phe Ser Ser Tyr
            20                  25                  30

Thr Met Gly Trp Phe Arg Gln Ala Pro Gly Lys Glu Arg Glu Ile Val
        35                  40                  45

Ala Ala Ile Arg Trp Ser Gly Glu Ser Pro Ile Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Ala Arg Leu Val Pro Pro Gly Ile Pro Ile Glu Arg Thr Leu Glu
            100                 105                 110

Ser Met Arg Tyr Trp Gly Lys Gly Thr Leu Val Thr Val Ser Ser
        115                 120                 125

<210> SEQ ID NO 67
<211> LENGTH: 130
<212> TYPE: PRT
<213> ORGANISM: Artificial Sequence
<220> FEATURE:
<223> OTHER INFORMATION: antibody sequence

<400> SEQUENCE: 67

Glu Val Gln Leu Val Glu Ser Gly Gly Gly Leu Val Gln Ala Gly Gly
1               5                   10                  15
```

Ser Leu Gly Leu Ser Cys Ala Ala Ser Gly Arg Ser Phe Ser Ser Tyr
            20                  25                  30

Thr Met Gly Val Ile Arg Trp Ser Gly Glu Ser Pro Tyr Tyr Ala Asp
            35                  40                  45

Ser Val Lys Gly Ala Ile Arg Trp Ser Gly Glu Ser Pro Tyr Tyr Ala
 50                  55                  60

Asp Ser Val Lys Gly Arg Phe Thr Ile Ser Arg Asp Asn Ala Lys Asn
 65                  70                  75                  80

Thr Leu Tyr Leu Gln Met Asn Asn Leu Lys Pro Glu Asp Thr Ala Val
            85                  90                  95

Tyr Tyr Cys Ala Ala Arg Leu Val Pro Pro Gly Ile Pro Ile Glu Arg
            100                 105                 110

Thr Leu Glu Ser Met Lys Asp Trp Gly Lys Gly Thr Leu Val Thr Val
            115                 120                 125

Ser Ser
130

<210> SEQ ID NO 68
<211> LENGTH: 129
<212> TYPE: PRT
<213> ORGANISM: Artificial Sequence
<220> FEATURE:
<223> OTHER INFORMATION: antibody sequence

<400> SEQUENCE: 68

Val Gln Leu Val Glu Ser Gly Gly Gly Leu Val Gln Ala Gly Gly Ser
 1               5                   10                  15

Leu Arg Leu Ser Cys Ala Ala Ser Gly Ser Ser Phe Ser Ser Tyr Thr
            20                  25                  30

Met Gly Ala Ile Arg Trp Ser Asp Glu Ser Pro Ile Tyr Ala Gly Ser
            35                  40                  45

Val Lys Gly Gly Ile Arg Trp Ser Asp Glu Ser Pro Ile Tyr Ala Asp
 50                  55                  60

Ser Val Lys Gly Arg Phe Thr Ile Ser Arg Asp Asn Ala Lys Asn Thr
 65                  70                  75                  80

Leu Tyr Leu Gln Met Asn Ser Leu Lys Pro Glu Asp Thr Ala Val Tyr
            85                  90                  95

Tyr Cys Ala Ala Arg Leu Val Pro Pro Gly Ile Pro Ile Pro Arg Thr
            100                 105                 110

Ser Glu Ser Met Arg Tyr Trp Gly Lys Gly Thr Leu Val Thr Val Ser
            115                 120                 125

Ser

<210> SEQ ID NO 69
<211> LENGTH: 130
<212> TYPE: PRT
<213> ORGANISM: Artificial Sequence
<220> FEATURE:
<223> OTHER INFORMATION: antibody sequence

<400> SEQUENCE: 69

Gln Val Gln Leu Val Glu Ser Gly Gly Gly Leu Val Gln Ala Gly Asp
 1               5                   10                  15

Ser Leu Arg Leu Ser Cys Ala Ala Ser Gly Ser Ser Phe Ser Ser Tyr
            20                  25                  30

Thr Met Ala Ala Ile Arg Trp Ser Asp Glu Ser Pro Tyr Tyr Ser Asp
            35                  40                  45

```
Ser Val Lys Gly Ala Ile Arg Trp Ser Gly Glu Ser Pro Ile Tyr Ala
     50                  55                  60

Asp Ser Val Lys Gly Arg Phe Thr Ile Ser Arg Asp Asn Ala Lys Asn
 65                  70                  75                  80

Thr Leu Tyr Leu Gln Met Asn Ser Leu Lys Pro Glu Asp Thr Ala Val
                 85                  90                  95

Tyr Asn Cys Ala Ala Arg Leu Val Pro Pro Gly Ile Pro Ile Glu Arg
            100                 105                 110

Thr Leu Glu Ser Met Arg Tyr Trp Gly Lys Gly Thr Leu Val Thr Val
            115                 120                 125

Ser Ser
    130

<210> SEQ ID NO 70
<211> LENGTH: 129
<212> TYPE: PRT
<213> ORGANISM: Artificial Sequence
<220> FEATURE:
<223> OTHER INFORMATION: antibody sequence

<400> SEQUENCE: 70

Glu Val Gln Leu Val Glu Ser Gly Gly Gly Leu Val Gln Ala Gly Gly
 1               5                  10                  15

Ser Leu Arg Leu Ser Cys Ala Ala Ser Val Ser Ser Phe Ser Ser Tyr
             20                  25                  30

Thr Met Gly Thr Ile Arg Thr Gly Gly Ser Thr Asn Tyr Ala Asp Ser
         35                  40                  45

Val Lys Gly Gly Ile Arg Trp Asp Asp Glu Asn Pro Tyr Tyr Ala Asp
     50                  55                  60

Ser Val Lys Gly Arg Phe Thr Ile Ser Arg Asp Asn Ala Lys Asn Thr
 65                  70                  75                  80

Leu Tyr Leu Gln Met Asn Ser Leu Lys Pro Glu Asp Thr Ala Asn Tyr
                 85                  90                  95

Tyr Cys Ala Ala Arg Leu Val Pro Pro Gly Ile Pro Phe Glu Arg Thr
            100                 105                 110

Leu Glu Asn Met Arg Tyr Trp Gly Lys Gly Thr Leu Val Thr Val Ser
            115                 120                 125

Ser

<210> SEQ ID NO 71
<211> LENGTH: 130
<212> TYPE: PRT
<213> ORGANISM: Artificial Sequence
<220> FEATURE:
<223> OTHER INFORMATION: antibody sequence

<400> SEQUENCE: 71

Glu Val Gln Leu Val Glu Ser Gly Gly Gly Leu Val Gln Ala Gly Gly
 1               5                  10                  15

Ser Leu Arg Leu Ser Cys Ala Ala Ser Gly Ser Ser Phe Ser Ser Tyr
             20                  25                  30

Thr Met Gly Ala Ile Arg Trp Ser Gly Glu Ser Pro Tyr Tyr Ala Asp
         35                  40                  45

Ser Val Lys Gly Ala Ile Arg Trp Asp Gly Glu Ser Pro Ile Tyr Ala
     50                  55                  60

Glu Ser Val Lys Gly Arg Phe Thr Ile Ser Arg Asp Asn Ala Lys Asn
 65                  70                  75                  80
```

Thr Leu Tyr Leu Gln Met Asn Ser Leu Lys Pro Glu Asp Thr Ala Val
                85                  90                  95

Tyr Tyr Cys Ala Ala Arg Leu Val Pro Pro Gly Ile Pro Ile Glu Arg
            100                 105                 110

Thr Leu Glu Ser Met Arg Tyr Trp Gly Lys Gly Thr Leu Val Thr Val
        115                 120                 125

Ser Ser
    130

<210> SEQ ID NO 72
<211> LENGTH: 130
<212> TYPE: PRT
<213> ORGANISM: Artificial Sequence
<220> FEATURE:
<223> OTHER INFORMATION: antibody sequence

<400> SEQUENCE: 72

Glu Val Gln Leu Val Glu Ser Gly Gly Ser Val Gln Ala Gly Gly
1               5                   10                  15

Ser Leu Arg Leu Ser Cys Ala Ala Ser Gly Arg Ser Phe Ser Ser Tyr
            20                  25                  30

Thr Met Gly Ala Ile Arg Trp Ser Gly Glu Ser Pro Tyr Tyr Ala Asp
        35                  40                  45

Ser Val Lys Gly Val Ile Arg Trp Ser Gly Glu Ser Pro Tyr Tyr Ala
    50                  55                  60

Asp Ser Val Lys Gly Arg Phe Thr Ile Ser Arg Asp Asn Ala Lys Asn
65                  70                  75                  80

Thr Val Tyr Leu Gln Met Ala Ser Leu Lys Pro Asp Asp Thr Ala Val
                85                  90                  95

Tyr Tyr Cys Ala Ala Arg Leu Val Pro Pro Gly Ile Pro Ile Glu Arg
            100                 105                 110

Thr Leu Glu Ser Met Asn Tyr Trp Gly Lys Gly Thr Leu Val Thr Val
        115                 120                 125

Ser Ser
    130

<210> SEQ ID NO 73
<211> LENGTH: 130
<212> TYPE: PRT
<213> ORGANISM: Artificial Sequence
<220> FEATURE:
<223> OTHER INFORMATION: antibody sequence

<400> SEQUENCE: 73

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ser Phe Ser Ser Tyr
            20                  25                  30

Thr Met Gly Ala Ile Arg Trp Ser Gly Glu Ser Pro Tyr Tyr Ala Asp
        35                  40                  45

Ser Val Lys Gly Ala Ile Arg Trp Ser Asp Glu Ser Pro Ile Tyr Ala
    50                  55                  60

Gly Ser Val Lys Gly Arg Phe Thr Ile Ser Arg Asp Asn Ala Lys Asn
65                  70                  75                  80

Thr Leu Tyr Leu Gln Met Asn Ser Leu Lys Pro Glu Asp Thr Ala Val
                85                  90                  95

Tyr Tyr Cys Ala Ala Arg Leu Val Pro Pro Gly Ile Pro Ile Glu Arg

```
                100                 105                 110
Thr Leu Glu Ser Met Arg Tyr Trp Gly Lys Gly Thr Leu Val Thr Val
            115                 120                 125
Ser Ser
    130

<210> SEQ ID NO 74
<211> LENGTH: 129
<212> TYPE: PRT
<213> ORGANISM: Artificial Sequence
<220> FEATURE:
<223> OTHER INFORMATION: antibody sequence

<400> SEQUENCE: 74

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ser Phe Ser Ser Tyr
            20                  25                  30

Thr Met Gly Ser Ile Asn Asn Gly Gly Ser Thr Lys Tyr Ala Asp Ser
        35                  40                  45

Val Lys Gly Ala Ile Arg Trp Ser Asp Glu Ser Pro Tyr Tyr Ser Asp
    50                  55                  60

Ser Val Lys Gly Arg Phe Thr Ile Ser Arg Asp Asn Ala Lys Asn Thr
65                  70                  75                  80

Leu Tyr Leu Gln Met Asn Ser Leu Lys Pro Glu Asp Thr Ala Val Tyr
                85                  90                  95

Tyr Cys Ser Ala Arg Leu Val Pro Pro Gly Ile Pro Ile Glu Arg Thr
            100                 105                 110

Leu Glu Asn Met Arg Tyr Ser Gly Lys Gly Thr Leu Val Thr Val Ser
        115                 120                 125

Ser

<210> SEQ ID NO 75
<211> LENGTH: 122
<212> TYPE: PRT
<213> ORGANISM: Artificial Sequence
<220> FEATURE:
<223> OTHER INFORMATION: antibody sequence

<400> SEQUENCE: 75

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Met Phe Ser Asp Asn
            20                  25                  30

Val Met Gly Ala Ile Arg Trp Ser Gly Glu Ser Pro Tyr Tyr Val Asp
        35                  40                  45

Ser Val Lys Gly Thr Ile Arg Thr Gly Gly Ser Thr Asn Tyr Ala Asp
    50                  55                  60

Ser Val Lys Gly Arg Phe Thr Ile Ser Arg Asp Asn Ala Lys Asn Thr
65                  70                  75                  80

Val Tyr Leu Gln Met Asn Ser Leu Lys Pro Glu Asp Thr Ala Val Tyr
                85                  90                  95

Tyr Cys Arg His Thr Ile Pro Val Pro Ser Thr Pro Tyr Asp Tyr Trp
            100                 105                 110

Gly Gln Gly Thr Gln Val Thr Val Ser Ser
        115                 120
```

```
<210> SEQ ID NO 76
<211> LENGTH: 130
<212> TYPE: PRT
<213> ORGANISM: Artificial Sequence
<220> FEATURE:
<223> OTHER INFORMATION: antibody sequence

<400> SEQUENCE: 76

Gln Val Gln Leu Val Glu Ser Gly Gly Gly Leu Val Gln Ala Gly Gly
1               5                   10                  15

Ser Leu Gly Leu Ser Cys Ala Ala Ser Gly Arg Ser Phe Ser Ser Tyr
            20                  25                  30

Thr Met Gly Ala Ile Arg Trp Ser Gly Glu Ser Pro Ile Tyr Ala Asp
        35                  40                  45

Ser Val Lys Gly Ala Ile Arg Trp Ser Gly Glu Ser Pro Tyr Tyr Ala
    50                  55                  60

Asp Ser Val Lys Gly Arg Phe Thr Ile Ser Arg Asp Asn Ala Lys Asn
65                  70                  75                  80

Thr Leu Tyr Leu Gln Met Asn Ser Leu Lys Pro Glu Asp Thr Ala Val
                85                  90                  95

Tyr Tyr Cys Ala Ala Arg Leu Val Pro Pro Gly Ile Pro Ile Glu Arg
            100                 105                 110

Thr Leu Glu Asn Met Asn Tyr Trp Gly Lys Gly Thr Leu Val Thr Val
        115                 120                 125

Ser Ser
    130

<210> SEQ ID NO 77
<211> LENGTH: 129
<212> TYPE: PRT
<213> ORGANISM: Artificial Sequence
<220> FEATURE:
<223> OTHER INFORMATION: antibody sequence

<400> SEQUENCE: 77

Val Gln Leu Val Glu Ser Gly Gly Gly Leu Val Gln Ala Gly Gly Ser
1               5                   10                  15

Leu Arg Leu Ser Cys Ala Ala Ser Gly Ser Ser Phe Ser Ser Tyr Thr
            20                  25                  30

Met Gly Gly Ile Arg Trp Ser Gly Glu Ser Pro Tyr Tyr Ala Asp Ser
        35                  40                  45

Val Lys Gly Ala Ile Arg Trp Ser Gly Glu Ser Pro Tyr Tyr Ala Asp
    50                  55                  60

Ser Val Lys Gly Arg Phe Thr Ile Ser Arg Asp Asn Ala Lys Asn Thr
65                  70                  75                  80

Leu Tyr Leu Gln Met Asn Ser Leu Lys Pro Glu Asp Thr Ala Val Tyr
                85                  90                  95

Tyr Cys Ala Ala Arg Leu Val Pro Pro Gly Ile Pro Ile Glu Arg Thr
            100                 105                 110

Leu Glu Ser Met Asn Tyr Trp Gly Lys Gly Thr Leu Val Thr Val Ser
        115                 120                 125

Ser

<210> SEQ ID NO 78
<211> LENGTH: 130
<212> TYPE: PRT
<213> ORGANISM: Artificial Sequence
<220> FEATURE:
<223> OTHER INFORMATION: antibody sequence
```

<400> SEQUENCE: 78

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ser Phe Ser Ser Tyr
            20                  25                  30

Thr Met Gly Ala Ile Arg Trp Ser Gly Glu Ser Pro Tyr Tyr Ala Asp
        35                  40                  45

Ser Val Lys Gly Ala Ile Arg Trp Ser Gly Glu Ser Pro Ile Tyr Ala
50                  55                  60

Asp Ser Val Lys Gly Arg Phe Thr Ile Ser Arg Asp Asn Ala Lys Asn
65                  70                  75                  80

Thr Leu Tyr Leu Gln Met Asn Ser Leu Lys Pro Glu Asp Thr Ala Val
                85                  90                  95

Tyr Tyr Cys Ala Ala Arg Leu Val Pro Pro Gly Ile Pro Ile Glu Arg
            100                 105                 110

Thr Leu Glu Ser Met Lys Asp Trp Gly Lys Gly Thr Leu Val Thr Val
        115                 120                 125

Ser Ser
130

<210> SEQ ID NO 79
<211> LENGTH: 129
<212> TYPE: PRT
<213> ORGANISM: Artificial Sequence
<220> FEATURE:
<223> OTHER INFORMATION: antibody sequence

<400> SEQUENCE: 79

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ser Phe Ser Ser Tyr
            20                  25                  30

Thr Met Thr Val Ile Ser Ser Ser Gly Ser Thr Asn Tyr Ala Asp Ser
        35                  40                  45

Val Lys Gly Gly Ile Arg Trp Ser Gly Glu Ser Pro Tyr Tyr Ala Asp
    50                  55                  60

Ser Val Lys Gly Arg Phe Thr Ile Ser Arg Asp Asn Ala Lys Asn Thr
65                  70                  75                  80

Leu Tyr Leu Gln Met Asn Ser Leu Lys Pro Glu Asp Thr Ala Val Tyr
                85                  90                  95

Tyr Cys Ala Ala Arg Leu Val Pro Pro Gly Ile Pro Ile Glu Arg Thr
            100                 105                 110

Leu Glu Ser Met Arg Tyr Trp Gly Lys Gly Thr Leu Val Thr Val Ser
        115                 120                 125

Ser

<210> SEQ ID NO 80
<211> LENGTH: 129
<212> TYPE: PRT
<213> ORGANISM: Artificial Sequence
<220> FEATURE:
<223> OTHER INFORMATION: antibody sequence

<400> SEQUENCE: 80

Val Gln Leu Val Glu Ser Gly Gly Gly Leu Val Gln Ala Gly Gly Ser
1               5                   10                  15

Leu Arg Leu Ser Cys Ala Ala Ser Gly Ser Ser Phe Ser Ser Tyr Thr
         20                  25                  30

Met Gly Val Ile Arg Trp Ser Gly Glu Ser Pro Tyr Tyr Ala Asp Ser
         35                  40                  45

Val Lys Gly Ala Ile Arg Trp Ser Gly Glu Ser Pro Tyr Tyr Gly Asp
 50                  55                  60

Ser Val Lys Gly Arg Phe Thr Ile Ser Arg Asp Asn Ala Lys Asn Thr
 65                  70                  75                  80

Leu Tyr Leu Gln Met Asn Ser Leu Lys Pro Glu Asp Thr Ala Val Tyr
             85                  90                  95

Tyr Cys Ala Ala Arg Leu Val Pro Pro Gly Ile Pro Ile Gly Arg Thr
            100                 105                 110

Leu Glu Ser Met Asn Asn Trp Gly Lys Gly Thr Leu Val Thr Val Ser
        115                 120                 125

Ser

<210> SEQ ID NO 81
<211> LENGTH: 130
<212> TYPE: PRT
<213> ORGANISM: Artificial Sequence
<220> FEATURE:
<223> OTHER INFORMATION: antibody sequence

<400> SEQUENCE: 81

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ser Phe Ser Ser Tyr
            20                  25                  30

Thr Met Gly Ala Ile Arg Trp Ser Asp Glu Ser Pro Ile Tyr Ala Gly
         35                  40                  45

Ser Val Lys Gly Ala Ile Arg Trp Ser Gly Glu Ser Pro Tyr Tyr Ala
 50                  55                  60

Asp Ser Val Lys Gly Arg Phe Thr Ile Ser Arg Asp Asn Ala Lys Asn
65                   70                  75                  80

Thr Leu Tyr Leu Gln Met His Ser Leu Lys Pro Glu Asp Thr Ala Val
             85                  90                  95

Tyr Tyr Cys Ala Ala Arg Leu Val Pro Pro Gly Ile Pro Ile Glu Arg
            100                 105                 110

Ala Leu Glu Asn Met Asn Tyr Trp Gly Lys Gly Thr Leu Val Thr Val
        115                 120                 125

Ser Ser
    130

<210> SEQ ID NO 82
<211> LENGTH: 130
<212> TYPE: PRT
<213> ORGANISM: Artificial Sequence
<220> FEATURE:
<223> OTHER INFORMATION: antibody sequence

<400> SEQUENCE: 82

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ser Phe Ser Ser Tyr
            20                  25                  30

Thr Met Gly Ala Ile Arg Trp Ser Asp Glu Ser Pro Tyr Tyr Ser Asp
         35                  40                  45

Ser Val Lys Gly Ala Ile Arg Trp Ser Asp Glu Ser Pro Ile Tyr Ala
    50                  55                  60

Asp Ser Val Lys Gly Arg Phe Thr Ile Ser Arg Asp Asn Ala Lys Asn
65                  70                  75                  80

Thr Leu Tyr Leu Gln Met His Ser Leu Lys Pro Glu Asp Thr Ala Phe
                85                  90                  95

Tyr Tyr Cys Ala Ala Arg Leu Val Pro Pro Gly Ile Pro Ile Glu Arg
            100                 105                 110

Thr Leu Glu Ser Met Arg Tyr Trp Gly Lys Gly Thr Leu Val Thr Val
        115                 120                 125

Ser Ser
    130

<210> SEQ ID NO 83
<211> LENGTH: 129
<212> TYPE: PRT
<213> ORGANISM: Artificial Sequence
<220> FEATURE:
<223> OTHER INFORMATION: antibody sequence

<400> SEQUENCE: 83

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Phe Ser Ser Tyr
            20                  25                  30

Thr Met Gly Thr Ile Arg Thr Gly Gly Ser Thr Asn Tyr Ala Asp Ser
        35                  40                  45

Val Lys Gly Ala Ile Arg Trp Ser Gly Glu Ser Pro Tyr Tyr Ala Asp
    50                  55                  60

Ser Val Lys Gly Arg Phe Thr Ile Ser Arg Asp Asn Ala Lys Asn Thr
65                  70                  75                  80

Asn Tyr Leu Gln Met Asn Ser Leu Lys Pro Glu Leu Thr Ala Val Tyr
                85                  90                  95

Tyr Cys Ala Ala Arg Leu Val Pro Pro Gly Ile Pro Ile Glu Arg Ser
            100                 105                 110

Leu Glu Asn Met Asn Tyr Trp Gly Lys Gly Thr Leu Val Thr Val Ser
        115                 120                 125

Ser

<210> SEQ ID NO 84
<211> LENGTH: 121
<212> TYPE: PRT
<213> ORGANISM: Artificial Sequence
<220> FEATURE:
<223> OTHER INFORMATION: antibody sequence

<400> SEQUENCE: 84

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Ile Asn
            20                  25                  30

Ala Met Gly Ala Ile Arg Trp Ser Gly Glu Ser Pro Tyr Tyr Ala Asp
        35                  40                  45

Ser Val Lys Gly Val Ile Ser Ser Gly Ser Thr Asn Tyr Ala Asp
    50                  55                  60

Ser Val Lys Gly Arg Phe Thr Ile Ser Arg Asp Asn Ala Lys Asn Thr
65                  70                  75                  80

Ala Tyr Leu Gln Met Asn Ser Leu Lys Val Glu Asp Thr Ala Val Tyr
            85                  90                  95

Tyr Cys Ala Ala His Val Ala Gly Phe Asp Glu Tyr Asn Tyr Trp Gly
        100                 105                 110

Gln Gly Thr Gln Val Thr Val Ser Ser
        115                 120

<210> SEQ ID NO 85
<211> LENGTH: 5
<212> TYPE: PRT
<213> ORGANISM: Artificial Sequence
<220> FEATURE:
<223> OTHER INFORMATION: antibody sequence

<400> SEQUENCE: 85

Ser Tyr Ala Met Gly
1               5

<210> SEQ ID NO 86
<211> LENGTH: 17
<212> TYPE: PRT
<213> ORGANISM: Artificial Sequence
<220> FEATURE:
<223> OTHER INFORMATION: antibody sequence

<400> SEQUENCE: 86

Ala Ile Ser Trp Ser Gly Gly Thr Thr Tyr Tyr Ala Asp Ser Val Lys
1               5                   10                  15

Gly

<210> SEQ ID NO 87
<211> LENGTH: 16
<212> TYPE: PRT
<213> ORGANISM: Artificial Sequence
<220> FEATURE:
<223> OTHER INFORMATION: antibody sequence

<400> SEQUENCE: 87

Ser Leu Asp Cys Ser Gly Pro Gly Cys His Thr Ala Glu Tyr Asp Tyr
1               5                   10                  15

<210> SEQ ID NO 88
<211> LENGTH: 5
<212> TYPE: PRT
<213> ORGANISM: Artificial Sequence
<220> FEATURE:
<223> OTHER INFORMATION: antibody sequence

<400> SEQUENCE: 88

Glu Tyr Ala Met Gly
1               5

<210> SEQ ID NO 89
<211> LENGTH: 17
<212> TYPE: PRT
<213> ORGANISM: Artificial Sequence
<220> FEATURE:
<223> OTHER INFORMATION: antibody sequence

<400> SEQUENCE: 89

Ala Ile Ser Trp Thr Gly Ser Lys Thr Tyr Tyr Ala Asp Ser Val Lys
1               5                   10                  15

Gly

```
<210> SEQ ID NO 90
<211> LENGTH: 16
<212> TYPE: PRT
<213> ORGANISM: Artificial Sequence
<220> FEATURE:
<223> OTHER INFORMATION: antibody sequence

<400> SEQUENCE: 90

Ser Ser Asp Cys Ser Gly Pro Gly Cys His Thr Glu Glu Tyr Asp Tyr
1               5                   10                  15

<210> SEQ ID NO 91
<211> LENGTH: 5
<212> TYPE: PRT
<213> ORGANISM: Artificial Sequence
<220> FEATURE:
<223> OTHER INFORMATION: antibody sequence

<400> SEQUENCE: 91

Ser Tyr Ala Met Gly
1               5

<210> SEQ ID NO 92
<211> LENGTH: 17
<212> TYPE: PRT
<213> ORGANISM: Artificial Sequence
<220> FEATURE:
<223> OTHER INFORMATION: antibody sequence

<400> SEQUENCE: 92

Ala Val Ser Trp Ser Gly Gly Ser Thr Tyr Tyr Ala Asp Ser Val Lys
1               5                   10                  15

Gly

<210> SEQ ID NO 93
<211> LENGTH: 16
<212> TYPE: PRT
<213> ORGANISM: Artificial Sequence
<220> FEATURE:
<223> OTHER INFORMATION: antibody sequence

<400> SEQUENCE: 93

Ser Gln Asp Cys Ser Gly Pro Gly Cys Tyr Thr Asn Glu Tyr Asp Ser
1               5                   10                  15

<210> SEQ ID NO 94
<211> LENGTH: 5
<212> TYPE: PRT
<213> ORGANISM: Artificial Sequence
<220> FEATURE:
<223> OTHER INFORMATION: antibody sequence

<400> SEQUENCE: 94

Asn Tyr Ala Met Ala
1               5

<210> SEQ ID NO 95
<211> LENGTH: 17
<212> TYPE: PRT
<213> ORGANISM: Artificial Sequence
<220> FEATURE:
<223> OTHER INFORMATION: antibody sequence

<400> SEQUENCE: 95

Ala Val Ser Trp Ser Gly Gly Arg Thr Tyr Tyr Ala Asp Ser Val Lys
1               5                   10                  15
```

Gly

<210> SEQ ID NO 96
<211> LENGTH: 16
<212> TYPE: PRT
<213> ORGANISM: Artificial Sequence
<220> FEATURE:
<223> OTHER INFORMATION: antibody sequence

<400> SEQUENCE: 96

Ser Leu Ser Cys Ser Gly Pro Gly Cys Ser Leu Glu Glu Tyr Asp Tyr
1               5                   10                  15

<210> SEQ ID NO 97
<211> LENGTH: 5
<212> TYPE: PRT
<213> ORGANISM: Artificial Sequence
<220> FEATURE:
<223> OTHER INFORMATION: antibody sequence

<400> SEQUENCE: 97

Asn Tyr Ala Met Gly
1               5

<210> SEQ ID NO 98
<211> LENGTH: 17
<212> TYPE: PRT
<213> ORGANISM: Artificial Sequence
<220> FEATURE:
<223> OTHER INFORMATION: antibody sequence

<400> SEQUENCE: 98

Val Ile Ser Trp Ser Gly Gly Ser Thr Tyr Tyr Ala Asp Ser Val Lys
1               5                   10                  15

Gly

<210> SEQ ID NO 99
<211> LENGTH: 18
<212> TYPE: PRT
<213> ORGANISM: Artificial Sequence
<220> FEATURE:
<223> OTHER INFORMATION: antibody sequence

<400> SEQUENCE: 99

Gln Phe Ser Gly Ala Ser Thr Val Val Ala Gly Thr Ala Leu Asp Tyr
1               5                   10                  15

Asp Tyr

<210> SEQ ID NO 100
<211> LENGTH: 5
<212> TYPE: PRT
<213> ORGANISM: Artificial Sequence
<220> FEATURE:
<223> OTHER INFORMATION: antibody sequence

<400> SEQUENCE: 100

Asn Tyr Gly Met Gly
1               5

<210> SEQ ID NO 101
<211> LENGTH: 17
<212> TYPE: PRT
<213> ORGANISM: Artificial Sequence
<220> FEATURE:
<223> OTHER INFORMATION: antibody sequence

```
<400> SEQUENCE: 101

Gly Ile Ser Trp Ser Gly Gly Ser Thr Asp Tyr Ala Asp Ser Val Lys
1               5                   10                  15

Gly

<210> SEQ ID NO 102
<211> LENGTH: 17
<212> TYPE: PRT
<213> ORGANISM: Artificial Sequence
<220> FEATURE:
<223> OTHER INFORMATION: antibody sequence

<400> SEQUENCE: 102

Val Phe Ser Gly Ala Glu Thr Ala Tyr Tyr Pro Ser Asp Asp Tyr Asp
1               5                   10                  15

Tyr

<210> SEQ ID NO 103
<211> LENGTH: 5
<212> TYPE: PRT
<213> ORGANISM: Artificial Sequence
<220> FEATURE:
<223> OTHER INFORMATION: antibody sequence

<400> SEQUENCE: 103

Asn Tyr Gly Met Gly
1               5

<210> SEQ ID NO 104
<211> LENGTH: 17
<212> TYPE: PRT
<213> ORGANISM: Artificial Sequence
<220> FEATURE:
<223> OTHER INFORMATION: antibody sequence

<400> SEQUENCE: 104

Gly Ile Ser Trp Ser Gly Gly Ser Thr Asp Tyr Ala Asp Ser Val Lys
1               5                   10                  15

Gly

<210> SEQ ID NO 105
<211> LENGTH: 17
<212> TYPE: PRT
<213> ORGANISM: Artificial Sequence
<220> FEATURE:
<223> OTHER INFORMATION: antibody sequence

<400> SEQUENCE: 105

Val Phe Ser Gly Ala Glu Thr Ala Tyr Tyr Pro Ser Asp Asp Tyr Asp
1               5                   10                  15

Tyr

<210> SEQ ID NO 106
<211> LENGTH: 5
<212> TYPE: PRT
<213> ORGANISM: Artificial Sequence
<220> FEATURE:
<223> OTHER INFORMATION: antibody sequence

<400> SEQUENCE: 106

Asn Tyr Gly Met Gly
1               5
```

```
<210> SEQ ID NO 107
<211> LENGTH: 17
<212> TYPE: PRT
<213> ORGANISM: Artificial Sequence
<220> FEATURE:
<223> OTHER INFORMATION: antibody sequence

<400> SEQUENCE: 107

Gly Ile Ser Trp Ser Gly Gly Ser Thr Asp Tyr Ala Asp Ser Val Lys
1               5                   10                  15
Gly

<210> SEQ ID NO 108
<211> LENGTH: 17
<212> TYPE: PRT
<213> ORGANISM: Artificial Sequence
<220> FEATURE:
<223> OTHER INFORMATION: antibody sequence

<400> SEQUENCE: 108

Val Phe Ser Gly Ala Glu Thr Ala Tyr Tyr Pro Ser Asp Asp Tyr Asp
1               5                   10                  15
Tyr

<210> SEQ ID NO 109
<211> LENGTH: 5
<212> TYPE: PRT
<213> ORGANISM: Artificial Sequence
<220> FEATURE:
<223> OTHER INFORMATION: antibody sequence

<400> SEQUENCE: 109

Asn Tyr Gly Met Gly
1               5

<210> SEQ ID NO 110
<211> LENGTH: 17
<212> TYPE: PRT
<213> ORGANISM: Artificial Sequence
<220> FEATURE:
<223> OTHER INFORMATION: antibody sequence

<400> SEQUENCE: 110

Gly Ile Thr Trp Ser Gly Gly Ser Thr His Tyr Ala Asp Leu Val Lys
1               5                   10                  15
Gly

<210> SEQ ID NO 111
<211> LENGTH: 17
<212> TYPE: PRT
<213> ORGANISM: Artificial Sequence
<220> FEATURE:
<223> OTHER INFORMATION: antibody sequence

<400> SEQUENCE: 111

Val Phe Ser Gly Ala Glu Thr Ala Tyr Tyr Pro Ser Thr Glu Tyr Asp
1               5                   10                  15
Tyr

<210> SEQ ID NO 112
<211> LENGTH: 5
<212> TYPE: PRT
<213> ORGANISM: Artificial Sequence
<220> FEATURE:
<223> OTHER INFORMATION: antibody sequence
```

```
<400> SEQUENCE: 112

Asn Tyr Gly Met Gly
1               5

<210> SEQ ID NO 113
<211> LENGTH: 17
<212> TYPE: PRT
<213> ORGANISM: Artificial Sequence
<220> FEATURE:
<223> OTHER INFORMATION: antibody sequence

<400> SEQUENCE: 113

Gly Ile Ser Trp Ser Gly Gly Ser Thr Tyr Tyr Ala Asp Ser Val Lys
1               5                   10                  15

Gly

<210> SEQ ID NO 114
<211> LENGTH: 17
<212> TYPE: PRT
<213> ORGANISM: Artificial Sequence
<220> FEATURE:
<223> OTHER INFORMATION: antibody sequence

<400> SEQUENCE: 114

Val Phe Ser Gly Ala Glu Thr Ala Gln Tyr Pro Ser Tyr Asp Tyr Asp
1               5                   10                  15

Tyr

<210> SEQ ID NO 115
<211> LENGTH: 5
<212> TYPE: PRT
<213> ORGANISM: Artificial Sequence
<220> FEATURE:
<223> OTHER INFORMATION: antibody sequence

<400> SEQUENCE: 115

Asn Tyr Ala Met Gly
1               5

<210> SEQ ID NO 116
<211> LENGTH: 17
<212> TYPE: PRT
<213> ORGANISM: Artificial Sequence
<220> FEATURE:
<223> OTHER INFORMATION: antibody sequence

<400> SEQUENCE: 116

Ala Ile Ser Trp Ser Gly Gly Ser Thr Ser Tyr Ala Asp Ser Val Lys
1               5                   10                  15

Gly

<210> SEQ ID NO 117
<211> LENGTH: 21
<212> TYPE: PRT
<213> ORGANISM: Artificial Sequence
<220> FEATURE:
<223> OTHER INFORMATION: antibody sequence

<400> SEQUENCE: 117

Gln Phe Ser Gly Ala Asp Tyr Gly Phe Gly Arg Leu Gly Ile Arg Gly
1               5                   10                  15

Tyr Glu Tyr Asp Tyr
            20
```

```
<210> SEQ ID NO 118
<211> LENGTH: 5
<212> TYPE: PRT
<213> ORGANISM: Artificial Sequence
<220> FEATURE:
<223> OTHER INFORMATION: antibody sequence

<400> SEQUENCE: 118

Asn Tyr Ala Met Gly
1               5

<210> SEQ ID NO 119
<211> LENGTH: 17
<212> TYPE: PRT
<213> ORGANISM: Artificial Sequence
<220> FEATURE:
<223> OTHER INFORMATION: antibody sequence

<400> SEQUENCE: 119

Ala Ile Ser Trp Ser Gly Gly Ser Thr Tyr Tyr Ala Asp Ser Val Lys
1               5                   10                  15

Gly

<210> SEQ ID NO 120
<211> LENGTH: 21
<212> TYPE: PRT
<213> ORGANISM: Artificial Sequence
<220> FEATURE:
<223> OTHER INFORMATION: antibody sequence

<400> SEQUENCE: 120

Met Phe Ser Gly Ser Glu Ser Gln Leu Val Val Val Ile Thr Asn Leu
1               5                   10                  15

Tyr Glu Tyr Asp Tyr
            20

<210> SEQ ID NO 121
<211> LENGTH: 5
<212> TYPE: PRT
<213> ORGANISM: Artificial Sequence
<220> FEATURE:
<223> OTHER INFORMATION: antibody sequence

<400> SEQUENCE: 121

Asn Tyr Ala Met Gly
1               5

<210> SEQ ID NO 122
<211> LENGTH: 17
<212> TYPE: PRT
<213> ORGANISM: Artificial Sequence
<220> FEATURE:
<223> OTHER INFORMATION: antibody sequence

<400> SEQUENCE: 122

Thr Ile Ser Trp Ser Gly Gly Ser Thr Tyr Tyr Ala Asp Ser Val Lys
1               5                   10                  15

Gly

<210> SEQ ID NO 123
<211> LENGTH: 18
<212> TYPE: PRT
<213> ORGANISM: Artificial Sequence
<220> FEATURE:
```

<223> OTHER INFORMATION: antibody sequence

<400> SEQUENCE: 123

Ala Phe Ser Gly Ser Asp Tyr Ala Asn Thr Lys Lys Glu Val Glu Tyr
1               5                   10                  15

Asp Tyr

<210> SEQ ID NO 124
<211> LENGTH: 5
<212> TYPE: PRT
<213> ORGANISM: Artificial Sequence
<220> FEATURE:
<223> OTHER INFORMATION: antibody sequence

<400> SEQUENCE: 124

Asp Tyr Cys Ile Ala
1               5

<210> SEQ ID NO 125
<211> LENGTH: 17
<212> TYPE: PRT
<213> ORGANISM: Artificial Sequence
<220> FEATURE:
<223> OTHER INFORMATION: antibody sequence

<400> SEQUENCE: 125

Cys Ile Thr Thr Ser Asp Gly Ser Thr Tyr Tyr Ala Asp Ser Val Lys
1               5                   10                  15

Gly

<210> SEQ ID NO 126
<211> LENGTH: 18
<212> TYPE: PRT
<213> ORGANISM: Artificial Sequence
<220> FEATURE:
<223> OTHER INFORMATION: antibody sequence

<400> SEQUENCE: 126

Tyr Phe Gly Tyr Gly Cys Tyr Gly Gly Ala Gln Asp Tyr Arg Ala Met
1               5                   10                  15

Asp Tyr

<210> SEQ ID NO 127
<211> LENGTH: 5
<212> TYPE: PRT
<213> ORGANISM: Artificial Sequence
<220> FEATURE:
<223> OTHER INFORMATION: antibody sequence

<400> SEQUENCE: 127

Arg Tyr Thr Met Gly
1               5

<210> SEQ ID NO 128
<211> LENGTH: 17
<212> TYPE: PRT
<213> ORGANISM: Artificial Sequence
<220> FEATURE:
<223> OTHER INFORMATION: antibody sequence

<400> SEQUENCE: 128

Ala Ile Ser Trp Ser Gly Gly Arg Thr Asn Phe Ala Gly Ser Val Lys
1               5                   10                  15

Gly

<210> SEQ ID NO 129
<211> LENGTH: 13
<212> TYPE: PRT
<213> ORGANISM: Artificial Sequence
<220> FEATURE:
<223> OTHER INFORMATION: antibody sequence

<400> SEQUENCE: 129

Asp Trp Leu Pro Val Pro Gly Arg Glu Ser Tyr Asp Tyr
1               5                   10

<210> SEQ ID NO 130
<211> LENGTH: 5
<212> TYPE: PRT
<213> ORGANISM: Artificial Sequence
<220> FEATURE:
<223> OTHER INFORMATION: antibody sequence

<400> SEQUENCE: 130

Asn Tyr Ala Met Gly
1               5

<210> SEQ ID NO 131
<211> LENGTH: 17
<212> TYPE: PRT
<213> ORGANISM: Artificial Sequence
<220> FEATURE:
<223> OTHER INFORMATION: antibody sequence

<400> SEQUENCE: 131

Ala Ile Ser Trp Ser Gly Gly Met Thr Asp His Ala Asp Ser Val Lys
1               5                   10                  15

Gly

<210> SEQ ID NO 132
<211> LENGTH: 21
<212> TYPE: PRT
<213> ORGANISM: Artificial Sequence
<220> FEATURE:
<223> OTHER INFORMATION: antibody sequence

<400> SEQUENCE: 132

Ala Phe Ala Gly Asp Ile Pro Tyr Gly Ser Ser Trp Tyr Gly Asp Pro
1               5                   10                  15

Thr Thr Tyr Asp Tyr
            20

<210> SEQ ID NO 133
<211> LENGTH: 5
<212> TYPE: PRT
<213> ORGANISM: Artificial Sequence
<220> FEATURE:
<223> OTHER INFORMATION: antibody sequence

<400> SEQUENCE: 133

Thr Phe Ser Met Ala
1               5

<210> SEQ ID NO 134
<211> LENGTH: 17
<212> TYPE: PRT
<213> ORGANISM: Artificial Sequence
<220> FEATURE:
<223> OTHER INFORMATION: antibody sequence

```
<400> SEQUENCE: 134

Ala Ile Asn Trp Ser Gly Gly Ser Thr Arg Tyr Ala Asp Ser Val Ser
1               5                   10                  15

Asp

<210> SEQ ID NO 135
<211> LENGTH: 15
<212> TYPE: PRT
<213> ORGANISM: Artificial Sequence
<220> FEATURE:
<223> OTHER INFORMATION: antibody sequence

<400> SEQUENCE: 135

Arg Arg Gly Gly Ile Tyr Tyr Ser Thr Gln Asn Asp Tyr Asp Tyr
1               5                   10                  15

<210> SEQ ID NO 136
<211> LENGTH: 5
<212> TYPE: PRT
<213> ORGANISM: Artificial Sequence
<220> FEATURE:
<223> OTHER INFORMATION: antibody sequence

<400> SEQUENCE: 136

Asp Tyr Arg Met Gly
1               5

<210> SEQ ID NO 137
<211> LENGTH: 17
<212> TYPE: PRT
<213> ORGANISM: Artificial Sequence
<220> FEATURE:
<223> OTHER INFORMATION: antibody sequence

<400> SEQUENCE: 137

Thr Ile Ser Trp Ser Gly Gly Leu Thr Tyr Tyr Ala Asp Ser Val Lys
1               5                   10                  15

Gly

<210> SEQ ID NO 138
<211> LENGTH: 14
<212> TYPE: PRT
<213> ORGANISM: Artificial Sequence
<220> FEATURE:
<223> OTHER INFORMATION: antibody sequence

<400> SEQUENCE: 138

Gly Gly Gly Tyr Ala Gly Gly Thr Tyr Tyr His Pro Glu Glu
1               5                   10

<210> SEQ ID NO 139
<211> LENGTH: 125
<212> TYPE: PRT
<213> ORGANISM: Artificial Sequence
<220> FEATURE:
<223> OTHER INFORMATION: antibody sequence

<400> SEQUENCE: 139

Glu Val Gln Leu Val Glu Ser Gly Gly Gly Leu Val Gln Ala Gly Gly
1               5                   10                  15

Ser Leu Arg Leu Ser Cys Thr Ala Ser Gly Arg Thr Phe Ser Ser Tyr
                20                  25                  30

Ala Met Gly Trp Phe Arg Gln Ala Pro Gly Lys Glu Arg Glu Phe Val
            35                  40                  45
```

Ala Ala Ile Ser Trp Ser Gly Gly Thr Thr Tyr Ala Asp Ser Val
        50                  55                  60

Lys Gly Arg Phe Thr Ile Ser Arg Asp Asn Ala Lys Asn Thr Val Ser
65                  70                  75                  80

Leu Gln Met Asn Ser Leu Lys Pro Glu Asp Thr Ala Val Tyr Phe Cys
                85                  90                  95

Ala Ala Ser Leu Asp Cys Ser Gly Pro Gly Cys His Thr Ala Glu Tyr
                100                 105                 110

Asp Tyr Trp Gly Gln Gly Thr Gln Val Thr Val Ser Ser
        115                 120                 125

<210> SEQ ID NO 140
<211> LENGTH: 125
<212> TYPE: PRT
<213> ORGANISM: Artificial Sequence
<220> FEATURE:
<223> OTHER INFORMATION: antibody sequence

<400> SEQUENCE: 140

Glu Val Gln Leu Val Glu Ser Gly Gly Gly Leu Val Gln Ala Gly Gly
1               5                   10                  15

Ser Leu Arg Leu Ser Cys Ala Ala Thr Gly Arg Thr Phe Ser Glu Tyr
                20                  25                  30

Ala Met Gly Trp Phe Arg Gln Ala Pro Gly Lys Glu Arg Glu Phe Ala
            35                  40                  45

Ala Ala Ile Ser Trp Thr Gly Ser Lys Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Ser Asp Cys Ser Gly Pro Gly Cys His Thr Glu Glu Tyr
                100                 105                 110

Asp Tyr Trp Gly Gln Gly Thr Gln Val Thr Val Ser Ser
        115                 120                 125

<210> SEQ ID NO 141
<211> LENGTH: 125
<212> TYPE: PRT
<213> ORGANISM: Artificial Sequence
<220> FEATURE:
<223> OTHER INFORMATION: antibody sequence

<400> SEQUENCE: 141

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
                20                  25                  30

Ala Met Gly Trp Phe Arg Gln Ala Pro Gly Lys Glu Arg Glu Phe Val
            35                  40                  45

Ala Ala Val Ser Trp Ser Gly Gly Ser Thr Tyr Tyr Ala Asp Ser Val
        50                  55                  60

Lys Gly Arg Phe Thr Ile Ser Arg Asp Asn Ala Arg Asn Thr Val Tyr
65                  70                  75                  80

Leu Gln Met Asn Ser Leu Asn Pro Glu Asp Thr Ala Val Tyr Tyr Cys
                85                  90                  95

Ala Ala Ser Gln Asp Cys Ser Gly Pro Gly Cys Tyr Thr Asn Glu Tyr

-continued

```
                100                 105                 110
Asp Ser Trp Gly Gln Gly Thr Gln Val Thr Val Ser Ser
        115                 120                 125

<210> SEQ ID NO 142
<211> LENGTH: 125
<212> TYPE: PRT
<213> ORGANISM: Artificial Sequence
<220> FEATURE:
<223> OTHER INFORMATION: antibody sequence

<400> SEQUENCE: 142

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Asn Tyr
            20                  25                  30

Ala Met Ala Trp Phe Arg Gln Ala Pro Glu Lys Glu Arg Asp Phe Leu
        35                  40                  45

Ala Ala Val Ser Trp Ser Gly Arg Thr Tyr Tyr Ala Asp Ser Val
    50                  55                  60

Lys Gly Arg Phe Thr Ile Ser Arg Asp Asn Ala Lys Asn Thr Val Asn
65                  70                  75                  80

Leu Gln Met Asn Ser Leu Lys Pro Glu Asp Thr Ala Val Tyr Tyr Cys
                85                  90                  95

Ala Ala Ser Leu Ser Cys Ser Gly Pro Gly Cys Ser Leu Glu Glu Tyr
            100                 105                 110

Asp Tyr Trp Gly Gln Gly Thr Gln Val Thr Val Ser Ser
        115                 120                 125

<210> SEQ ID NO 143
<211> LENGTH: 127
<212> TYPE: PRT
<213> ORGANISM: Artificial Sequence
<220> FEATURE:
<223> OTHER INFORMATION: antibody sequence

<400> SEQUENCE: 143

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Pro Phe Ser Asn Tyr
            20                  25                  30

Ala Met Gly Trp Phe Arg Gln Ala Pro Gly Lys Glu Arg Glu Phe Val
        35                  40                  45

Thr Val Ile Ser Trp Ser Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gln Phe Ser Gly Ala Ser Thr Val Val Ala Gly Thr Ala Leu
            100                 105                 110

Asp Tyr Asp Tyr Trp Gly Gln Gly Thr Arg Val Thr Val Ser Ser
        115                 120                 125

<210> SEQ ID NO 144
<211> LENGTH: 126
<212> TYPE: PRT
<213> ORGANISM: Artificial Sequence
<220> FEATURE:
```

<223> OTHER INFORMATION: antibody sequence

<400> SEQUENCE: 144

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Pro Phe Ser Asn Tyr
            20                  25                  30

Gly Met Gly Trp Phe Arg Gln Ala Pro Gly Lys Lys Arg Glu Phe Val
        35                  40                  45

Ala Gly Ile Ser Trp Ser Gly Ser Thr Asp Tyr Ala Asp Ser Val
    50                  55                  60

Lys Gly Arg Leu Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Val Phe Ser Gly Ala Glu Thr Ala Tyr Tyr Pro Ser Asp Asp
            100                 105                 110

Tyr Asp Tyr Trp Gly Gln Gly Thr Gln Val Thr Val Ser Ser
        115                 120                 125

<210> SEQ ID NO 145
<211> LENGTH: 126
<212> TYPE: PRT
<213> ORGANISM: Artificial Sequence
<220> FEATURE:
<223> OTHER INFORMATION: antibody sequence

<400> SEQUENCE: 145

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Pro Phe Ser Asn Tyr
            20                  25                  30

Gly Met Gly Trp Phe Arg Gln Ala Pro Gly Lys Lys Arg Glu Phe Val
        35                  40                  45

Ala Gly Ile Ser Trp Ser Gly Ser Thr Asp Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Val Phe Ser Gly Ala Glu Thr Ala Tyr Tyr Pro Ser Asp Asp
            100                 105                 110

Tyr Asp Tyr Trp Gly Gln Gly Thr Gln Val Thr Val Ser Ser
        115                 120                 125

<210> SEQ ID NO 146
<211> LENGTH: 126
<212> TYPE: PRT
<213> ORGANISM: Artificial Sequence
<220> FEATURE:
<223> OTHER INFORMATION: antibody sequence

<400> SEQUENCE: 146

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Pro Phe Ser Asn Tyr
            20                  25                  30

Gly Met Gly Trp Phe Arg Gln Ala Pro Gly Lys Lys Arg Glu Ser Val

```
                 35                  40                  45

Ala Gly Ile Ser Trp Ser Gly Gly Ser Thr Asp Tyr Ala Asp Ser Val
         50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Val Phe Ser Gly Ala Glu Thr Ala Tyr Tyr Pro Ser Asp Asp
                100                 105                 110

Tyr Asp Tyr Trp Gly Gln Gly Thr Gln Val Thr Val Ser Ser
                115                 120                 125

<210> SEQ ID NO 147
<211> LENGTH: 126
<212> TYPE: PRT
<213> ORGANISM: Artificial Sequence
<220> FEATURE:
<223> OTHER INFORMATION: antibody sequence

<400> SEQUENCE: 147

Glu Val Gln Leu Val Glu Ser Gly Gly Gly Leu Val Gln Ala Gly Gly
 1               5                  10                  15

Ser Leu Arg Leu Ser Cys Ala Val Ser Gly Arg Pro Phe Ser Asn Tyr
                 20                  25                  30

Gly Met Gly Trp Phe Arg Gln Ala Pro Gly Lys Glu Arg Glu Phe Val
                 35                  40                  45

Ala Gly Ile Thr Trp Ser Gly Gly Ser Thr His Tyr Ala Asp Leu Val
         50                  55                  60

Lys Gly Arg Phe Thr Ile Ser Arg Asp Asn Ala Lys Asn Thr Val His
 65                  70                  75                  80

Leu Gln Met Asn Ser Leu Lys Pro Glu Asp Thr Ala Val Tyr Tyr Cys
                 85                  90                  95

Ala Ala Val Phe Ser Gly Ala Glu Thr Ala Tyr Tyr Pro Ser Thr Glu
                100                 105                 110

Tyr Asp Tyr Trp Gly Gln Gly Thr Gln Val Thr Val Ser Ser
                115                 120                 125

<210> SEQ ID NO 148
<211> LENGTH: 126
<212> TYPE: PRT
<213> ORGANISM: Artificial Sequence
<220> FEATURE:
<223> OTHER INFORMATION: antibody sequence

<400> SEQUENCE: 148

Glu Val Gln Leu Val Glu Ser Gly Gly Gly Leu Val Gln Ala Gly Gly
 1               5                  10                  15

Ser Leu Arg Leu Ser Cys Ala Ala Ser Gly Arg Pro Phe Asn Asn Tyr
                 20                  25                  30

Gly Met Gly Trp Phe Arg Gln Ala Pro Gly Lys Glu Arg Glu Phe Val
                 35                  40                  45

Ala Gly Ile Ser Trp Ser Gly Gly Ser Thr Tyr Tyr Ala Asp Ser Val
         50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95
```

Ala Ala Val Phe Ser Gly Ala Glu Thr Ala Gln Tyr Pro Tyr Asp
            100                 105                 110

Tyr Asp Tyr Trp Gly Gln Gly Thr Gln Val Thr Val Ser Ser
        115                 120                 125

<210> SEQ ID NO 149
<211> LENGTH: 130
<212> TYPE: PRT
<213> ORGANISM: Artificial Sequence
<220> FEATURE:
<223> OTHER INFORMATION: antibody sequence

<400> SEQUENCE: 149

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Pro Phe Ser Asn Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Gly Ser Thr Ser Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Pro Lys Pro Glu Asp Thr Ala Ile Tyr Tyr Cys
                85                  90                  95

Ala Ala Gln Phe Ser Gly Ala Asp Tyr Gly Phe Gly Arg Leu Gly Ile
            100                 105                 110

Arg Gly Tyr Glu Tyr Asp Tyr Trp Gly Gln Gly Thr Gln Val Thr Val
        115                 120                 125

Ser Ser
    130

<210> SEQ ID NO 150
<211> LENGTH: 130
<212> TYPE: PRT
<213> ORGANISM: Artificial Sequence
<220> FEATURE:
<223> OTHER INFORMATION: antibody sequence

<400> SEQUENCE: 150

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Met Phe Ser Gly Ser Glu Ser Gln Leu Val Val Val Ile Thr
            100                 105                 110

Asn Leu Tyr Glu Tyr Asp Tyr Trp Gly Gln Gly Thr Gln Val Thr Val
        115                 120                 125

Ser Ser
    130

```
<210> SEQ ID NO 151
<211> LENGTH: 127
<212> TYPE: PRT
<213> ORGANISM: Artificial Sequence
<220> FEATURE:
<223> OTHER INFORMATION: antibody sequence

<400> SEQUENCE: 151

Glu Val Gln Leu Val Glu Ser Gly Gly Gly Leu Val Gln Ala Gly
1               5                   10                  15

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Glu Phe Val
        35                  40                  45

Ala Thr Ile Ser Trp Ser Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ala Phe Ser Gly Ser Asp Tyr Ala Asn Thr Lys Lys Glu Val
            100                 105                 110

Glu Tyr Asp Tyr Trp Gly Gln Gly Thr Gln Val Thr Val Ser Ser
        115                 120                 125

<210> SEQ ID NO 152
<211> LENGTH: 127
<212> TYPE: PRT
<213> ORGANISM: Artificial Sequence
<220> FEATURE:
<223> OTHER INFORMATION: antibody sequence

<400> SEQUENCE: 152

Glu Val Gln Leu Val Glu Ser Gly Gly Gly Leu Val Gln Ala Gly
1               5                   10                  15

Ser Leu Arg Leu Ser Cys Ala Ala Ser Gly Phe Thr Phe Asp Asp Tyr
            20                  25                  30

Cys Ile Ala Trp Phe Arg Gln Ala Pro Gly Lys Glu Arg Glu Pro Val
        35                  40                  45

Ser Cys Ile Thr Thr Ser Asp Gly Ser Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Arg Leu Lys Pro Glu Asp Thr Ala Val Tyr Tyr Cys
                85                  90                  95

Ala Ala Tyr Phe Gly Tyr Gly Cys Tyr Gly Gly Ala Gln Asp Tyr Arg
            100                 105                 110

Ala Met Asp Tyr Trp Gly Lys Gly Thr Leu Val Thr Val Ser Ser
        115                 120                 125

<210> SEQ ID NO 153
<211> LENGTH: 122
<212> TYPE: PRT
<213> ORGANISM: Artificial Sequence
<220> FEATURE:
<223> OTHER INFORMATION: antibody sequence

<400> SEQUENCE: 153
```

-continued

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Arg Tyr
            20                  25                  30

Thr Met Gly Trp Phe Arg Gln Ala Pro Gly Lys Glu Arg Glu Phe Val
        35                  40                  45

Ala Ala Ile Ser Trp Ser Gly Arg Thr Asn Phe Ala Gly Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
            85                  90                  95

Ala Ala Asp Trp Leu Pro Val Pro Gly Arg Glu Ser Tyr Asp Tyr Trp
            100                 105                 110

Gly Gln Gly Thr Gln Val Thr Val Ser Ser
            115                 120

<210> SEQ ID NO 154
<211> LENGTH: 130
<212> TYPE: PRT
<213> ORGANISM: Artificial Sequence
<220> FEATURE:
<223> OTHER INFORMATION: antibody sequence

<400> SEQUENCE: 154

Glu Val Gln Leu Val Glu Ser Gly Gly Gly Leu Val Gln Ala Gly Gly
1               5                   10                  15

Ser Leu Arg Leu Ser Cys Ile Ala Ser Gly Arg Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Gly Met Thr Asp His Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
            85                  90                  95

Ala Ala Ala Phe Ala Gly Asp Ile Pro Tyr Gly Ser Ser Trp Tyr Gly
            100                 105                 110

Asp Pro Thr Thr Tyr Asp Tyr Trp Gly Gln Gly Thr Gln Val Thr Val
            115                 120                 125

Ser Ser
    130

<210> SEQ ID NO 155
<211> LENGTH: 124
<212> TYPE: PRT
<213> ORGANISM: Artificial Sequence
<220> FEATURE:
<223> OTHER INFORMATION: antibody sequence

<400> SEQUENCE: 155

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Ser Ser Thr Phe
            20                  25                  30

Ser Met Ala Trp Phe Arg Gln Ala Pro Arg Lys Glu Arg Glu Phe Val
        35                  40                  45

```
Ala Ala Ile Asn Trp Ser Gly Gly Ser Thr Arg Tyr Ala Asp Ser Val
    50                  55                  60

Ser Asp Arg Phe Ala Ile Ser Arg Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Ala Ala Arg Arg Gly Gly Ile Tyr Tyr Ser Thr Gln Asn Asp Tyr Asp
            100                 105                 110

Tyr Trp Gly Gln Gly Thr Gln Val Thr Val Ser Ser
            115                 120
```

<210> SEQ ID NO 156
<211> LENGTH: 123
<212> TYPE: PRT
<213> ORGANISM: Artificial Sequence
<220> FEATURE:
<223> OTHER INFORMATION: antibody sequence

<400> SEQUENCE: 156

```
Glu Val Gln Leu Val Glu Ser Gly Gly Gly Leu Val Gln Ala Gly Gly
1               5                   10                  15

Ser Leu Arg Leu Ser Cys Ala Val Ser Val Arg Thr Phe Ser Asp Tyr
            20                  25                  30

Arg Met Gly Trp Phe Arg Gln Ala Pro Gly Lys Glu Arg Glu Phe Val
        35                  40                  45

Ser Thr Ile Ser Trp Ser Gly Gly Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Ala Gly Gly Gly Tyr Ala Gly Gly Thr Tyr Tyr His Pro Glu Glu
            100                 105                 110

Trp Gly Gln Gly Thr Gln Val Thr Val Ser Ser
            115                 120
```

<210> SEQ ID NO 157
<211> LENGTH: 315
<212> TYPE: PRT
<213> ORGANISM: Homo sapiens

<400> SEQUENCE: 157

```
Met Leu Ser Leu Leu His Ala Ser Thr Leu Ala Val Leu Gly Ala Leu
1               5                   10                  15

Cys Val Tyr Gly Ala Gly His Leu Glu Gln Pro Gln Ile Ser Ser Thr
            20                  25                  30

Lys Thr Leu Ser Lys Thr Ala Arg Leu Glu Cys Val Val Ser Gly Ile
        35                  40                  45

Thr Ile Ser Ala Thr Ser Val Tyr Trp Tyr Arg Glu Arg Pro Gly Glu
    50                  55                  60

Val Ile Gln Phe Leu Val Ser Ile Ser Tyr Asp Gly Thr Val Arg Lys
65                  70                  75                  80

Glu Ser Gly Ile Pro Ser Gly Lys Phe Glu Val Asp Arg Ile Pro Glu
                85                  90                  95

Thr Ser Thr Ser Thr Leu Thr Ile His Asn Val Glu Lys Gln Asp Ile
            100                 105                 110
```

Ala Thr Tyr Tyr Cys Ala Leu Trp Glu Ala Gln Gln Glu Leu Gly Lys
            115                 120                 125

Lys Ile Lys Val Phe Gly Pro Gly Thr Lys Leu Ile Ile Thr Asp Lys
130                 135                 140

Gln Leu Asp Ala Asp Val Ser Pro Lys Pro Thr Ile Phe Leu Pro Ser
145                 150                 155                 160

Ile Ala Glu Thr Lys Leu Gln Lys Ala Gly Thr Tyr Leu Cys Leu Leu
                165                 170                 175

Glu Lys Phe Phe Pro Asp Val Ile Lys Ile His Trp Glu Glu Lys Lys
            180                 185                 190

Ser Asn Thr Ile Leu Gly Ser Gln Glu Gly Asn Thr Met Lys Thr Asn
        195                 200                 205

Asp Thr Tyr Met Lys Phe Ser Trp Leu Thr Val Pro Glu Lys Ser Leu
    210                 215                 220

Asp Lys Glu His Arg Cys Ile Val Arg His Glu Asn Asn Lys Asn Gly
225                 230                 235                 240

Val Asp Gln Glu Ile Ile Phe Pro Pro Ile Lys Thr Asp Val Ile Thr
                245                 250                 255

Met Asp Pro Lys Asp Asn Cys Ser Lys Asp Ala Asn Asp Thr Leu Leu
            260                 265                 270

Leu Gln Leu Thr Asn Thr Ser Ala Tyr Tyr Met Tyr Leu Leu Leu Leu
        275                 280                 285

Leu Lys Ser Val Val Tyr Phe Ala Ile Ile Thr Cys Cys Leu Leu Arg
    290                 295                 300

Arg Thr Ala Phe Cys Cys Asn Gly Glu Lys Ser
305                 310                 315

<210> SEQ ID NO 158
<211> LENGTH: 292
<212> TYPE: PRT
<213> ORGANISM: Homo sapiens

<400> SEQUENCE: 158

Met Gln Arg Ile Ser Ser Leu Ile His Leu Ser Leu Phe Trp Ala Gly
1               5                   10                  15

Val Met Ser Ala Ile Glu Leu Val Pro Glu His Gln Thr Val Pro Val
                20                  25                  30

Ser Ile Gly Val Pro Ala Thr Leu Arg Cys Ser Met Lys Gly Glu Ala
            35                  40                  45

Ile Gly Asn Tyr Tyr Ile Asn Trp Tyr Arg Lys Thr Gln Gly Asn Thr
        50                  55                  60

Met Thr Phe Ile Tyr Arg Glu Lys Asp Ile Tyr Gly Pro Gly Phe Lys
65                  70                  75                  80

Asp Asn Phe Gln Gly Asp Ile Asp Ile Ala Lys Asn Leu Ala Val Leu
                85                  90                  95

Lys Ile Leu Ala Pro Ser Glu Arg Asp Glu Gly Ser Tyr Tyr Cys Ala
            100                 105                 110

Cys Asp Thr Leu Gly Met Gly Gly Glu Tyr Thr Asp Lys Leu Ile Phe
        115                 120                 125

Gly Lys Gly Thr Arg Val Thr Val Glu Pro Arg Ser Gln Pro His Thr
    130                 135                 140

Lys Pro Ser Val Phe Val Met Lys Asn Gly Thr Asn Val Ala Cys Leu
145                 150                 155                 160

Val Lys Glu Phe Tyr Pro Lys Asp Ile Arg Ile Asn Leu Val Ser Ser
                165                 170                 175

```
Lys Lys Ile Thr Glu Phe Asp Pro Ala Ile Val Ile Ser Pro Ser Gly
                180                 185                 190

Lys Tyr Asn Ala Val Lys Leu Gly Lys Tyr Glu Asp Ser Asn Ser Val
            195                 200                 205

Thr Cys Ser Val Gln His Asp Asn Lys Thr Val His Ser Thr Asp Phe
    210                 215                 220

Glu Val Lys Thr Asp Ser Thr Asp His Val Lys Pro Lys Glu Thr Glu
225                 230                 235                 240

Asn Thr Lys Gln Pro Ser Lys Ser Cys His Lys Pro Lys Ala Ile Val
                245                 250                 255

His Thr Glu Lys Val Asn Met Met Ser Leu Thr Val Leu Gly Leu Arg
            260                 265                 270

Met Leu Phe Ala Lys Thr Val Ala Val Asn Phe Leu Leu Thr Ala Lys
        275                 280                 285

Leu Phe Phe Leu
    290

<210> SEQ ID NO 159
<211> LENGTH: 5
<212> TYPE: PRT
<213> ORGANISM: Artificial Sequence
<220> FEATURE:
<223> OTHER INFORMATION: linker sequence

<400> SEQUENCE: 159

Gly Gly Gly Gly Ser
1               5

<210> SEQ ID NO 160
<211> LENGTH: 254
<212> TYPE: PRT
<213> ORGANISM: Artificial Sequence
<220> FEATURE:
<223> OTHER INFORMATION: antibody sequence

<400> SEQUENCE: 160

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Met Phe Ser Asp Asn
            20                  25                  30

Val Met Gly Trp Tyr Arg Gln Ala Pro Gly Lys Gln Arg Glu Leu Val
        35                  40                  45

Ala Thr Ile Arg Thr Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Arg
                85                  90                  95

His Thr Ile Pro Val Pro Ser Pro Tyr Asp Tyr Trp Gly Gln Gly
                100                 105                 110

Thr Gln Val Thr Val Ser Ser Gly Gly Gly Gly Ser Glu Val Gln Leu
            115                 120                 125

Val Glu Ser Gly Gly Gly Leu Val Gln Ala Gly Gly Ser Leu Arg Leu
        130                 135                 140

Ser Cys Ala Ala Ser Gly Arg Pro Phe Ser Asn Tyr Ala Met Gly Trp
145                 150                 155                 160

Phe Arg Gln Ala Pro Gly Lys Glu Arg Glu Phe Val Ala Ala Ile Ser
```

```
              165                 170                 175
Trp Ser Gly Gly Ser Thr Ser Tyr Ala Asp Ser Val Lys Gly Arg Phe
            180                 185                 190

Thr Ile Ser Arg Asp Asn Ala Lys Asn Thr Val Tyr Leu Gln Met Asn
        195                 200                 205

Ser Pro Lys Pro Glu Asp Thr Ala Ile Tyr Tyr Cys Ala Ala Gln Phe
    210                 215                 220

Ser Gly Ala Asp Tyr Gly Phe Gly Arg Leu Gly Ile Arg Gly Tyr Glu
225                 230                 235                 240

Tyr Asp Tyr Trp Gly Gln Gly Thr Gln Val Thr Val Ser Ser
                245                 250

<210> SEQ ID NO 161
<211> LENGTH: 119
<212> TYPE: PRT
<213> ORGANISM: Artificial Sequence
<220> FEATURE:
<223> OTHER INFORMATION: antibody sequence

<400> SEQUENCE: 161

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Met Phe Ser Asp Asn
            20                  25                  30

Val Met Gly Trp Tyr Arg Gln Ala Pro Gly Lys Gln Arg Glu Leu Val
        35                  40                  45

Ala Thr Ile Arg Thr Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Arg
                85                  90                  95

His Thr Ile Pro Val Pro Ser Thr Pro Tyr Asp Tyr Trp Gly Gln Gly
            100                 105                 110

Thr Gln Val Thr Val Ser Ser
        115

<210> SEQ ID NO 162
<211> LENGTH: 130
<212> TYPE: PRT
<213> ORGANISM: Artificial Sequence
<220> FEATURE:
<223> OTHER INFORMATION: antibody sequence

<400> SEQUENCE: 162

Glu Val Gln Leu Leu Glu Ser Gly Gly Gly Ser Val Gln Pro Gly Gly
1               5                   10                  15

Ser Leu Arg Leu Ser Cys Ala Ala Ser Gly Arg Pro Phe Ser Asn Tyr
            20                  25                  30

Ala Met Ser Trp Phe Arg Gln Ala Pro Gly Lys Glu Arg Glu Phe Val
        35                  40                  45

Ser Ala Ile Ser Trp Ser Gly Ser Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Ala Gln Phe Ser Gly Ala Asp Tyr Gly Phe Gly Arg Leu Gly Ile
                100                 105                 110

Arg Gly Tyr Glu Tyr Asp Tyr Trp Gly Gln Gly Thr Gln Val Thr Val
            115                 120                 125

Ser Ser
    130

<210> SEQ ID NO 163
<211> LENGTH: 130
<212> TYPE: PRT
<213> ORGANISM: Artificial Sequence
<220> FEATURE:
<223> OTHER INFORMATION: antibody sequence

<400> SEQUENCE: 163

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Pro Phe Ser Asn Tyr
            20                  25                  30

Ala Met Ser Trp Phe Arg Gln Ala Pro Gly Lys Glu Arg Glu Phe Val
        35                  40                  45

Ser Ala Ile Ser Trp Ser Gly Ser Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gln Phe Ser Gly Ala Asp Tyr Gly Phe Gly Arg Leu Gly Ile
                100                 105                 110

Arg Gly Tyr Glu Tyr Asp Tyr Trp Gly Gln Gly Thr Leu Val Thr Val
            115                 120                 125

Ser Ser
    130

<210> SEQ ID NO 164
<211> LENGTH: 254
<212> TYPE: PRT
<213> ORGANISM: Artificial Sequence
<220> FEATURE:
<223> OTHER INFORMATION: antibody sequence

<400> SEQUENCE: 164

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Met Phe Ser Asp Asn
            20                  25                  30

Val Met Gly Trp Tyr Arg Gln Ala Pro Gly Lys Gln Arg Glu Leu Val
        35                  40                  45

Ala Thr Ile Arg Thr Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Arg
                85                  90                  95

His Thr Ile Pro Val Pro Ser Thr Pro Tyr Asp Tyr Trp Gly Gln Gly
                100                 105                 110

Thr Gln Val Thr Val Ser Ser Gly Gly Gly Gly Ser Glu Val Gln Leu
            115                 120                 125
```

```
Leu Glu Ser Gly Gly Gly Ser Val Gln Pro Gly Gly Ser Leu Arg Leu
            130                 135                 140

Ser Cys Ala Ala Ser Gly Arg Pro Phe Ser Asn Tyr Ala Met Ser Trp
145                 150                 155                 160

Phe Arg Gln Ala Pro Gly Lys Glu Arg Glu Phe Val Ser Ala Ile Ser
                165                 170                 175

Trp Ser Gly Gly Ser Thr Ser Tyr Ala Asp Ser Val Lys Gly Arg Phe
                180                 185                 190

Thr Ile Ser Arg Asp Asn Ser Lys Asn Thr Leu Tyr Leu Gln Met Asn
            195                 200                 205

Ser Leu Arg Ala Glu Asp Thr Ala Val Tyr Tyr Cys Ala Ala Gln Phe
        210                 215                 220

Ser Gly Ala Asp Tyr Gly Phe Gly Arg Leu Gly Ile Arg Gly Tyr Glu
225                 230                 235                 240

Tyr Asp Tyr Trp Gly Gln Gly Thr Gln Val Thr Val Ser Ser
                245                 250

<210> SEQ ID NO 165
<211> LENGTH: 264
<212> TYPE: PRT
<213> ORGANISM: Artificial Sequence
<220> FEATURE:
<223> OTHER INFORMATION: antibody sequence

<400> SEQUENCE: 165

Glu Val Gln Leu Val Glu Ser Gly Gly Gly Leu Val Gln Ala Gly Gly
1               5                   10                  15

Ser Leu Arg Leu Ser Cys Ala Ala Ser Val Ser Ser Phe Ser Ser Tyr
            20                  25                  30

Thr Met Gly Thr Ile Arg Thr Gly Gly Ser Thr Asn Tyr Ala Asp Ser
        35                  40                  45

Val Lys Gly Gly Ile Arg Trp Asp Asp Glu Asn Pro Tyr Tyr Ala Asp
    50                  55                  60

Ser Val Lys Gly Arg Phe Thr Ile Ser Arg Asp Asn Ala Lys Asn Thr
65                  70                  75                  80

Leu Tyr Leu Gln Met Asn Ser Leu Lys Pro Glu Asp Thr Ala Asn Tyr
                85                  90                  95

Tyr Cys Ala Ala Arg Leu Val Pro Pro Gly Ile Pro Phe Glu Arg Thr
            100                 105                 110

Leu Glu Asn Met Arg Tyr Trp Gly Lys Gly Thr Leu Val Thr Val Ser
        115                 120                 125

Ser Gly Gly Gly Gly Ser Glu Val Gln Leu Val Glu Ser Gly Gly Gly
    130                 135                 140

Leu Val Gln Ala Gly Gly Ser Leu Arg Leu Cys Ala Ala Ser Gly
145                 150                 155                 160

Arg Pro Phe Ser Asn Tyr Ala Met Gly Trp Phe Arg Gln Ala Pro Gly
                165                 170                 175

Lys Glu Arg Glu Phe Val Ala Ala Ile Ser Trp Ser Gly Gly Ser Thr
            180                 185                 190

Ser Tyr Ala Asp Ser Val Lys Gly Arg Phe Thr Ile Ser Arg Asp Asn
        195                 200                 205

Ala Lys Asn Thr Val Tyr Leu Gln Met Asn Ser Pro Lys Pro Glu Asp
    210                 215                 220

Thr Ala Ile Tyr Tyr Cys Ala Ala Gln Phe Ser Gly Ala Asp Tyr Gly
225                 230                 235                 240
```

```
Phe Gly Arg Leu Gly Ile Arg Gly Tyr Glu Tyr Asp Tyr Trp Gly Gln
            245                 250                 255

Gly Thr Gln Val Thr Val Ser Ser
            260
```